United States Patent
Azevedo et al.

(10) Patent No.: US 11,890,092 B2
(45) Date of Patent: Feb. 6, 2024

(54) LOW POWER RECEIVER FOR IN VIVO CHANNEL SENSING AND INGESTIBLE SENSOR DETECTION WITH WANDERING FREQUENCY

(71) Applicant: OTSUKA PHARMACEUTICAL CO. LTD., Tokyo (JP)

(72) Inventors: Robert Azevedo, Albany, CA (US);
Neraj P. Bobra, San Jose, CA (US);
Aditya Dua, San Jose, CA (US);
Ronny X. Li, San Francisco, CA (US);
William A. Weeks, Santa Cruz, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 621 days.

(21) Appl. No.: 17/252,600

(22) PCT Filed: Jun. 14, 2019

(86) PCT No.: PCT/US2019/037307
§ 371 (c)(1),
(2) Date: Dec. 15, 2020

(87) PCT Pub. No.: WO2019/241704
PCT Pub. Date: Dec. 19, 2019

(65) Prior Publication Data
US 2021/0330216 A1    Oct. 28, 2021

Related U.S. Application Data

(60) Provisional application No. 62/685,878, filed on Jun. 15, 2018.

(51) Int. Cl.
*A61B 5/11* (2006.01)
*A61B 5/00* (2006.01)
(Continued)

(52) U.S. Cl.
CPC .......... *A61B 5/1118* (2013.01); *A61B 5/0002* (2013.01); *A61B 5/073* (2013.01);
(Continued)

(58) Field of Classification Search
CPC .... A61B 2560/0209; A61B 2562/0219; A61B 5/0002; A61B 5/0006; A61B 5/0022;
(Continued)

(56) References Cited

U.S. PATENT DOCUMENTS

| 8,114,021 B2 | 2/2012 | Robertson et al. |
|---|---|---|
| 10,365,120 B2 | 7/2019 | Schuijers et al. |
| 2017/0056650 A1 | 3/2017 | Cohen et al. |

FOREIGN PATENT DOCUMENTS

| AU | 2012216694 A1 * | 9/2012 | ........... A61B 5/0006 |
|---|---|---|---|
| AU | 2012216694 A1 | 9/2012 | |

(Continued)

OTHER PUBLICATIONS

Office Action issued in corresponding Japanese Patent Application No. 2020-570058, dated Mar. 20, 2023.
(Continued)

*Primary Examiner* — Jonathan T Kuo
*Assistant Examiner* — Vynn V Huh
(74) *Attorney, Agent, or Firm* — Pillsbury Winthrop Shaw Pittman, LLP

(57) ABSTRACT

A system, a wearable device, and a method are provided which can increase the accuracy of physiological metrics while detecting if the patient ingested digital medicine and/or improve performance of the wearable device. The wearable device can comprise machine executable instructions that when executed by the processor, cause the processor to perform various algorithms, such as, for example, at least one of a step count algorithm, a body angle algorithm, a heart rate algorithm, a peak finder algorithm, an
(Continued)

adaptive thresholding algorithm, a heart rate variability algorithm, a R-R cleaning Algorithm, a deltaR-R cleaning algorithm, a merge twin interval algorithm, a split tall intervals algorithm, an absorb short intervals algorithm, a bimodal detection algorithm, and a resting algorithm.

19 Claims, 61 Drawing Sheets

(51) Int. Cl.
- *A61B 5/07* (2006.01)
- *A61B 5/318* (2021.01)
- *G01C 22/00* (2006.01)
- *G16H 20/30* (2018.01)
- *G16H 40/67* (2018.01)

(52) U.S. Cl.
CPC ............ *A61B 5/318* (2021.01); *A61B 5/6801* (2013.01); *A61B 5/6861* (2013.01); *A61B 5/725* (2013.01); *A61B 5/7282* (2013.01); *G01C 22/006* (2013.01); *G16H 20/30* (2018.01); *G16H 40/67* (2018.01); *A61B 2562/0219* (2013.01)

(58) Field of Classification Search
CPC ............ A61B 5/02405; A61B 5/02438; A61B 5/0245; A61B 5/073; A61B 5/1116; A61B 5/1118; A61B 5/112; A61B 5/1123; A61B 5/318; A61B 5/4806; A61B 5/6801; A61B 5/6861; A61B 5/7239; A61B 5/7246; A61B 5/725; A61B 5/7264; A61B 5/7282; G01C 22/006; G16H 20/10; G16H 20/30; G16H 40/67; G16H 50/20
See application file for complete search history.

(56) References Cited

FOREIGN PATENT DOCUMENTS

| | | |
|---|---|---|
| JP | 2012-511969 A | 5/2012 |
| WO | 2017011464 A1 | 1/2017 |
| WO | 2019241704 A1 | 12/2019 |

OTHER PUBLICATIONS

International Search Report and Written Opinion for International PCT Application No. PCT/US2019/037307, dated Nov. 14, 2019.

\* cited by examiner

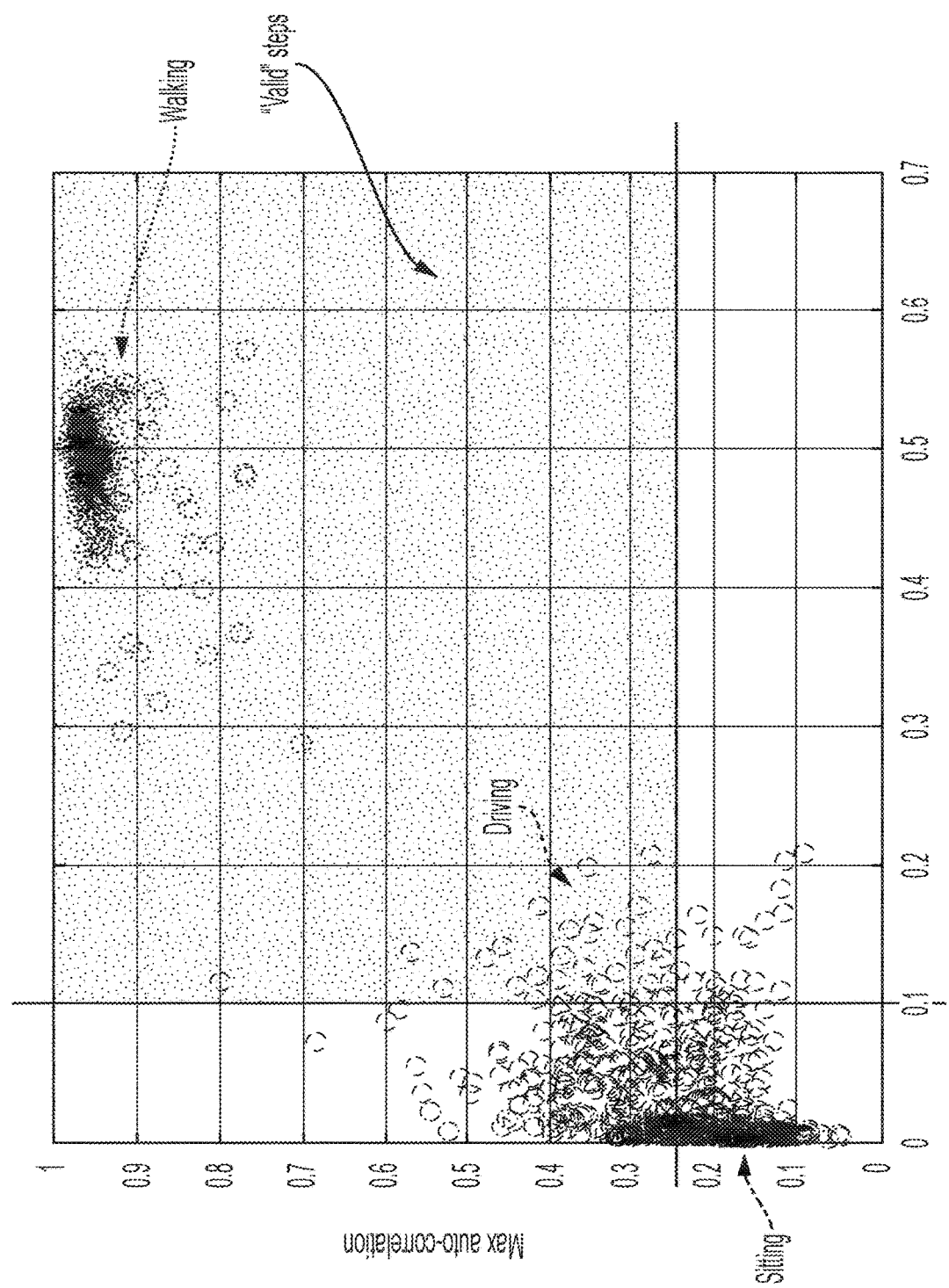

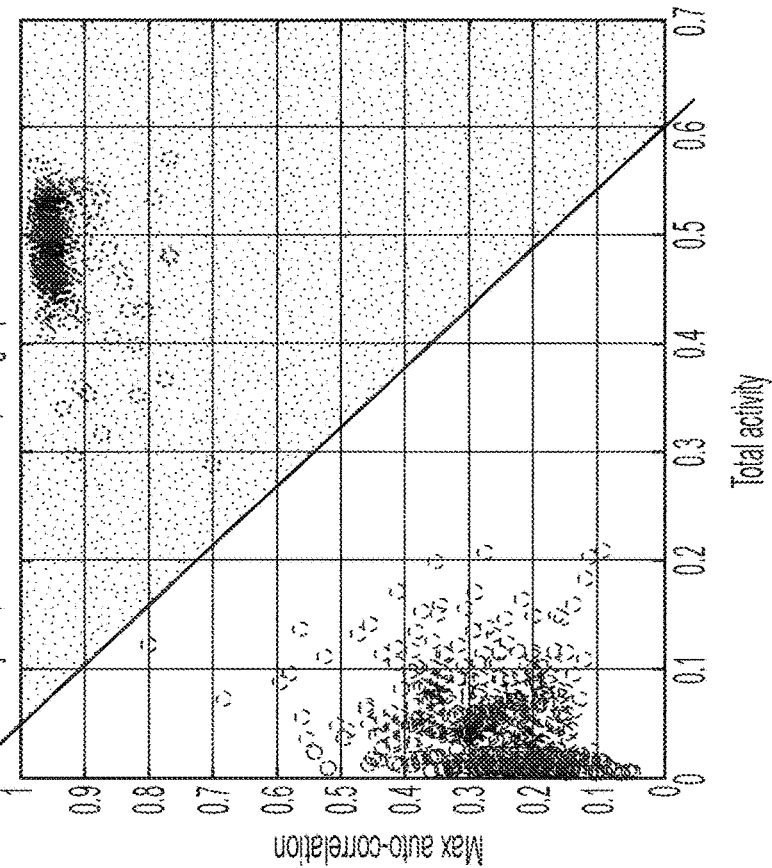
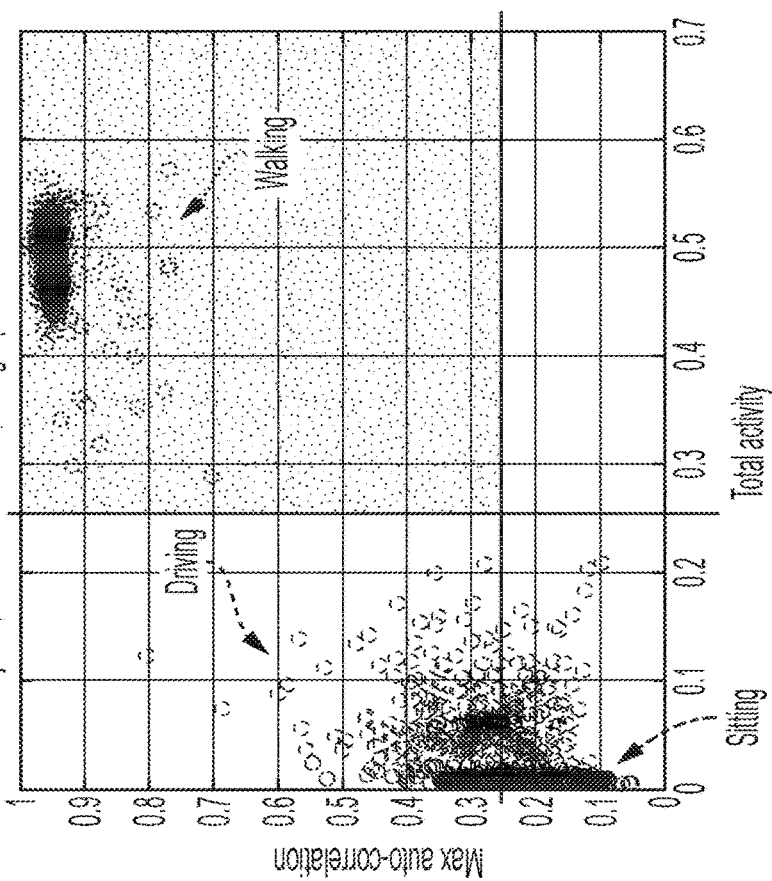
FIG. 11A
FIG. 11B

FIG. 21A

| Xbin# | Ybin# | Zbin# |
|---|---|---|
| 0 | 0 | 1 |

FIG. 21B

| Xbin# | Ybin# | Zbin# |
|---|---|---|
| 0 | 0 | 1 |

FIG. 21C

| Xbin# | Ybin# | Zbin# |
|---|---|---|
| 0 | 0 | 1 |

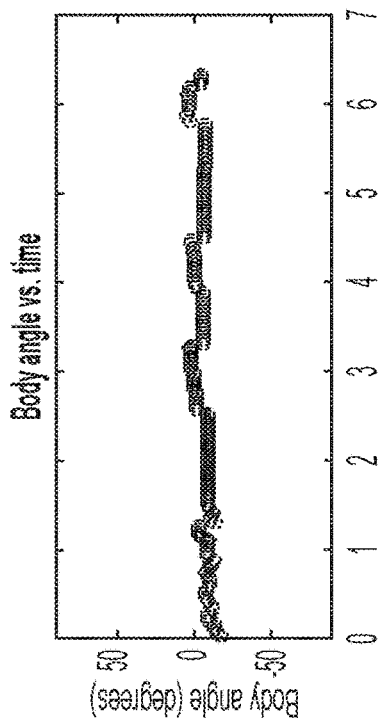
FIG. 22B
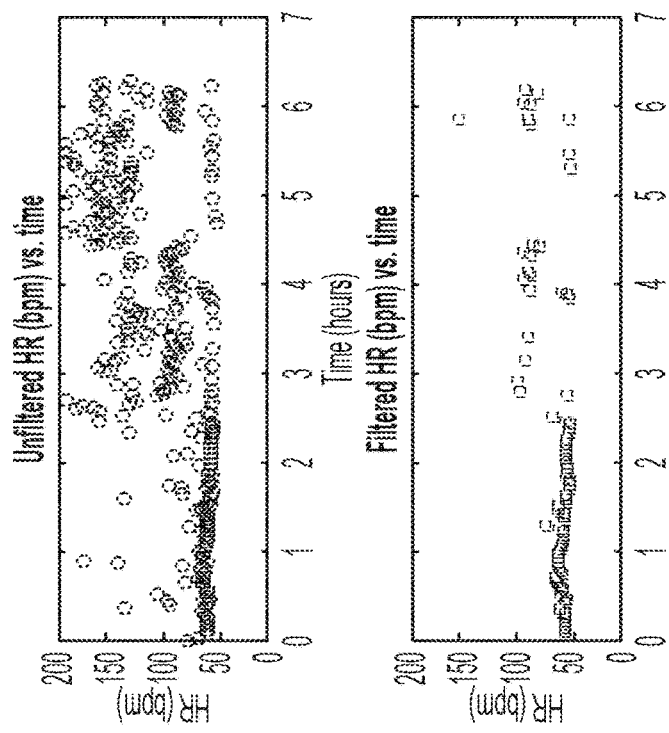
FIG. 22A
FIG. 22C

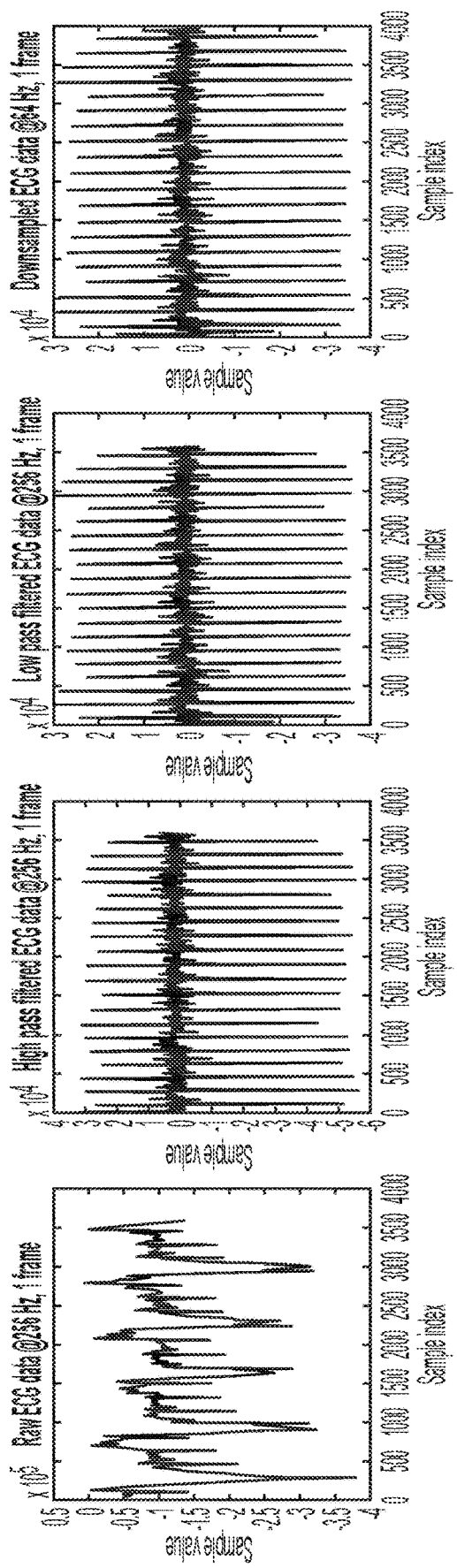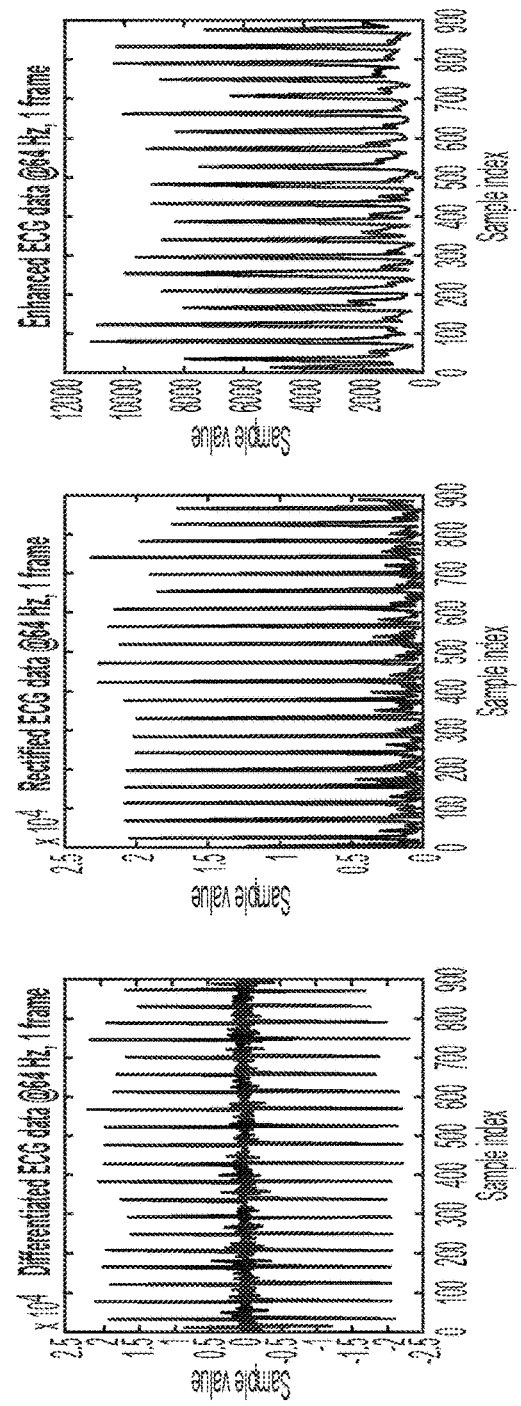
FIG. 29A FIG. 29B FIG. 29C FIG. 29D FIG. 29E FIG. 29F FIG. 29G

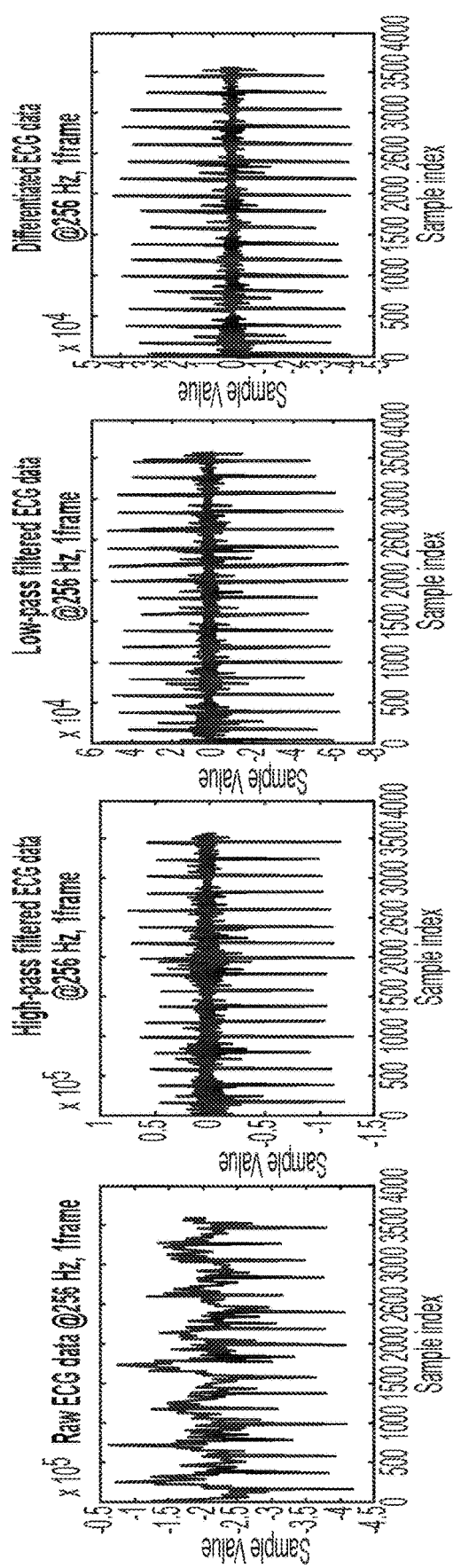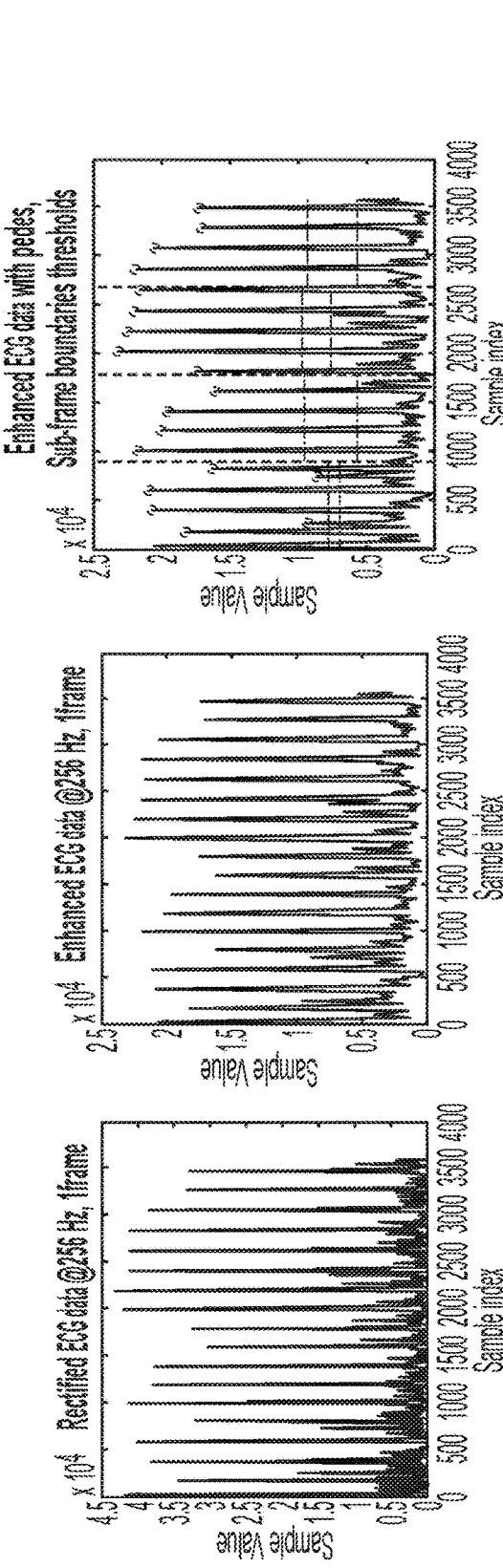
FIG. 30A, FIG. 30B, FIG. 30C, FIG. 30D, FIG. 30E, FIG. 30F, FIG. 30G

LOW POWER RECEIVER FOR IN VIVO CHANNEL SENSING AND INGESTIBLE SENSOR DETECTION WITH WANDERING FREQUENCY

CROSS-REFERENCE TO RELATED APPLICATIONS

This application is a U.S. National Stage Entry under 35 U.S.C. § 371 of International Patent Application No. PCT/US2019/037307, entitled LOW POWER RECEIVER FOR IN VIVO CHANNEL SENSING AND INGESTIBLE SENSOR DETECTION WITH WANDERING FREQUENCY, filed Jun. 14, 2019, which claims priority to U.S. Provisional Patent Application No. 62/685,878, titled LOW POWER RECEIVER FOR IN VIVO CHANNEL SENSING AND INGESTIBLE SENSOR DETECTION WITH WANDERING FREQUENCY, filed Jun. 15, 2018, the entire disclosures of which are hereby incorporated by reference herein.

BACKGROUND

Wearable receiver assemblies can be utilized to detect a signal conducted through an individual from an ingestible event marker (IEM) and/or other physiological metrics. Various examples of such receiver assemblies can feature a reusable component, which includes the firmware and electronics, and a disposable adhesive strip component, which includes the electrodes and the power source. There are challenges with analyzing data from the IEM and other physiological metrics.

SUMMARY

In an example, a system for determining a step count of a patient is provided. The system comprises a wearable device and a processor of at least one of the wearable device and a remote device communicatively coupled to the wearable device. The wearable device comprises an accelerometer and the wearable device is configured to be coupled to a body of the patient and configured to detect discontinuous data utilizing at least the accelerometer. The discontinuous data comprises frames of ingestible sensor data and frames of physiological data of the patient interspersed in time gaps between the frames of the ingestible sensor data. The processor is configured to determine the step count in a speed range of 80 to 150 steps per minute using the detected physiological data with a mean error of plus or minus 3 percent as measured over at least 1000 steps.

In another example, a wearable device comprising a processor coupled to a non-transitory memory is provided. The non-transitory memory comprises machine executable instructions that when executed by the processor, cause the processor to receive discontinuous data comprising frames of ingestible sensor data and frames of physiological data of the patient interspersed in time gaps between the frames of the ingestible sensor data and determine a step count in a speed range of 80 to 150 steps per minute using the detected physiological data with a mean error of plus or minus 3 percent as measured over at least 1000 steps.

In yet another example, a method for determining a step count of a patient from discontinuous data is provided. The method comprises receiving the discontinuous data comprising frames of ingestible sensor data and frames of physiological data interspersed in time gaps between the frames of the ingestible sensor data. The physiological data comprises accelerometer data from an accelerometer. The method comprises enhancing the accelerometer data and calculating a number of level crossings in the enhanced accelerometer data, thereby producing the step count.

In an example, a system for automatically determining an orientation is provided. The system comprises a wearable device and a processor of at least one of the wearable device and a remote device communicatively coupled to the wearable device. The wearable device comprises an accelerometer. The wearable device is configured to be coupled to a body of the patient and is configured to detect discontinuous data utilizing at least the accelerometer. The discontinuous data comprises frames of ingestible sensor data and frames of physiological data of the patient interspersed in time gaps between the frames of the ingestible sensor data. The processor is configured to automatically determine an orientation of the wearable device relative to the body of the patient utilizing the detected physiological data.

In another example, a wearable device comprising a processor coupled to a non-transitory memory is provided. The non-transitory memory comprises machine executable instructions that when executed by the processor, cause the processor to receive discontinuous data comprising frames of ingestible sensor data and frames of physiological data from interspersed in time gaps between the frames of the ingestible sensor data, wherein the physiological data comprises accelerometer data and automatically determine an orientation of the wearable device relative to a body of a patient utilizing the accelerometer data.

In yet another example, a method for automatically determining an orientation is provided. The method comprises receiving discontinuous data comprising frames of ingestible sensor data and frames of physiological data interspersed in time gaps between the frames of the ingestible sensor data, wherein the physiological data comprises accelerometer data from a wearable device. The method also comprises automatically determining an orientation of the wearable device relative to a body of a patient utilizing the accelerometer data.

In an example, a system for determining a heart rate of a patient is provided. The system comprises a wearable device comprising an electrode. The wearable device is configured to be coupled to a body of the patient and configured to detect discontinuous data utilizing at least the electrode. The discontinuous data comprises frames of ingestible sensor data and frames of physiological data of the patient interspersed in time gaps between the frames of the ingestible sensor data. The system also comprises a vector co-processor of at least one of the wearable device and a remote device communicatively coupled to the wearable device. The vector co-processor is configured to enhance the frames of physiological data. The system also comprises a processor of at least one of the wearable device and the remote device. The processor is configured to determine a heart rate of the patient using the enhanced frames of the physiological data.

In another example, a wearable device comprising a processor coupled to a non-transitory memory is provided. The non-transitory memory comprises machine executable instructions that when executed by the processor and/or a vector co-processor, cause the processor and/or coprocessor to receive discontinuous data comprising frames of ingestible sensor data and frames of physiological data of the patient interspersed in time gaps between the frames of the ingestible sensor data, enhance, by the coprocessor, the frames of physiological data, and determine, by the processor, a heart rate of the patient using the enhanced frames of the physiological data.

In yet another example, a method for determining a heart rate is provided. The method comprises receiving discontinuous data utilizing at least the electrode. The discontinuous data comprises frames of ingestible sensor data and frames of physiological data of the patient interspersed in time gaps between the frames of the ingestible sensor data. The method also comprises enhancing, by a coprocessor, the frames of physiological data and determining, by a processor, a heart rate of the patient using the enhanced frames of the physiological data.

In an example, a system for determining level crossings in discontinuous data is provided. The system comprises a wearable device a processor of at least one of the wearable device and a remote device communicatively coupled to the wearable device. The wearable device is configured to be coupled to a body of a patient and configured to detect discontinuous data. The discontinuous data comprises frames of ingestible sensor data and frames of physiological data from the patient interspersed in time gaps between the frames of the ingestible sensor data. The processor is configured to handle boundary effects in frames of the physiological data and calculate a number of level crossings.

In another example, a wearable device comprising a processor coupled to a non-transitory memory is provided. The non-transitory memory comprises machine executable instructions that when executed by the processor, cause the processor to receive discontinuous data comprising frames of ingestible sensor data and frames of physiological data from the patient interspersed in time gaps between the frames of the ingestible sensor data and handle boundary effects in frames of the physiological data and calculate a number of level crossings in the physiological data.

In yet another example, a method for determining a number of level crossing in discontinuous data is provided. The method comprises receiving discontinuous data comprising frames of ingestible sensor data and frames of physiological data from the patient interspersed in time gaps between the frames of the ingestible sensor data and handling boundary effects in frames of the physiological data and calculating the number of level crossing in the discontinuous data.

In an example, a system for determining heart rate variability of a patient is provided. The system comprises a wearable device and a processor of at least one of the wearable device and a remote device communicatively coupled to the wearable device. The wearable comprises an electrode device and is configured to be coupled to a body of a patient and is configured to detect discontinuous data utilizing at least the electrode. The discontinuous data comprises frames of ingestible sensor data and frames of physiological data from the patient interspersed in time gaps between the frames of the ingestible sensor data. The processor is configured to group at least two of the frames of the physiological data together into a block and determine heart rate variability of the patient utilizing the block.

In another example, a wearable device comprising a processor coupled to a non-transitory memory is provided. The non-transitory memory comprises machine executable instructions that when executed by the processor, cause the processor to receive discontinuous data comprising frames of ingestible sensor data and frames of physiological data from the patient interspersed in time gaps between the frames of the ingestible sensor data and group at least two of the frames of the physiological data together into a block and determine heart rate variability of the patient utilizing the block.

In yet another example, a method for determining heart rate variability of a patient is provided. The method comprises receiving discontinuous data comprising frames of ingestible sensor data and frames of physiological data from a patient interspersed in time gaps between the frames of the ingestible sensor data and grouping at least two of the frames of the physiological data together into a block and determining heart rate variability of the patient utilizing the block.

In an example, a system for determining a rest of a patient is provided. The system comprises a wearable device and a processor of at least one of the wearable device and a remote device communicatively coupled to the wearable device. The wearable device comprises an accelerometer and the wearable device is configured to be coupled to a body of the patient and is configured to detect discontinuous data utilizing at least the accelerometer and the electrode. The discontinuous data comprises frames of ingestible sensor data and frames of physiological data from the patient interspersed in time gaps between the frames of the ingestible sensor data. The physiological data comprises accelerometer data from the accelerometer. The processor is configured to determine the patient is resting based on accelerometer data.

In another example, a wearable device comprising a processor coupled to a non-transitory memory is provided. The non-transitory memory comprises machine executable instructions that when executed by the processor, cause the processor to receive discontinuous data comprising frames of ingestible sensor data and frames of physiological data from a patient interspersed in time gaps between the frames of the ingestible sensor data and determine the patient is resting based on accelerometer data.

In yet another example, a method for determining a rest of a patient is provided. The method comprises receiving discontinuous data comprising frames of ingestible sensor data and frames of physiological data from a patient interspersed in time gaps between the frames of the ingestible sensor data and determining the patient is resting based on accelerometer data.

FIGURES

The novel features of the various aspects described herein are set forth with particularity in the appended claims. The various aspects, however, both as to organization and methods of operation may be better understood by reference to the following description, taken in conjunction with the accompanying drawings as follows:

Figure 6:
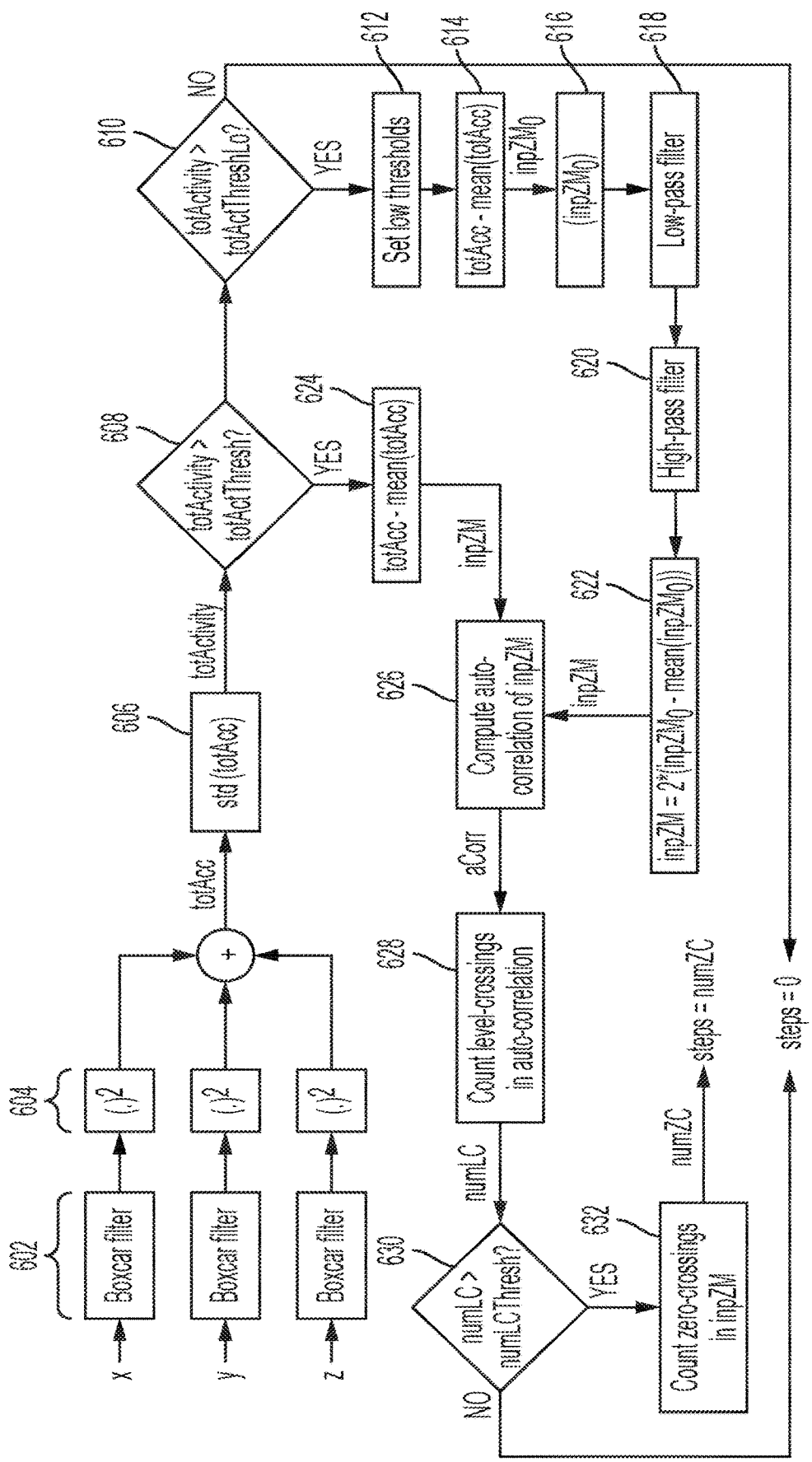
Figure 7A:
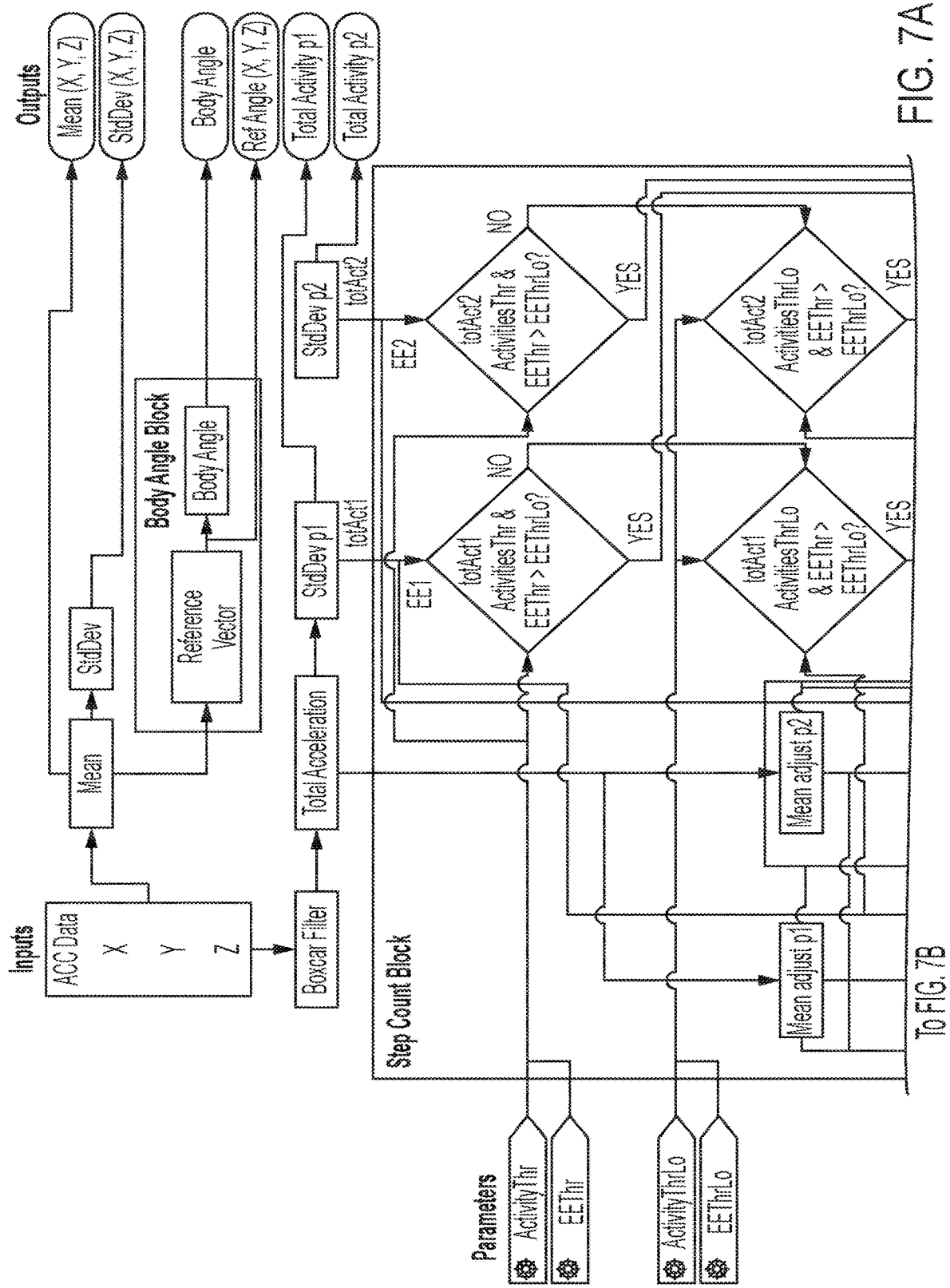
Figure 7B:
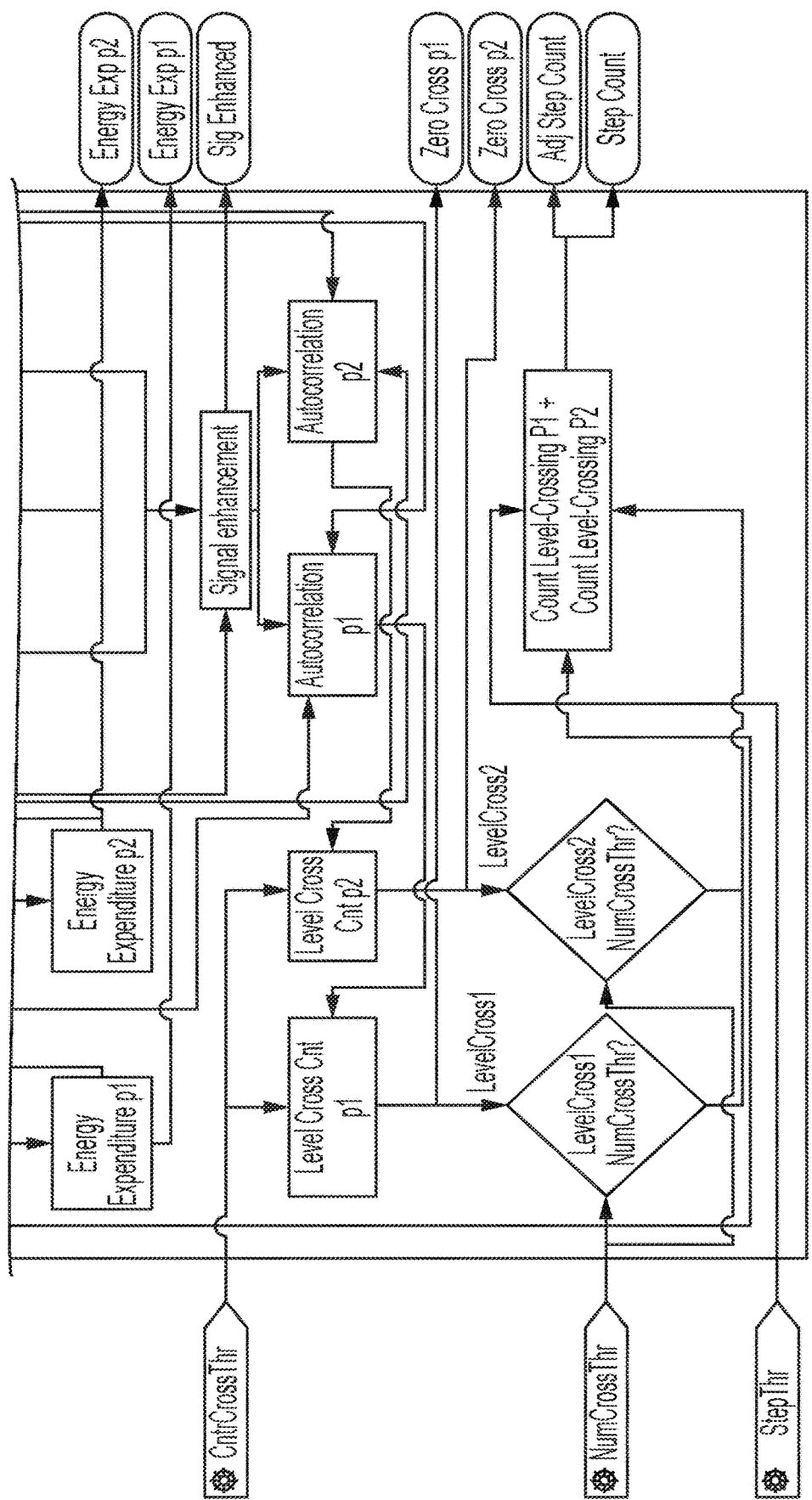
Figure 8:
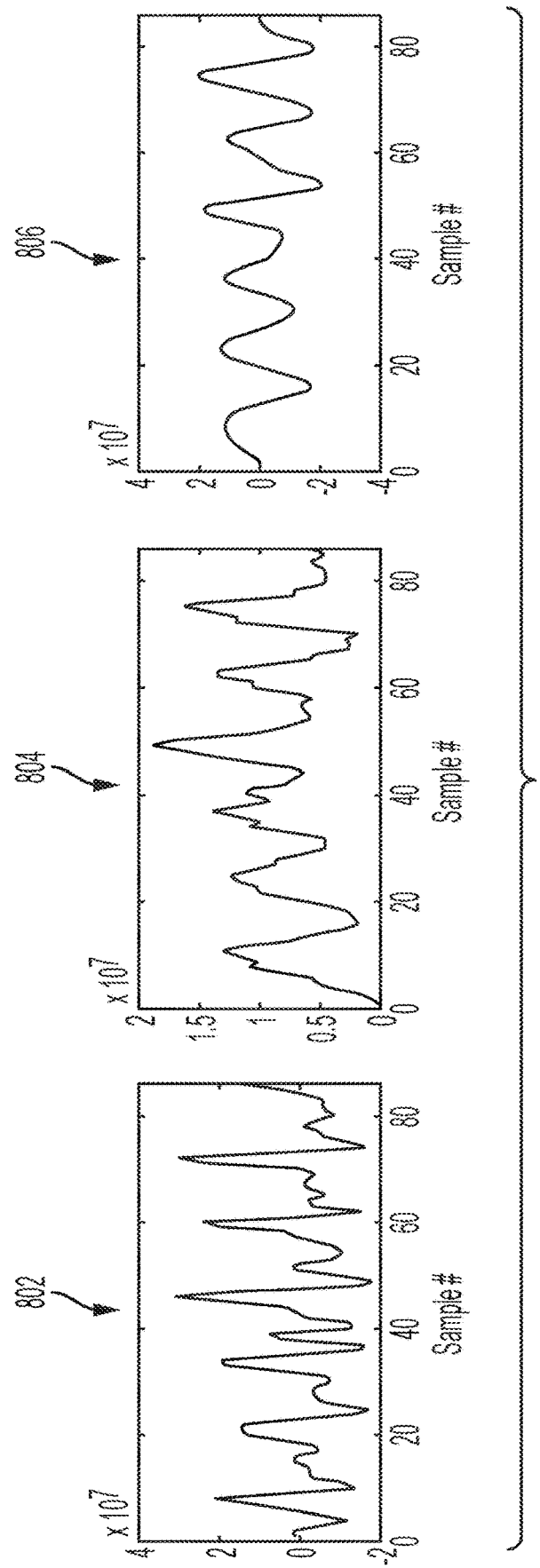
Figure 9:
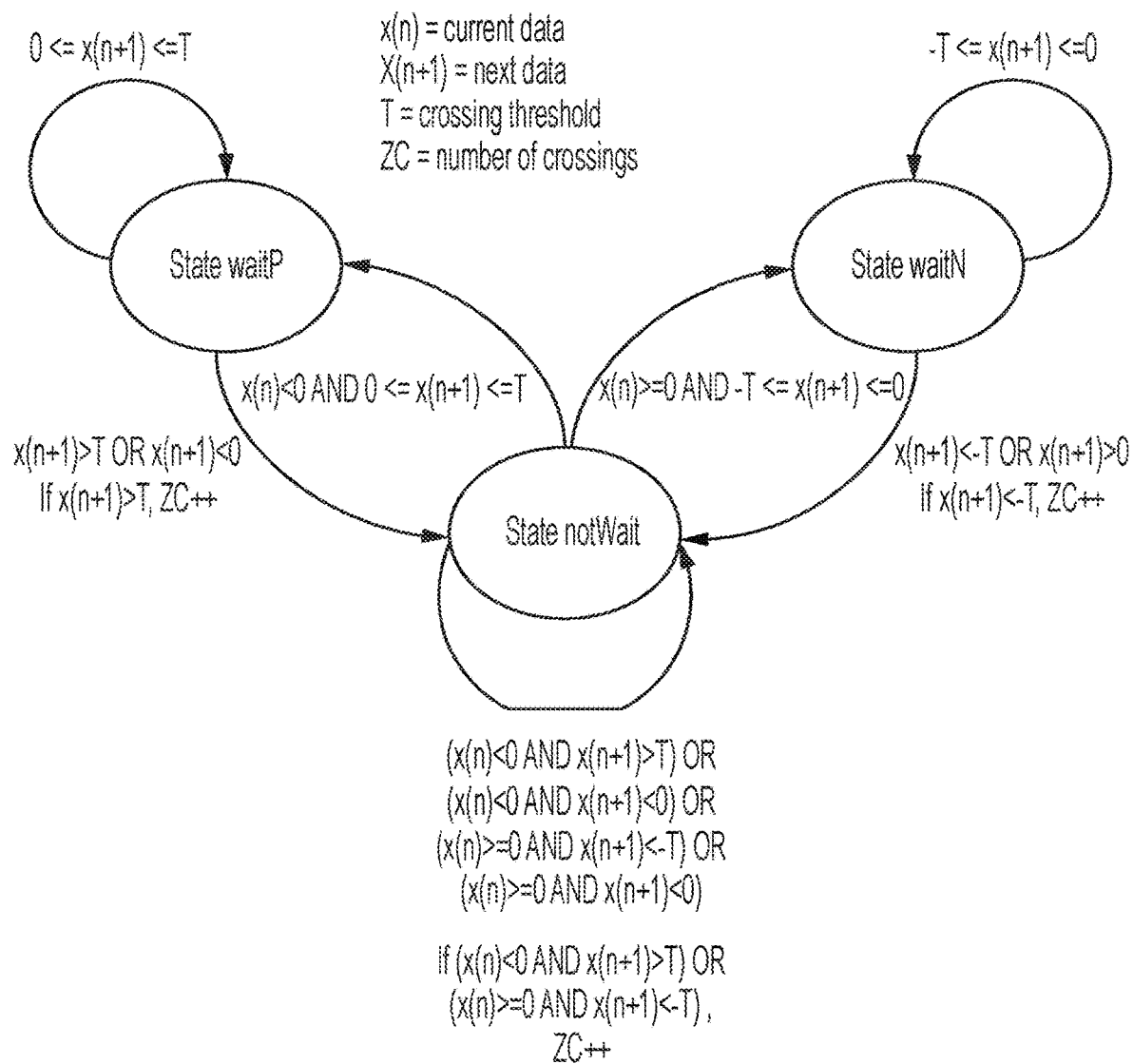
Figure 11C:
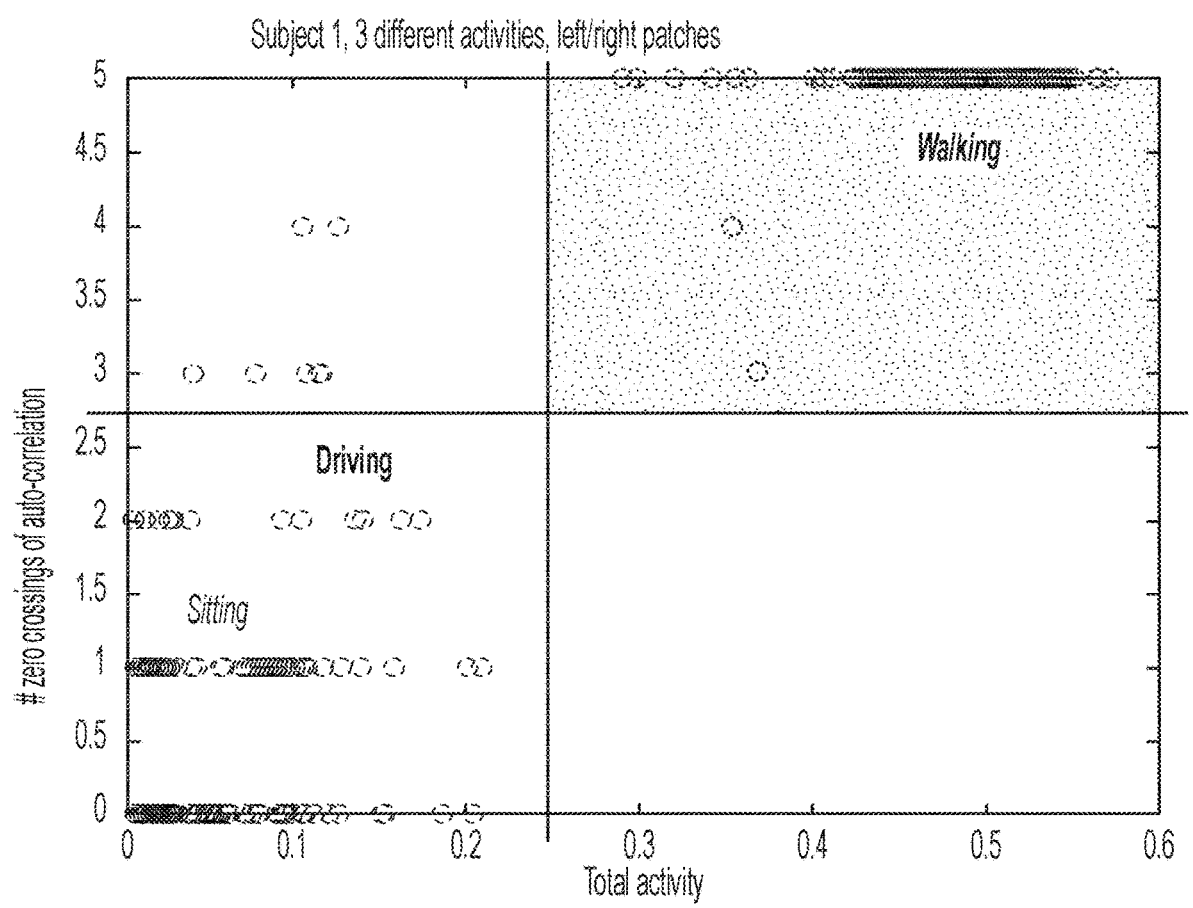
Figure 12B:
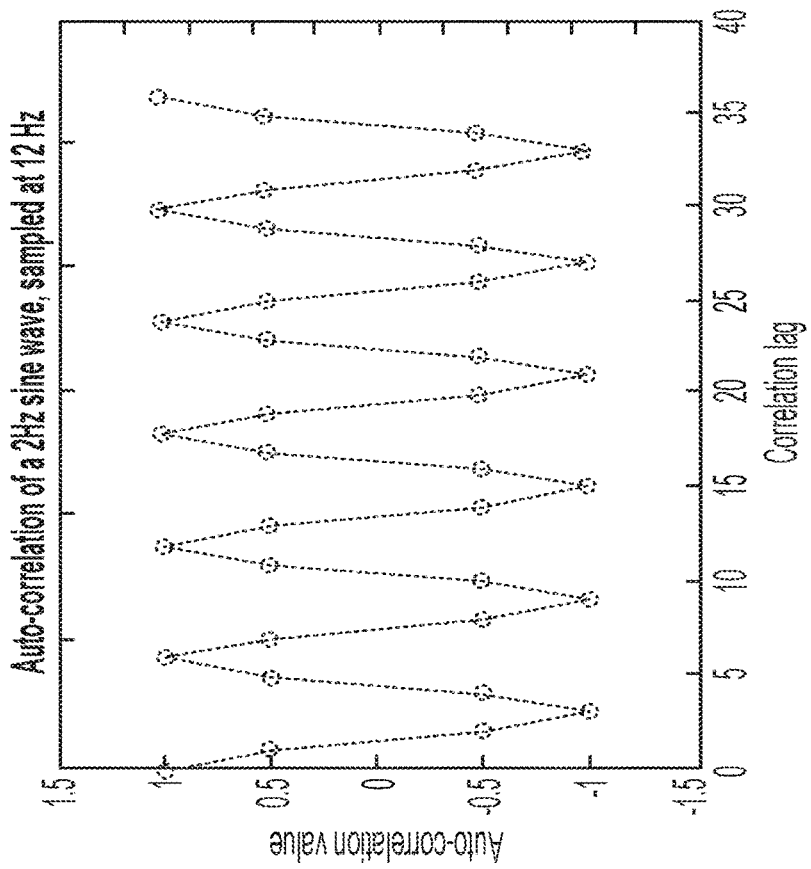
Figure 12A:
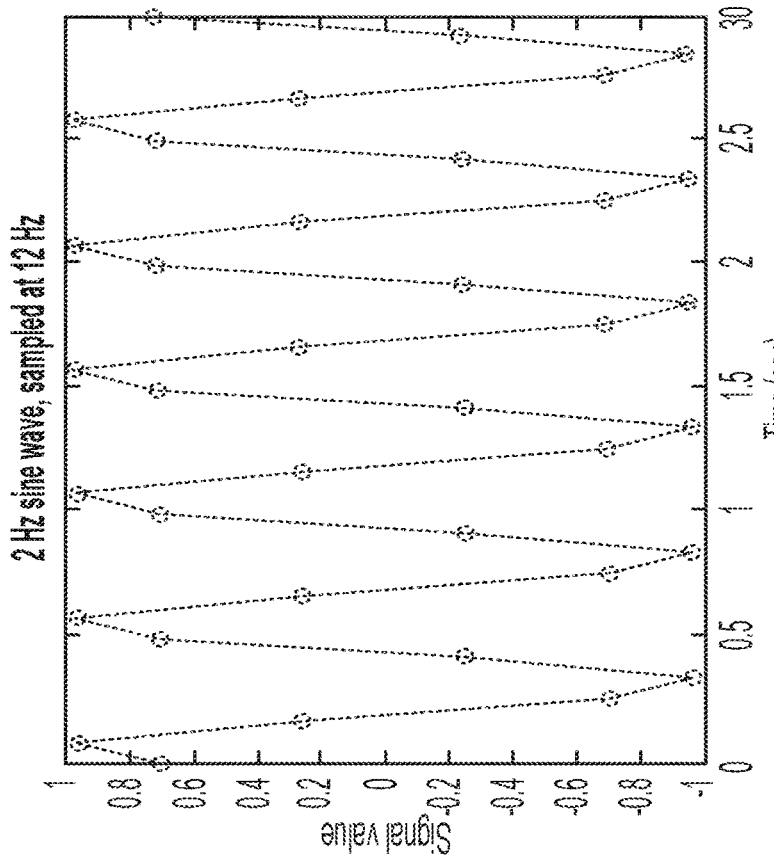
Figure 13B:
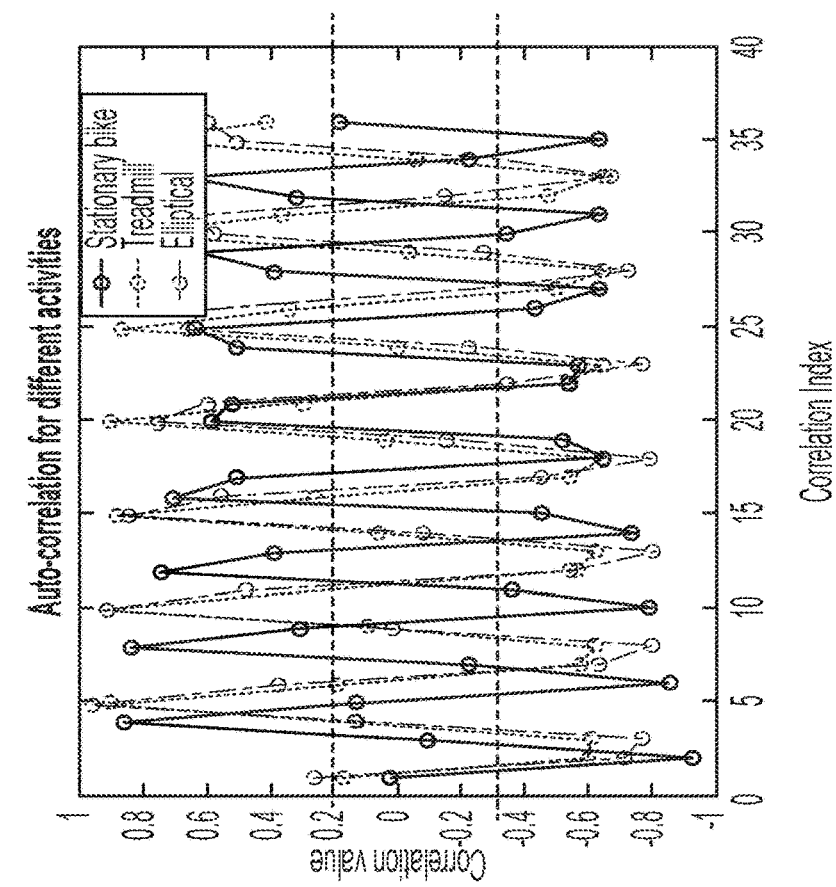
Figure 13A:
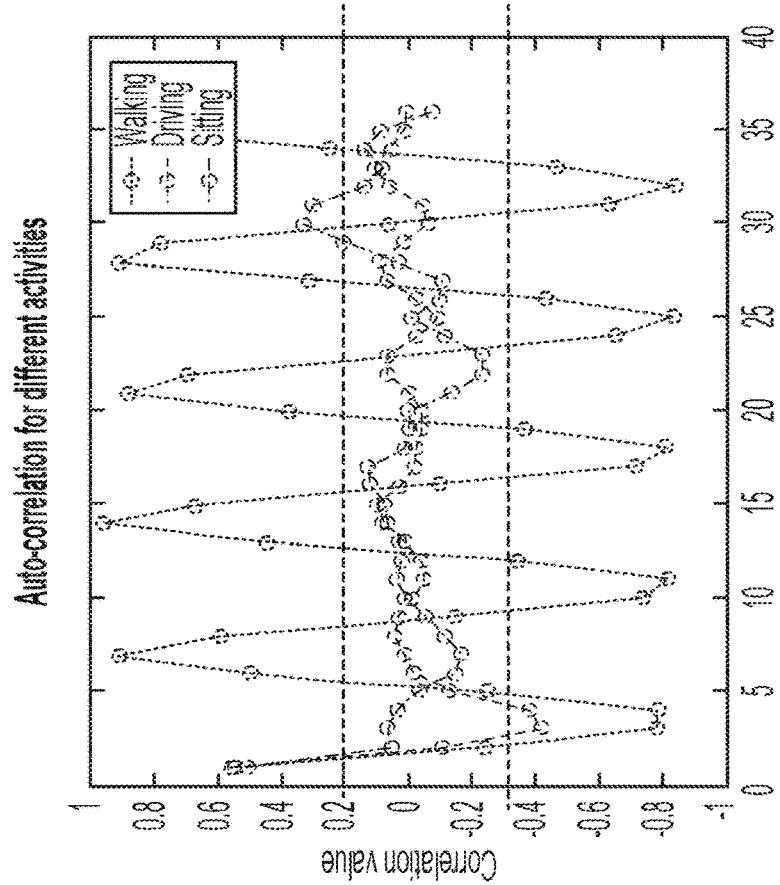
Figure 14:
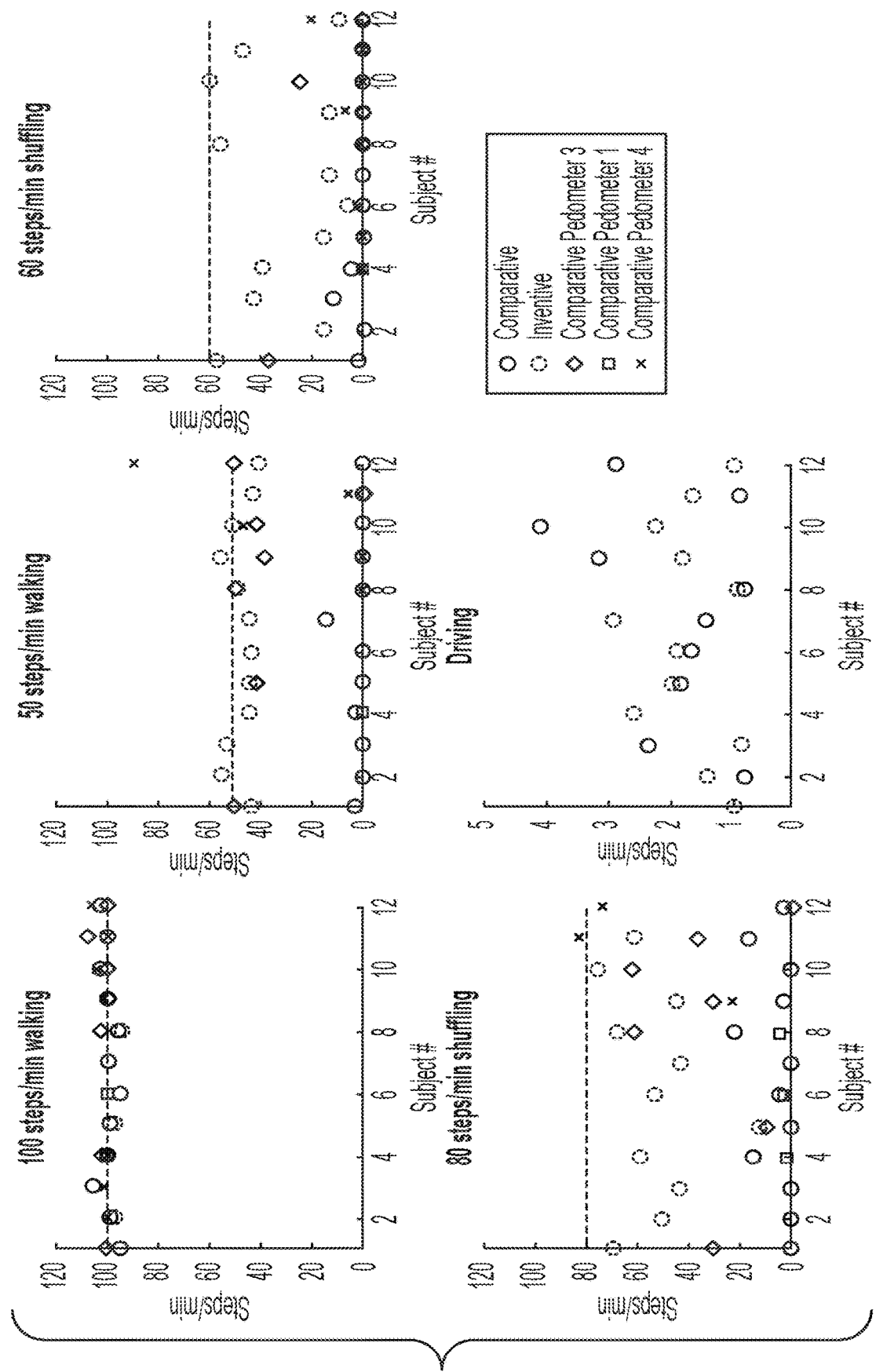
Figure 15:
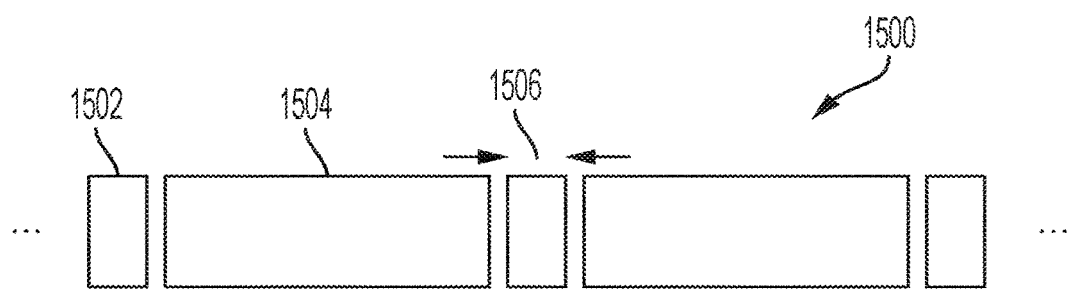
Figure 16:
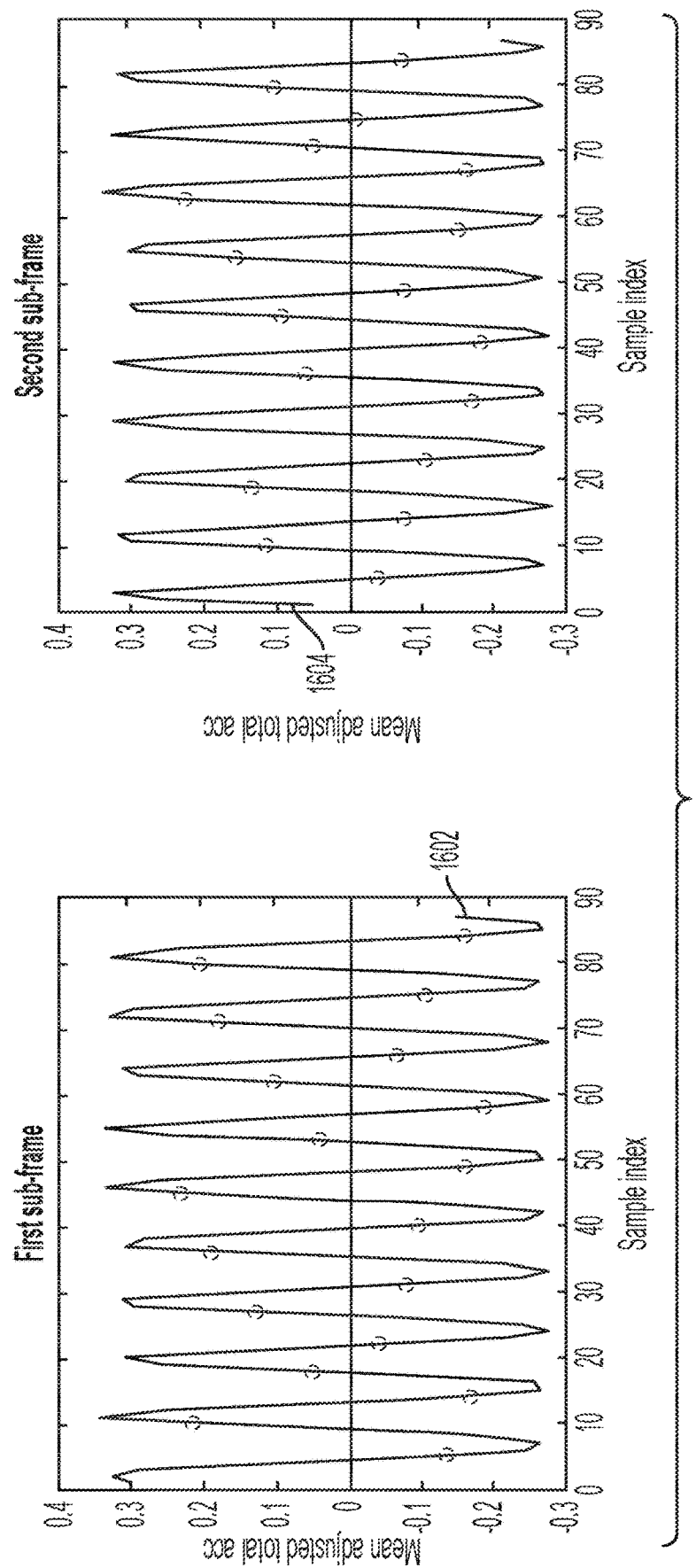
Figure 17:
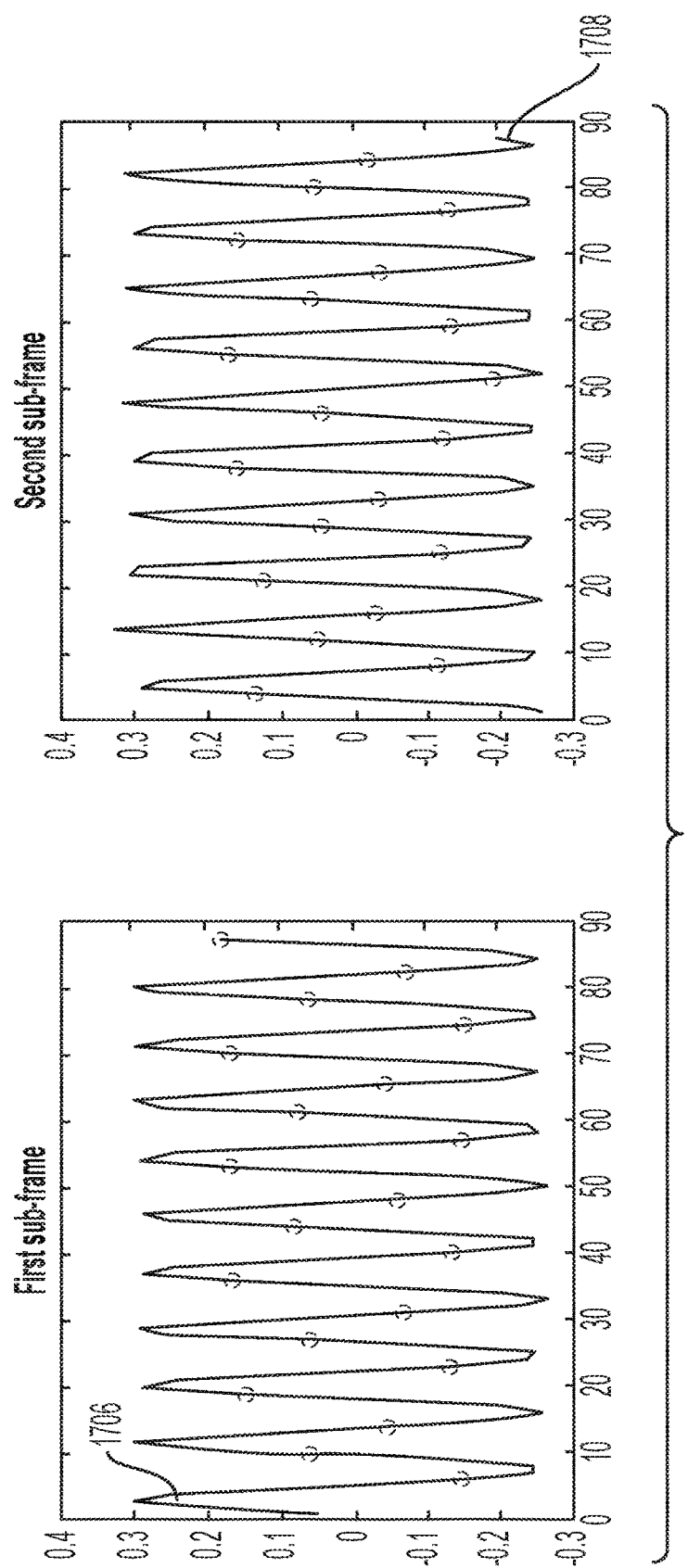
Figure 18:
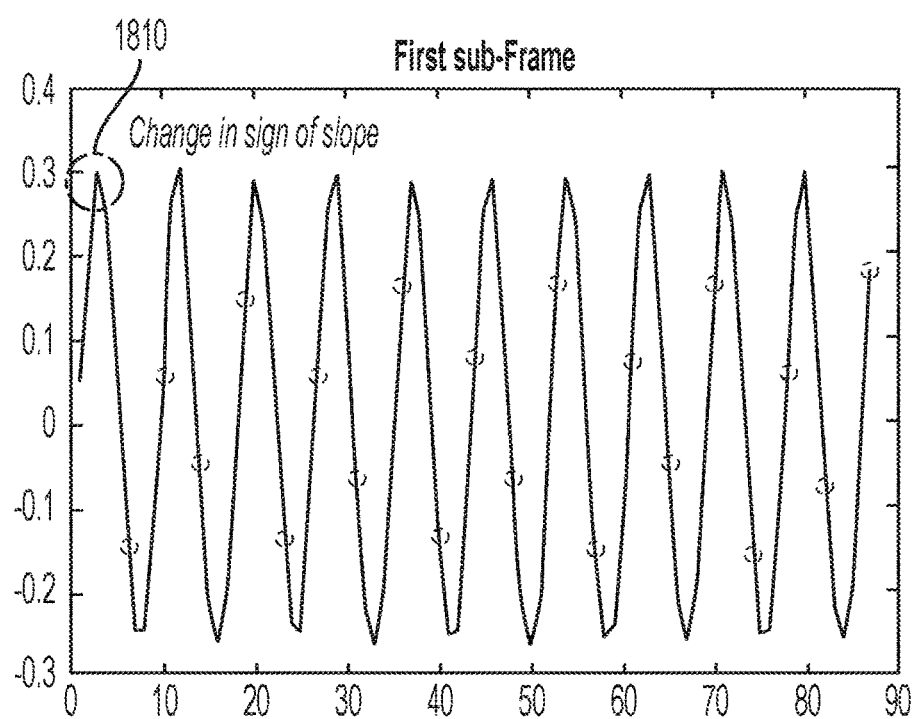
Figure 19:
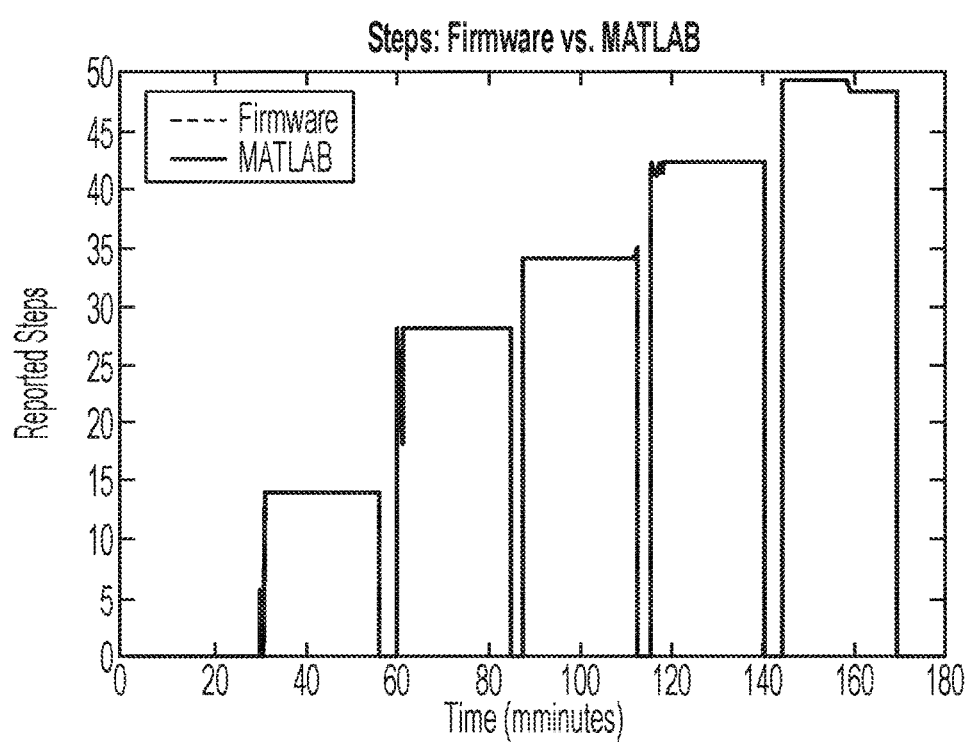
Figure 20A:
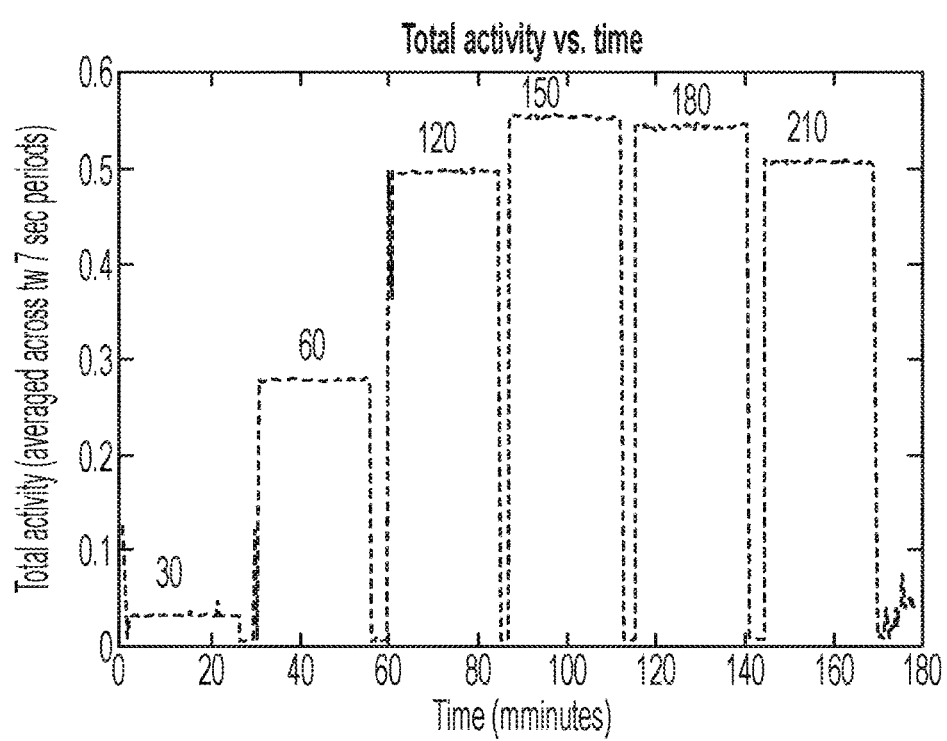
Figure 20B:
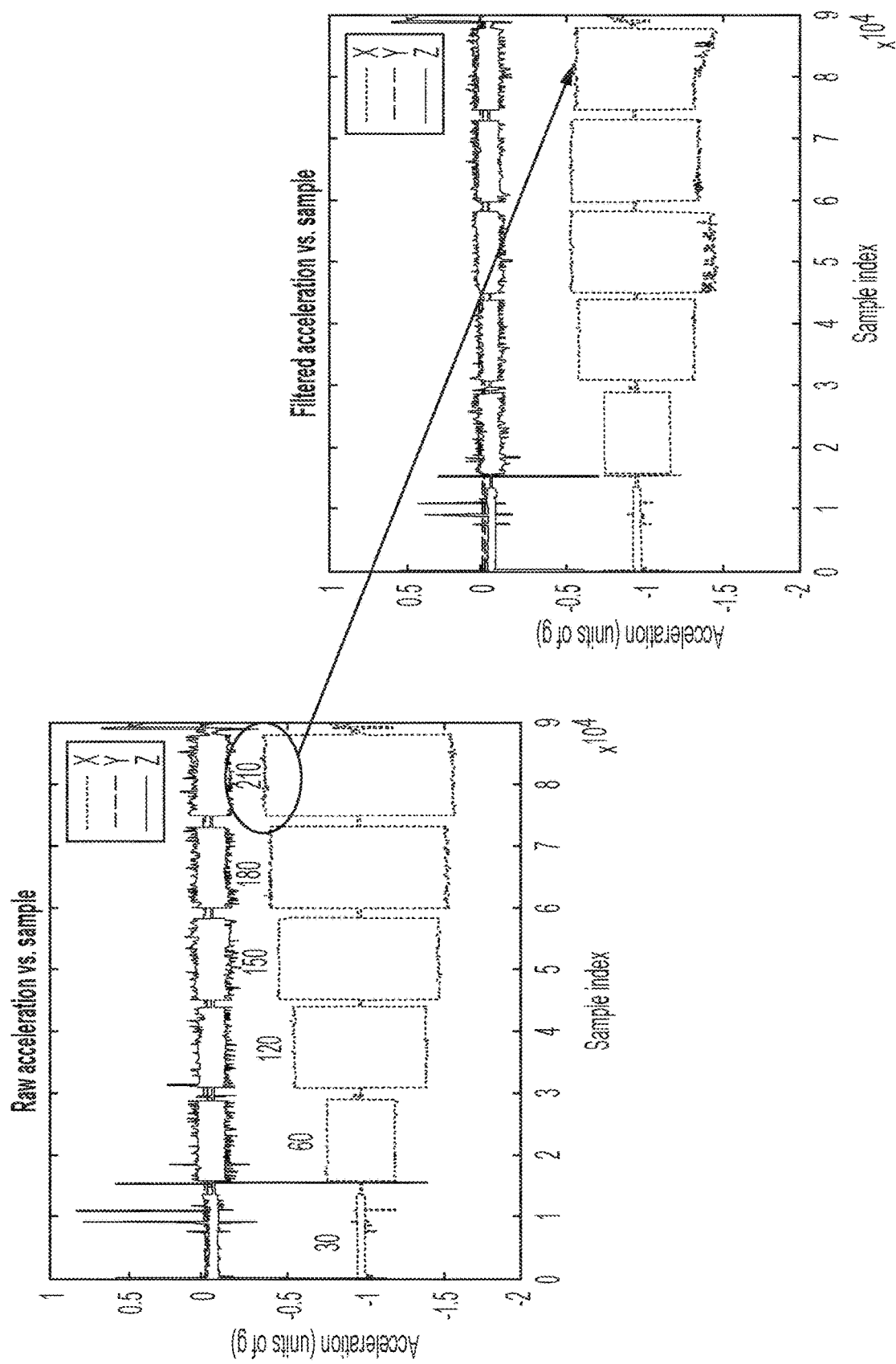
Figure 23:
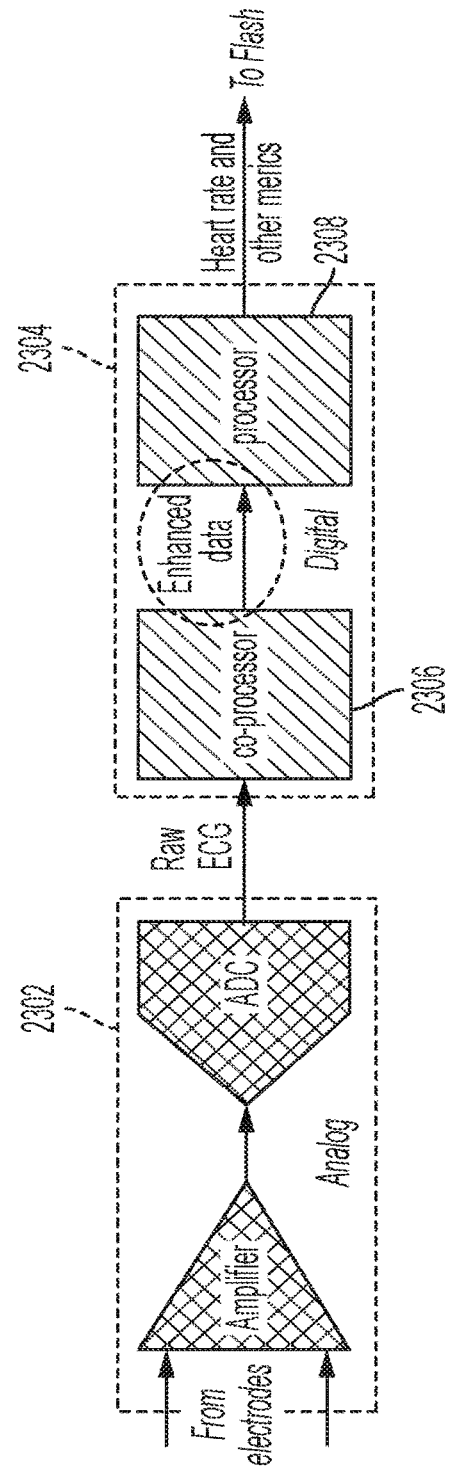
Figure 24:
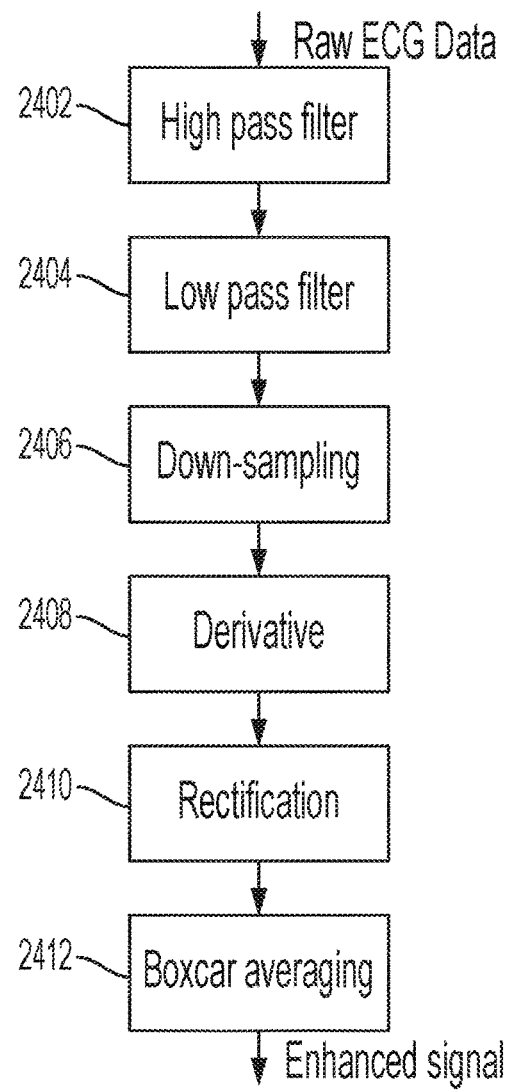
Figure 25:
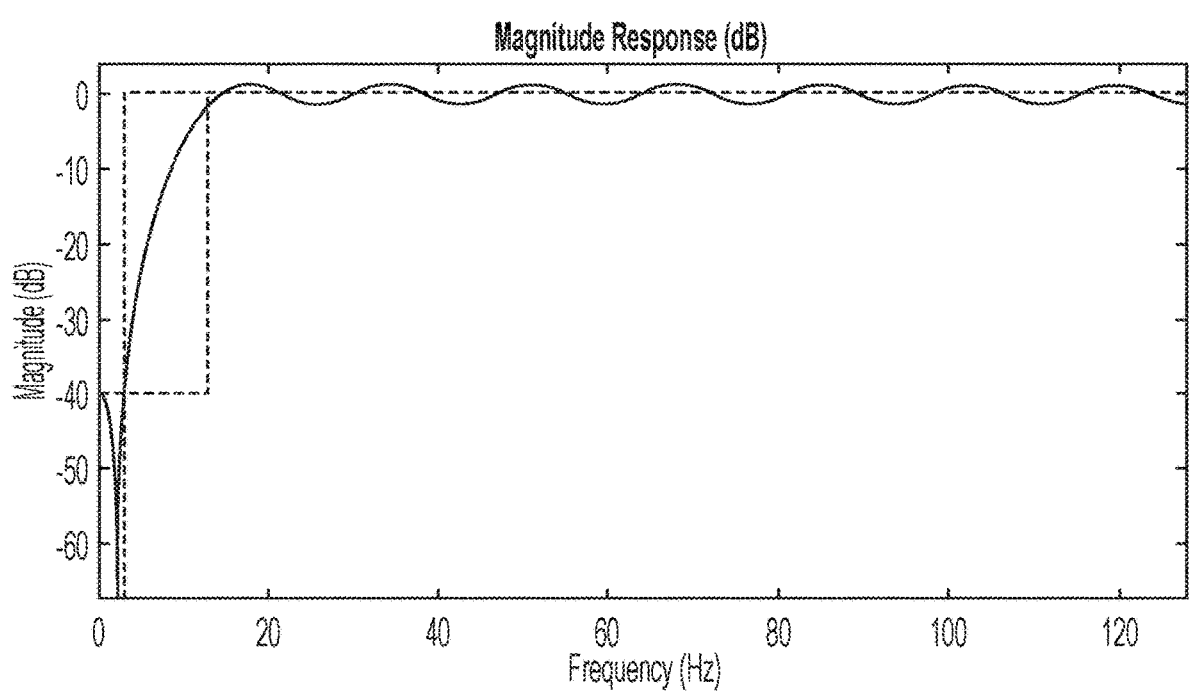
Figure 26:
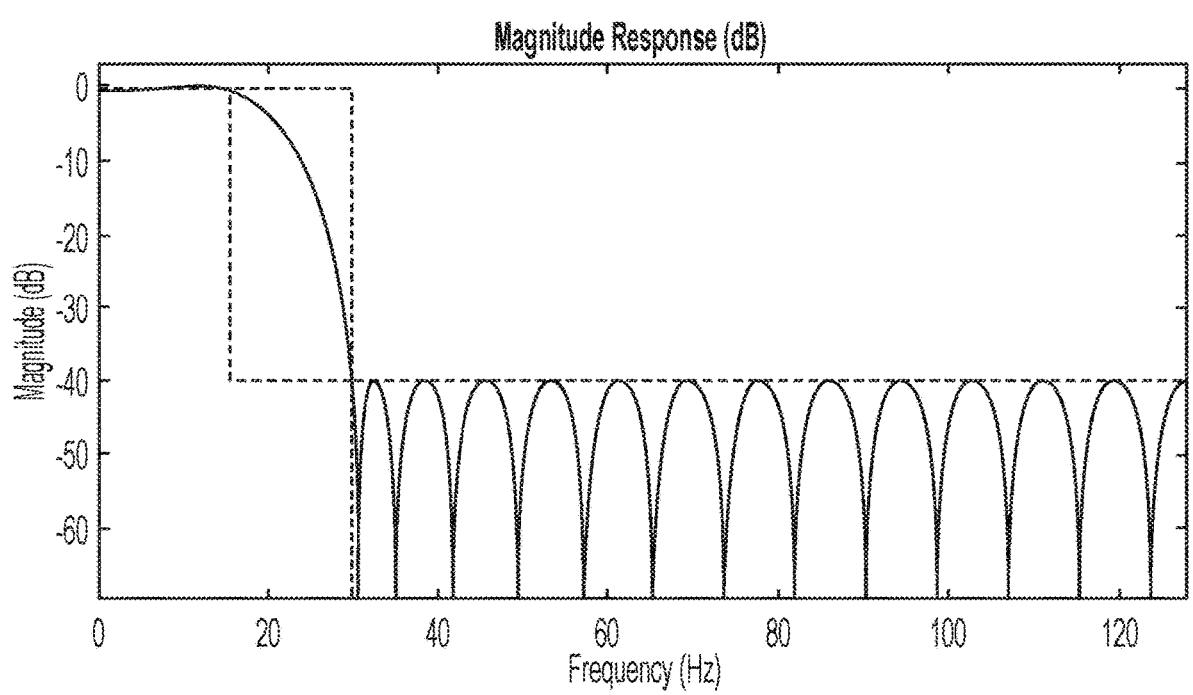
Figure 27:
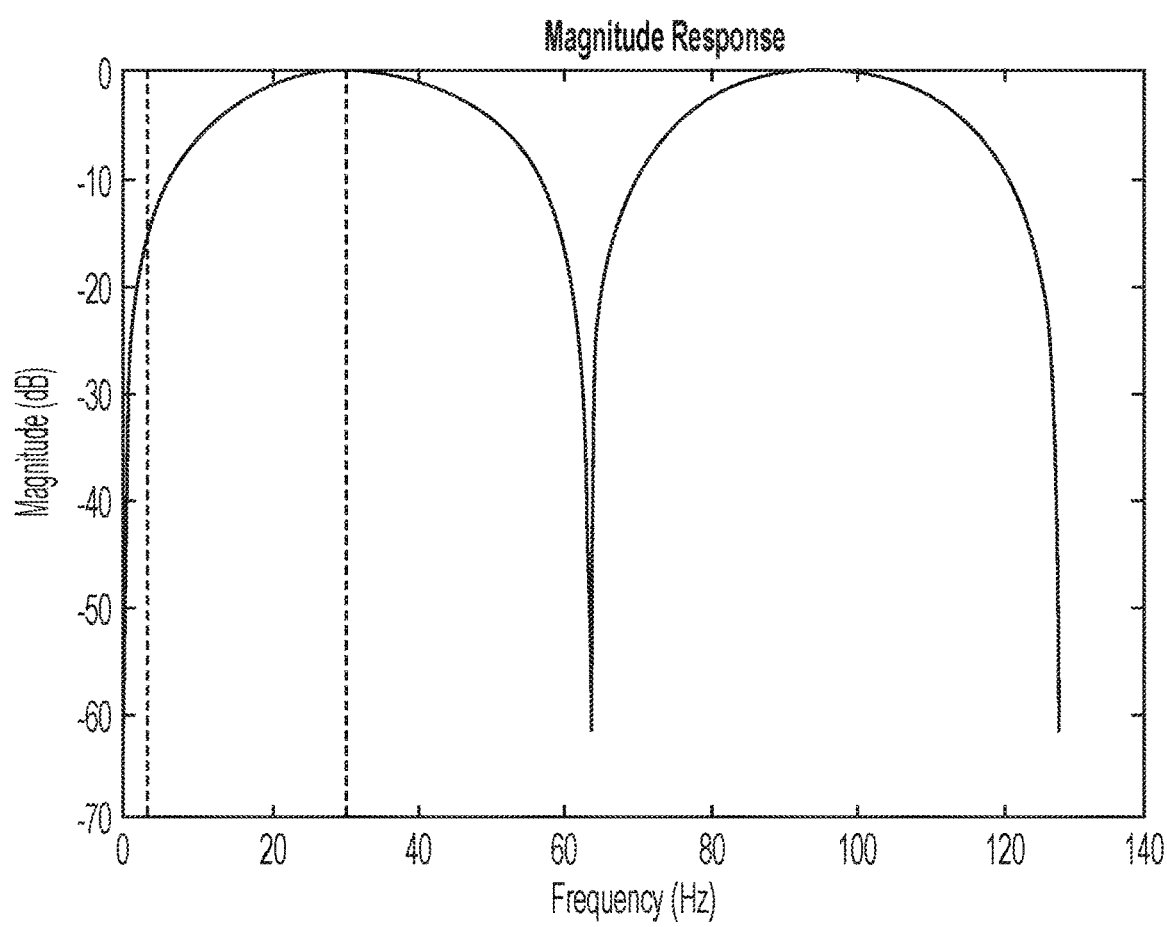
Figure 28:
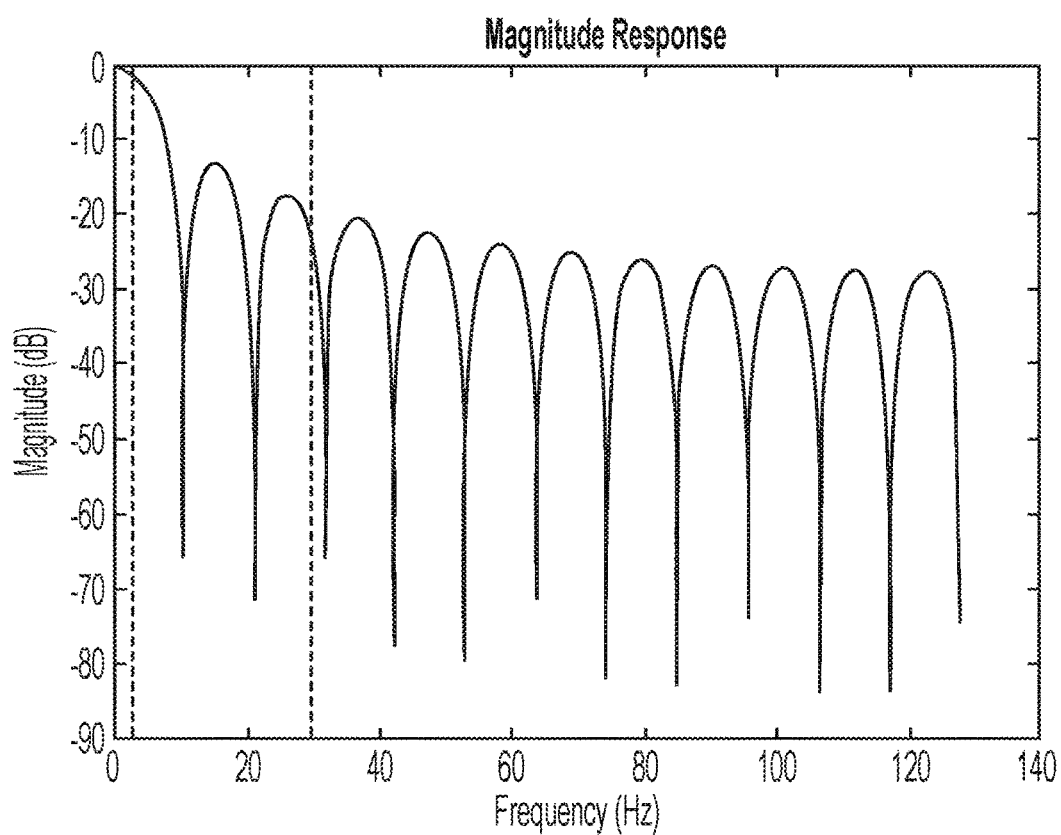
Figure 31:
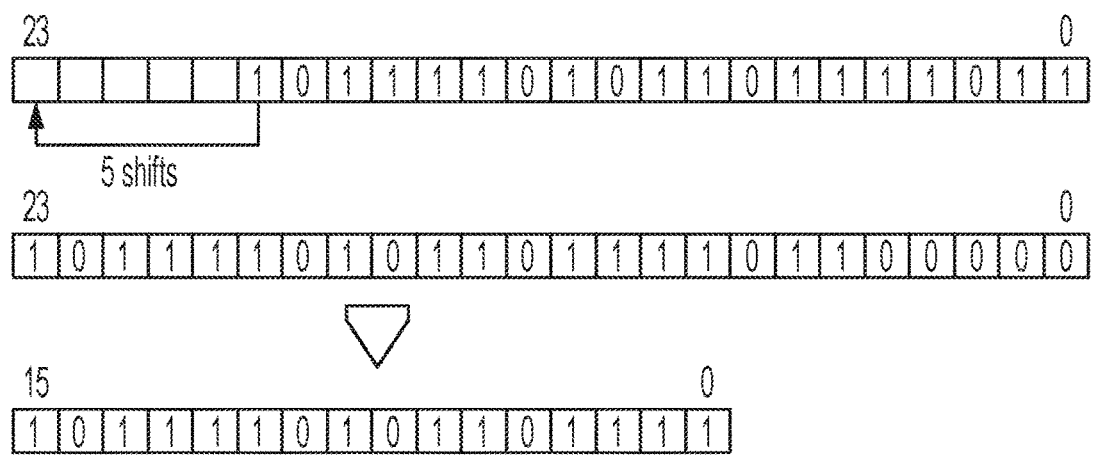
Figure 32:
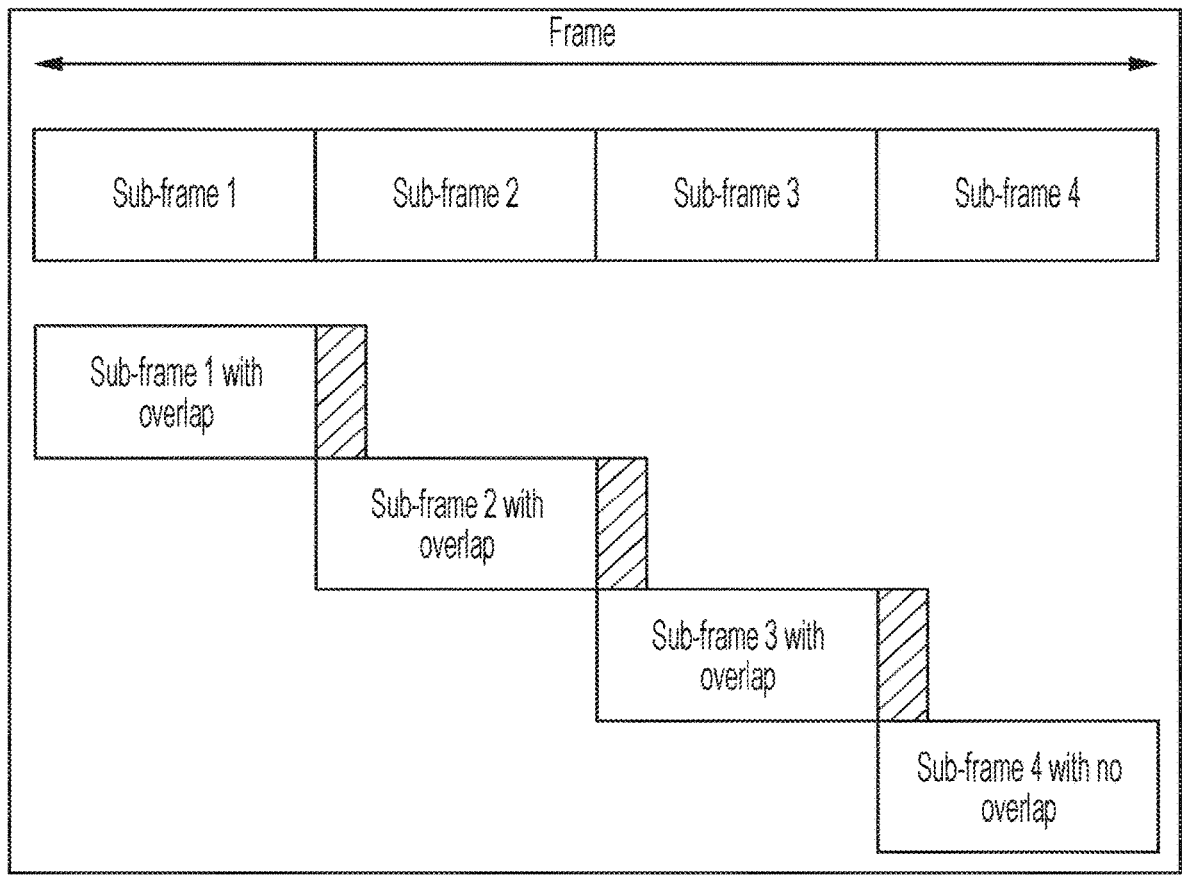
Figure 33:
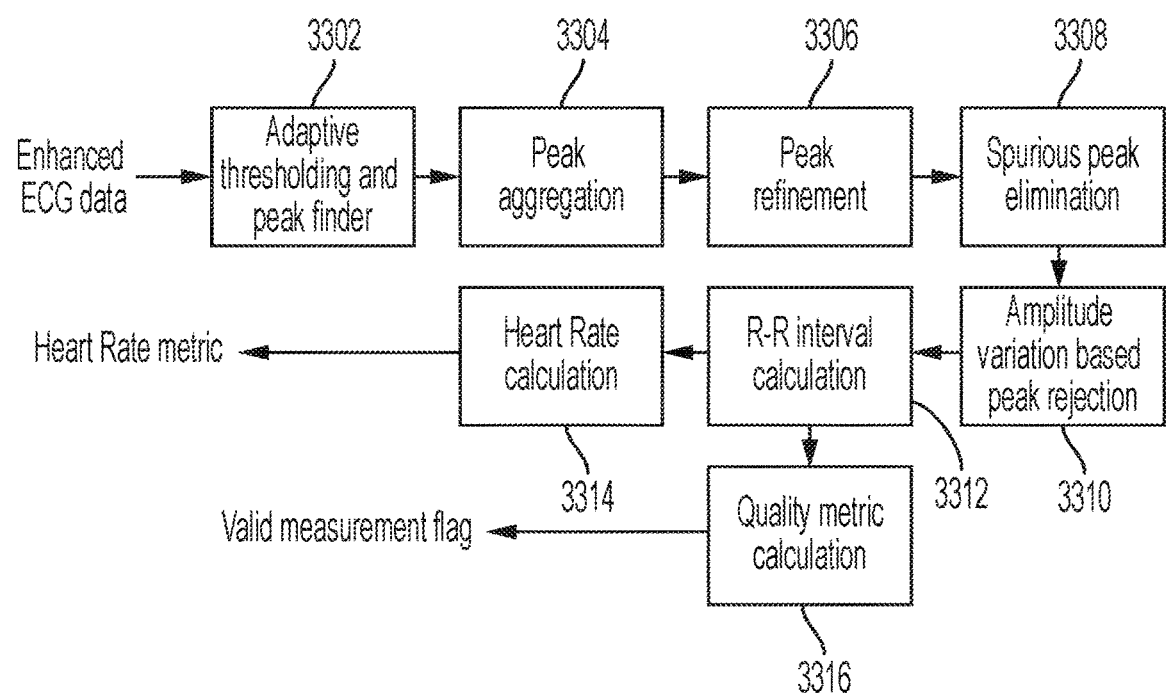
Figure 34:
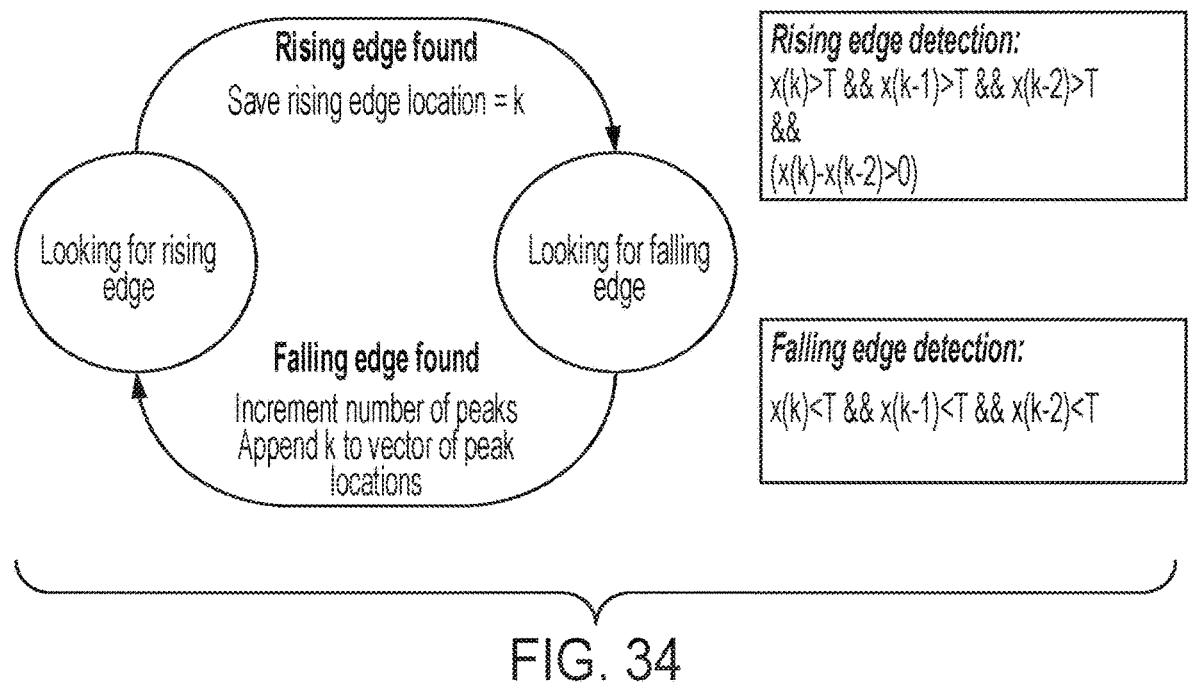
Figure 35A:
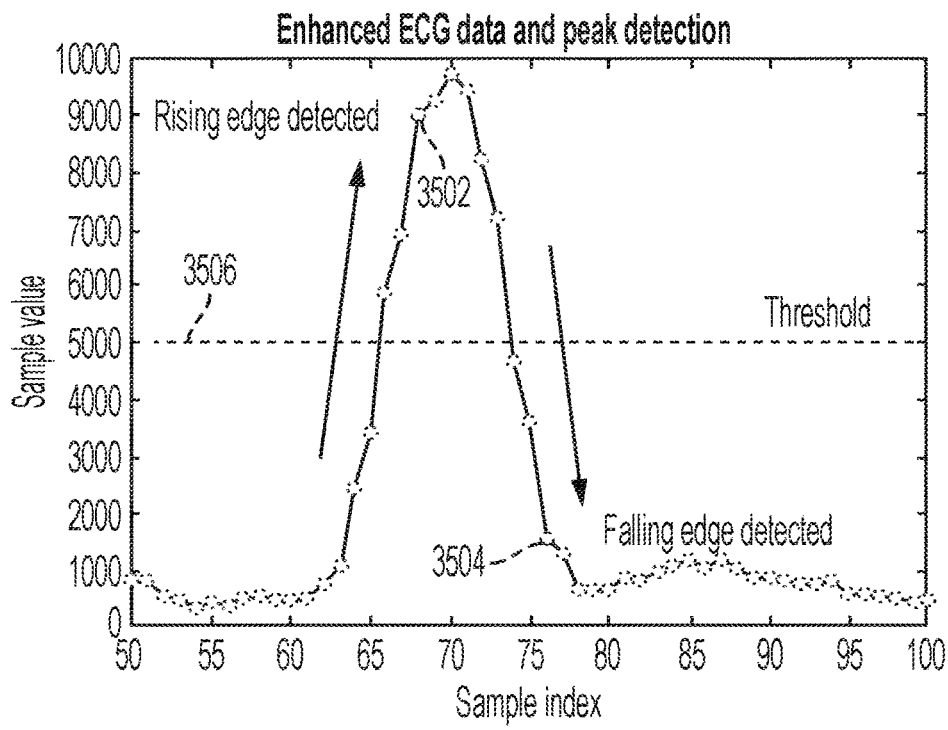
Figure 35B:
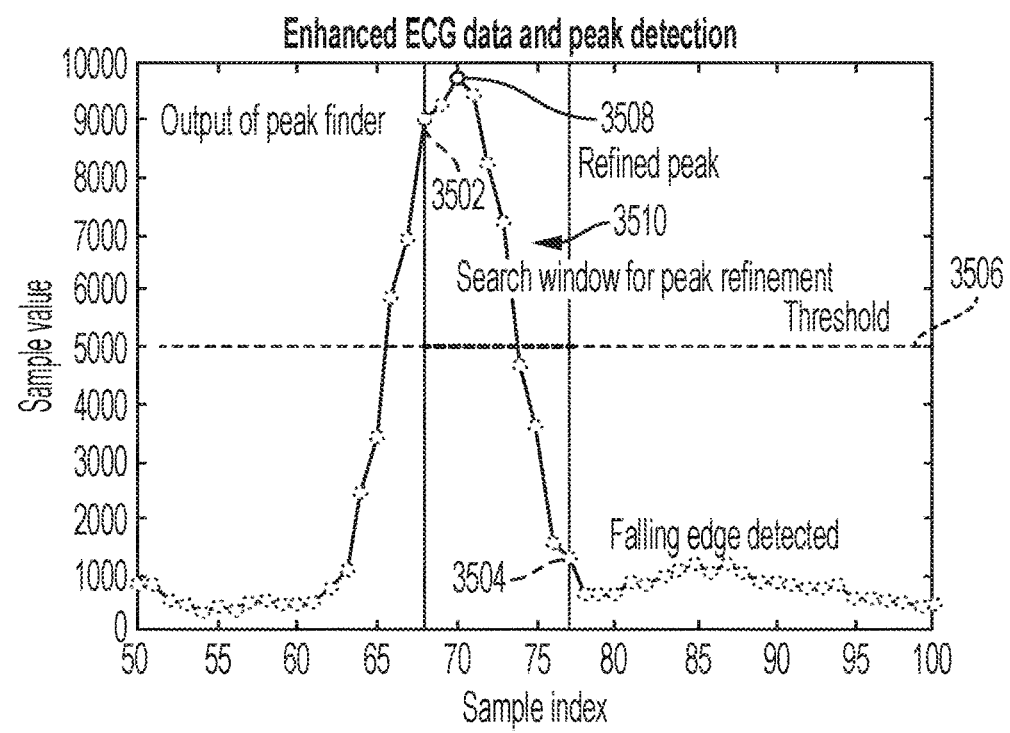
Figure 37:
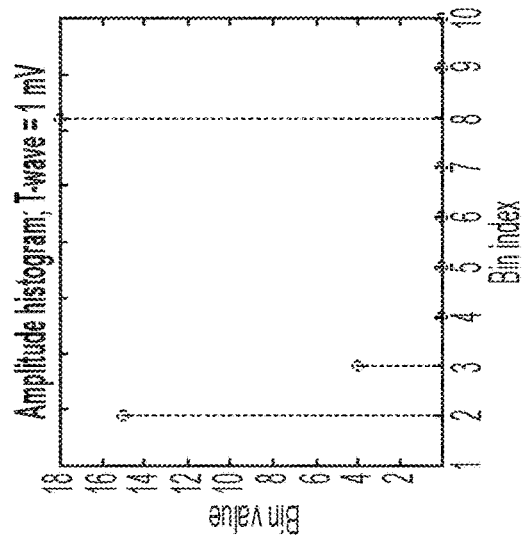
Figure 38:
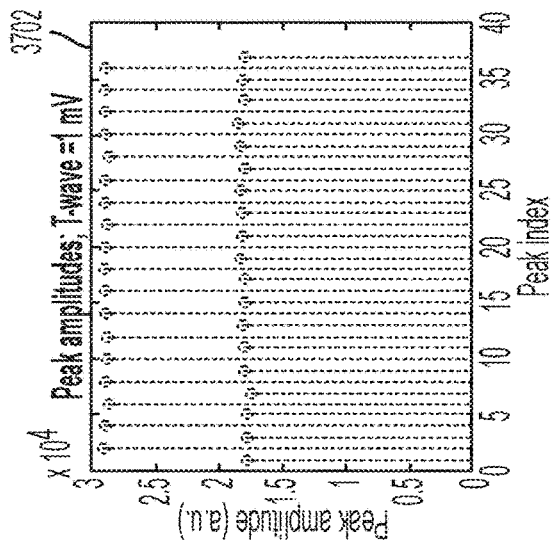
Figure 39:
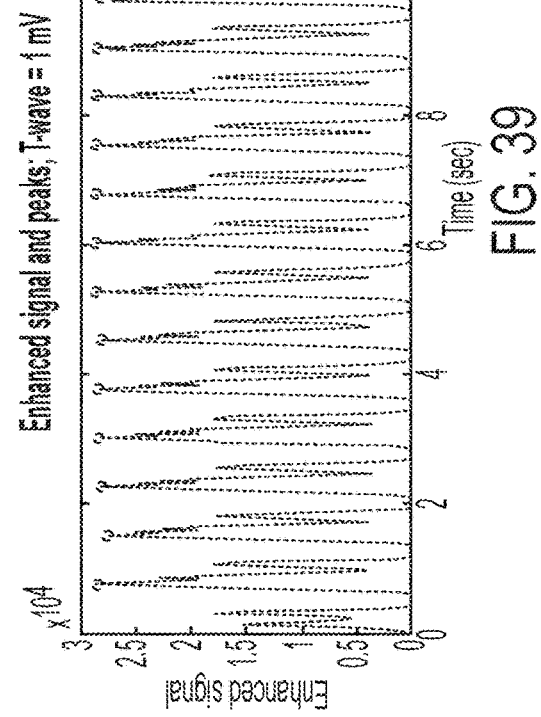
Figure 40:
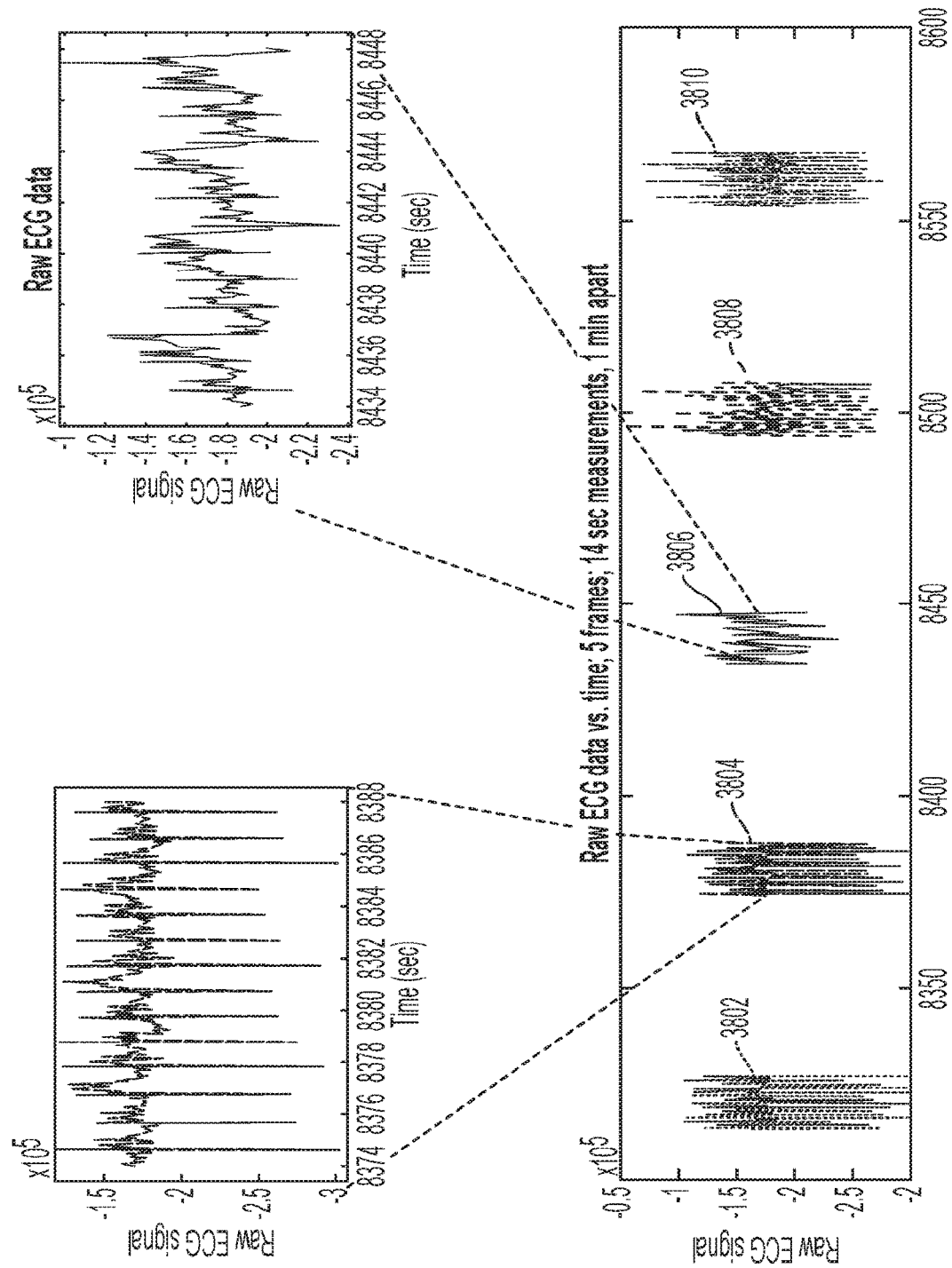
Figure 41:
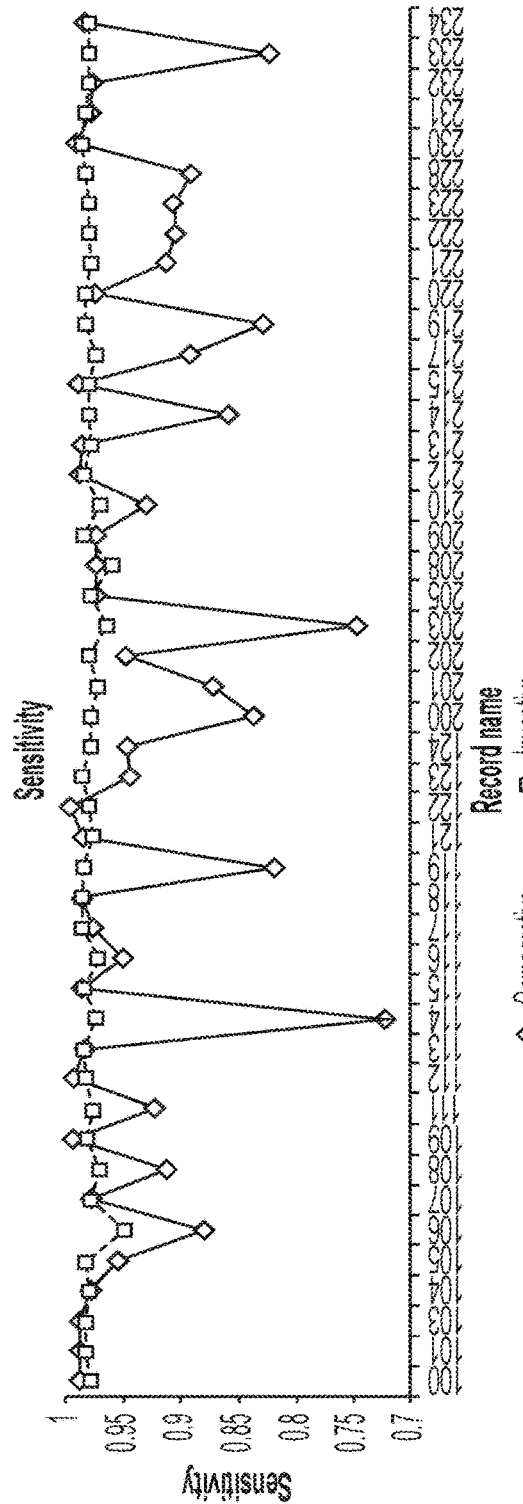
Figure 42:
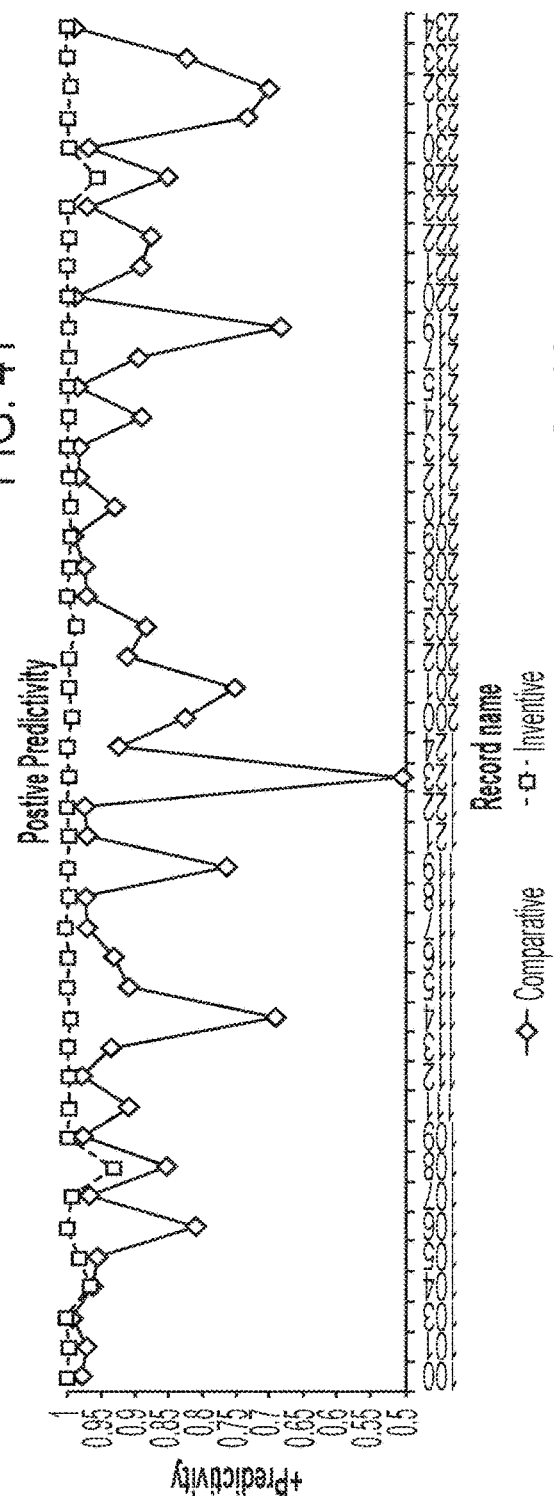
Figure 43A:
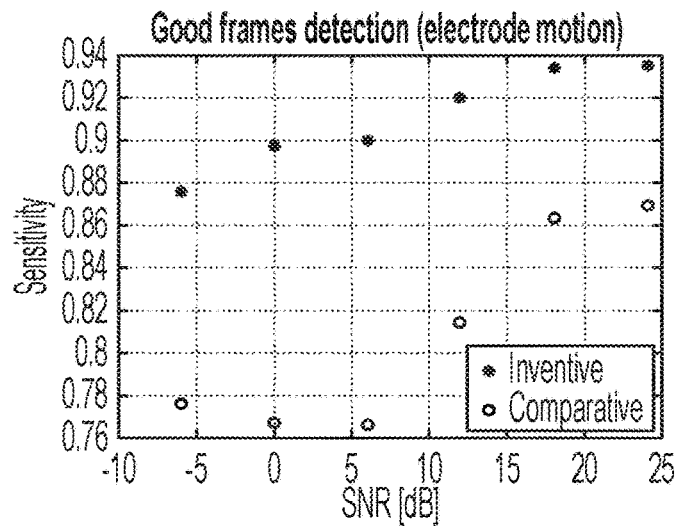
Figure 43B:
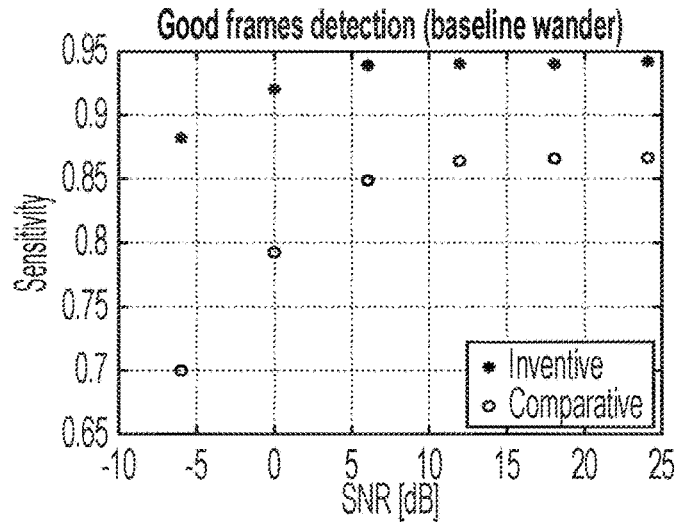
Figure 43C:
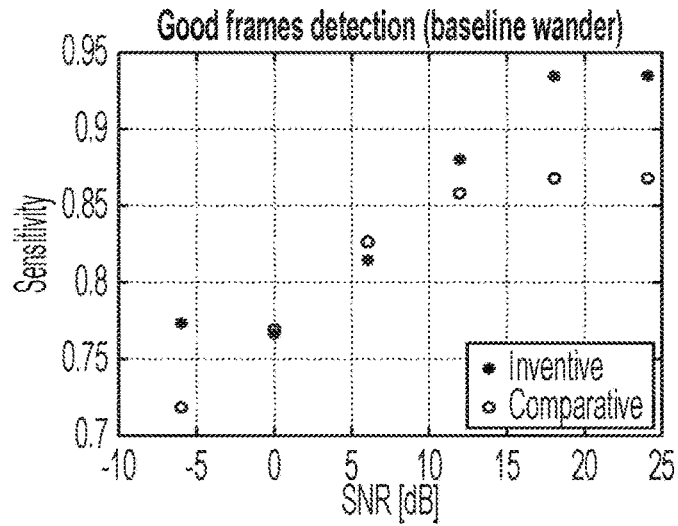
Figure 46:
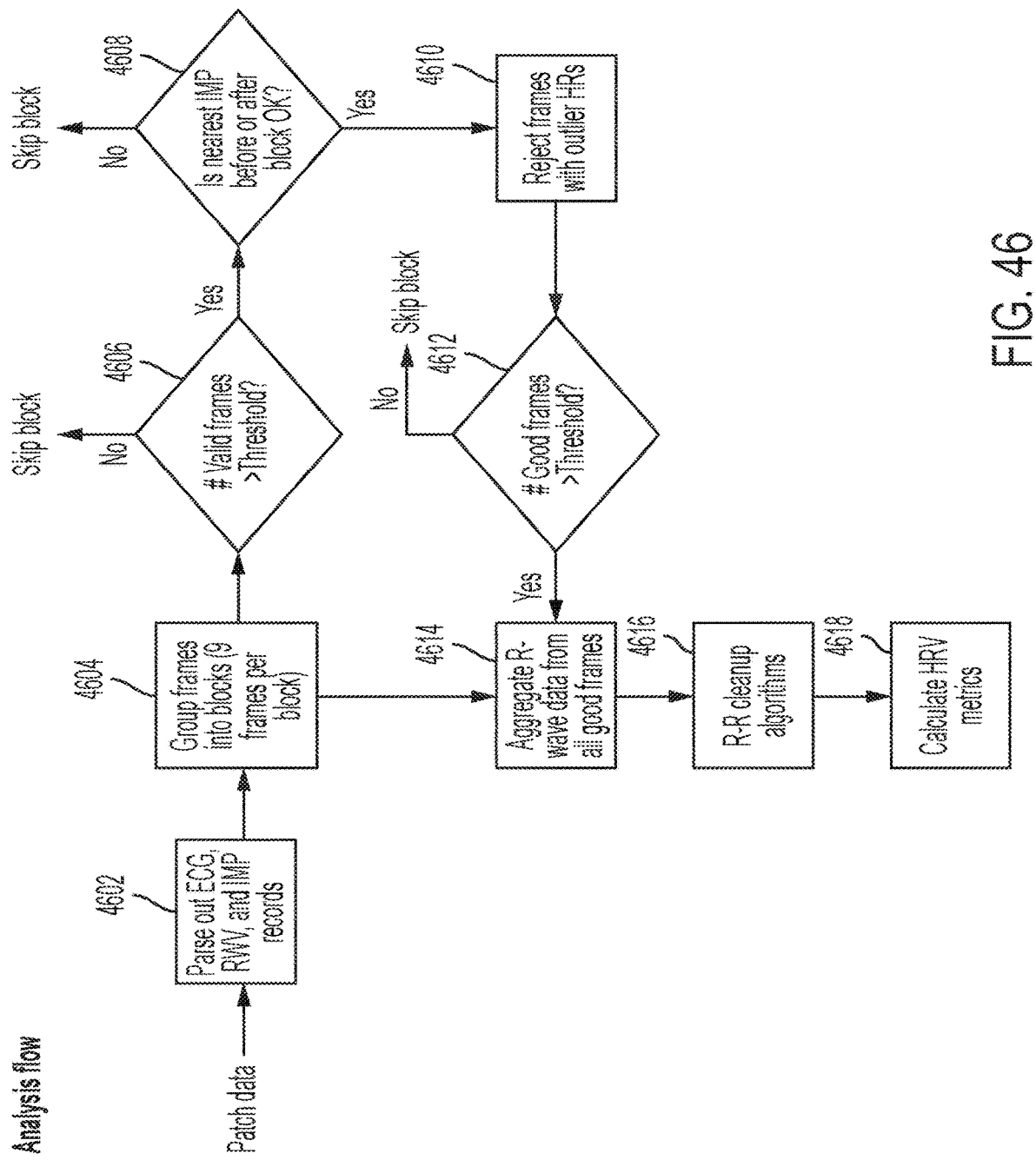
Figure 47:
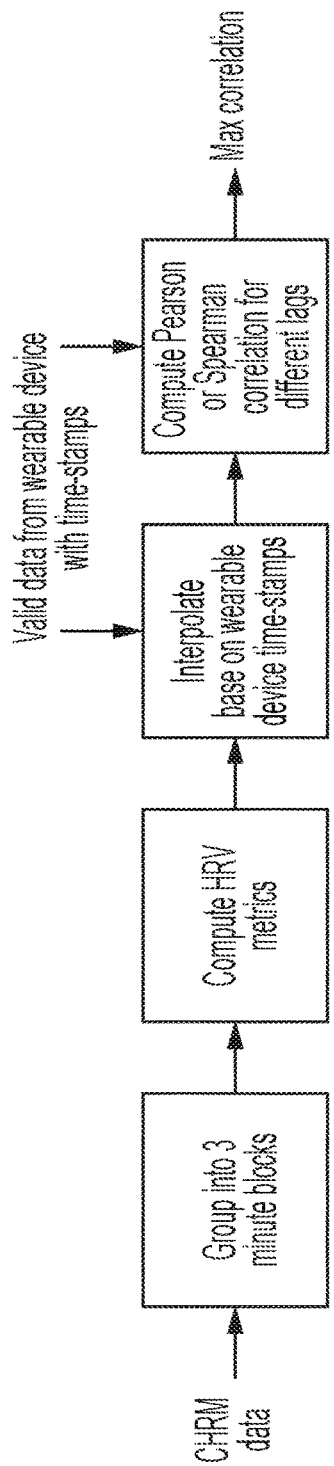
Figure 48:
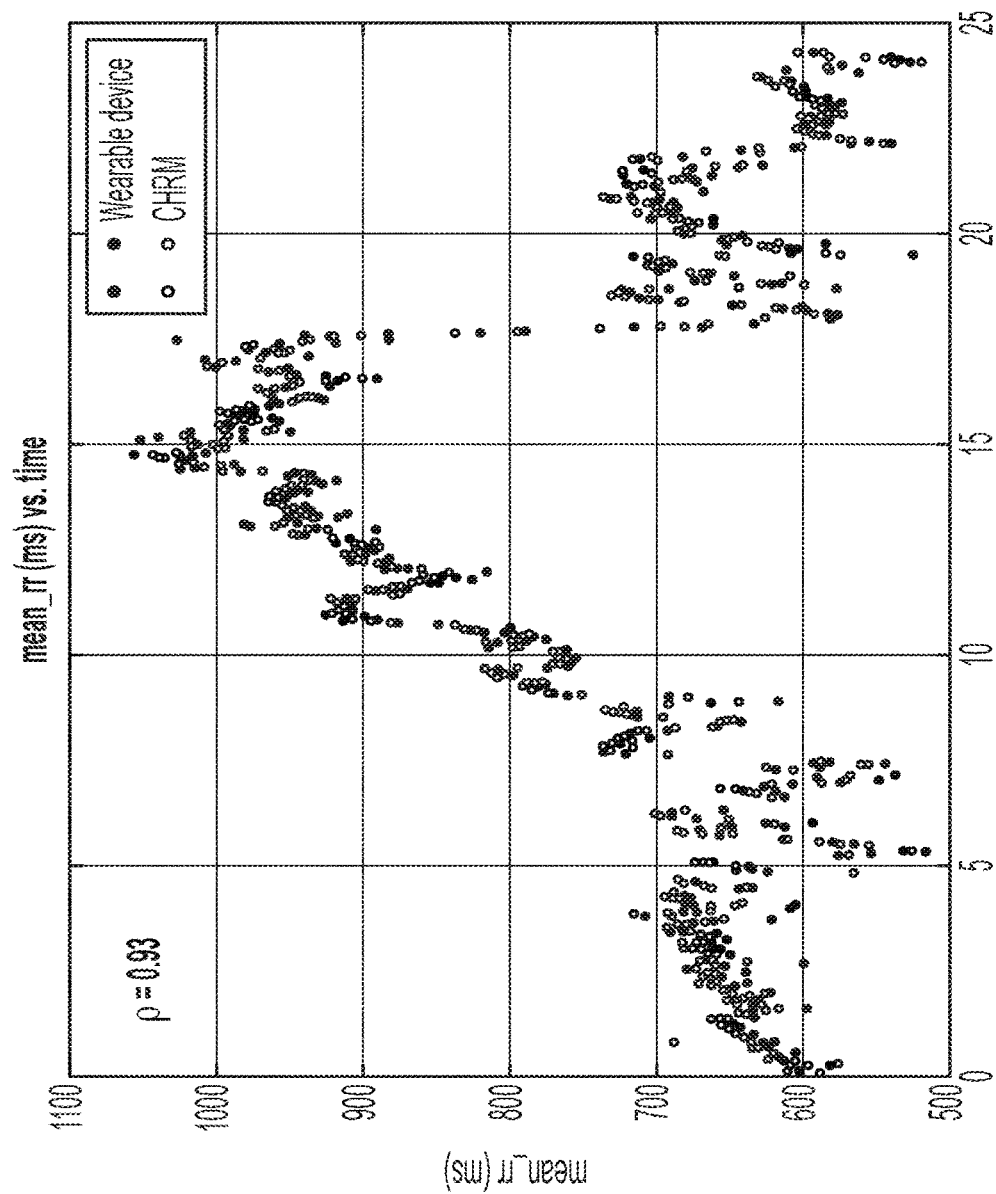
Figure 49:
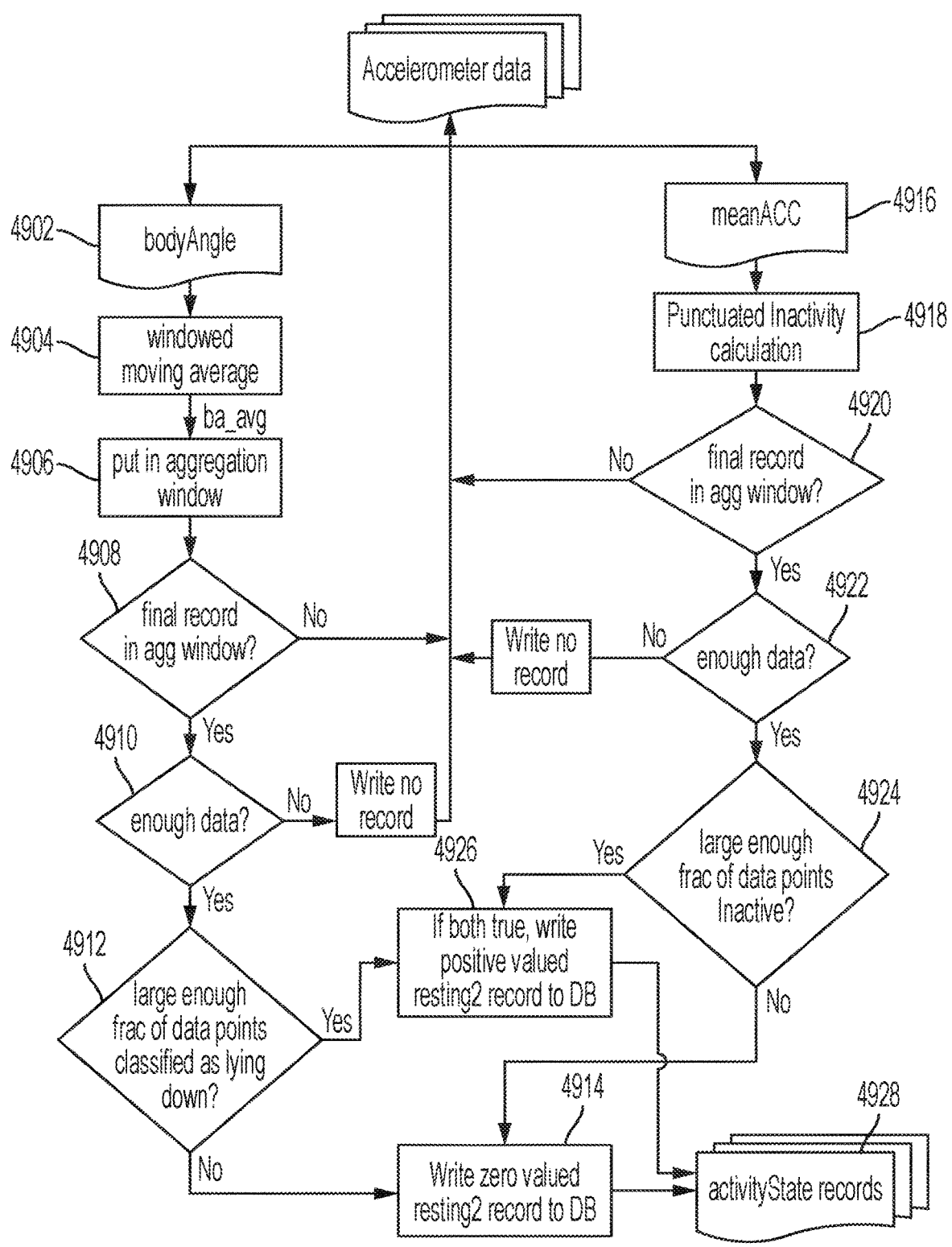
Figure 50:
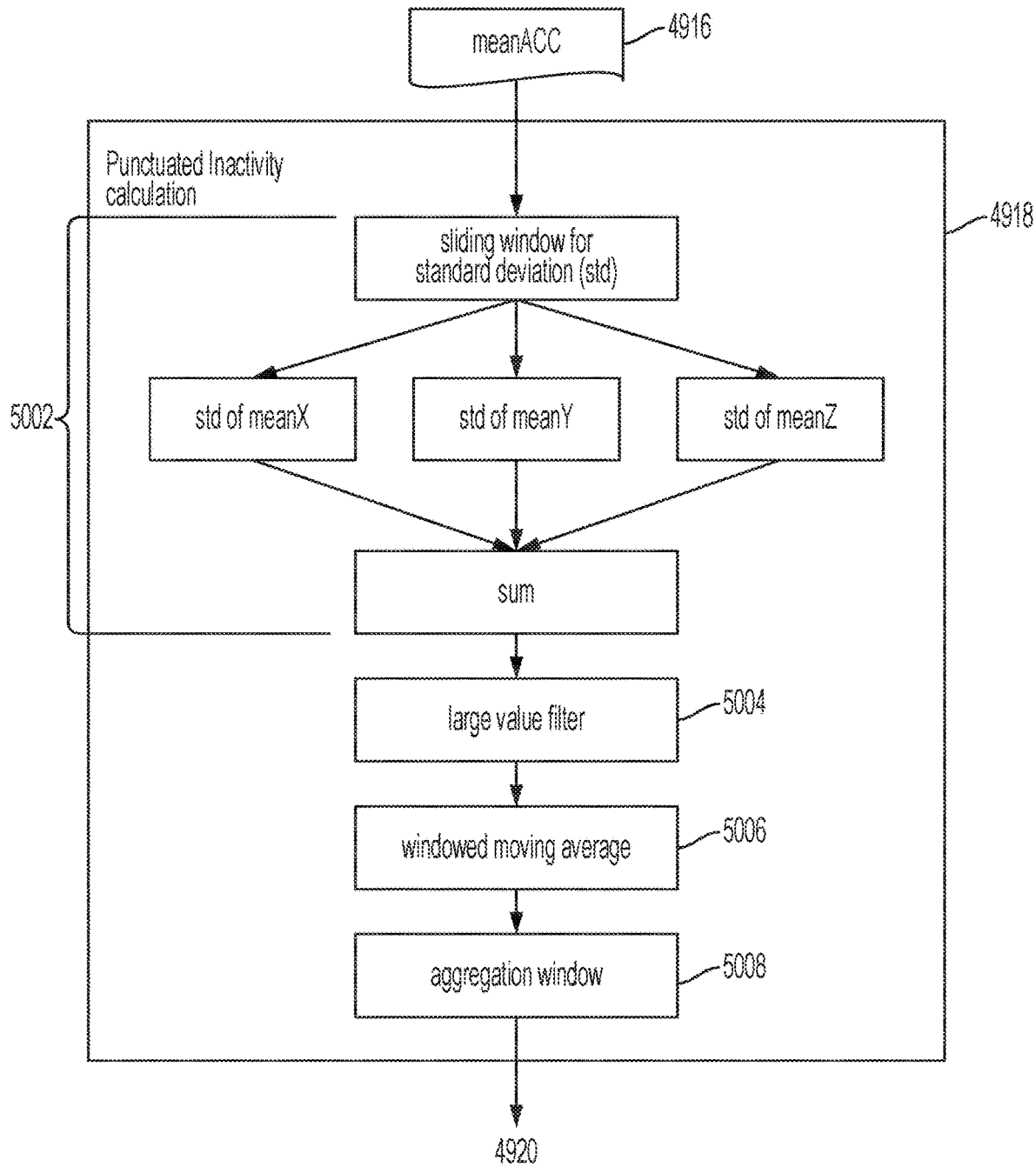

FIGS. 4A-E illustrate various types of analysis of accelerometer data by a comparative algorithm;

FIG. 5 illustrates a plot of accelerometer data as analyzed by a comparative algorithm;

FIG. 6 is a flow chart illustrating determination of a step count from accelerometer data according to the present disclosure;

FIGS. 7A-B are a flow chart illustrating determination of a step count from two blocks of accelerometer data according to the present disclosure;

FIG. 8 is a plot illustrating enhancement of accelerometer data to determine whether steps are being taken or if the accelerometer data is indicative of other activity according to the present disclosure;

FIG. 9 is a block diagram of a state machine for determining level crossing according to the present disclosure;

FIGS. 10A-E illustrate various types of analysis of accelerometer data by a comparative algorithm and a step count algorithm according to the present disclosure;

FIGS. 11A-C are plots of accelerometer data with adjusted threshold according to the present disclosure;

FIG. 12A is a plot of acceleration data produced from walking and FIG. 12B is a plot of auto-correlated data produced from the acceleration data of FIG. 12A according to the present disclosure;

FIGS. 13A-B are plots of auto-correlation data for various activities according to the present disclosure;

FIG. 14 illustrates a plot of reported steps count rates of various patients as output by various pedometers and the wearable device comprising a comparative algorithm and the step count algorithm according to the present disclosure;

FIG. 15 is a block diagram of discontinuous data according to the present disclosure;

FIG. 16 is plots of sub-frames of accelerometer data according to the present disclosure;

FIG. 17 is plots of sub-frames of accelerometer data illustrating boundary effects;

FIG. 18 illustrates a sub-frame of accelerometer data illustrating a slope change;

FIG. 19 illustrates the step count values output from the step count algorithm processed on processor of the wearable device and a MATLAB model post-processing raw accelerometer data from the wearable device on a remote device according to the present disclosure;

FIG. 20A is a plot of total activity data and FIG. 20B is a plot of acceleration data before and after box car filtering;

FIGS. 21A-D are block diagrams illustrating generation of a reference vector by filling bins with ACRs according to the present disclosure;

FIG. 22A is plots of heart rate data illustrating large blocks of missing data, FIG. 22B is a plot of body angle over time corresponding to the data in FIG. 22A, and FIG. 22C is a plot of raw ECG data that was ignored by a previous comparative algorithm;

FIG. 23 is a flow chart illustrating receiving and processing of ECG data according to the present disclosure;

FIG. 24 is a flow chart illustrating enhancement of ECG data according to the present disclosure;

FIG. 25 is a plot illustrating the magnitude response of a high-pass filter according to the present disclosure;

FIG. 26 is a plot illustrating the magnitude response of a low-pass filter according to the present disclosure;

FIG. 27 is a plot illustrating the magnitude response of a derivative filter according to the present disclosure;

FIG. 28 is a plot illustrating the magnitude of response for a boxcar filter according to the present disclosure;

FIGS. 29A-F are plots illustrating the transformation of raw ECG data to enhanced ECG data by the vector co-processor, including down-sampling, according to the present disclosure;

FIGS. 30A-G are plots illustrating the transformation of raw ECG data to enhanced ECG data by the vector co-processor according to the present disclosure;

FIG. 31 is a block diagram illustrating the normalization of ECG data according to the present disclosure;

FIG. 32 is a block diagram illustrating the partitioning of a buffer into sub-frames of a frame of ECG data according to the present disclosure;

FIG. 33 is a flow chart illustrating the processing of enhanced ECG data in the processor according to the present disclosure;

FIG. 34 is a block diagram illustrating the state machine for a peak finder algorithm according to the present disclosure;

FIGS. 35A-B are plots illustrating the peak finder algorithm and peak refinement according to the present disclosure;

FIGS. 36A-E are plots illustrating adaptive thresholding according to the present disclosure;

FIGS. 37-39 are plots illustrating T-wave rejection according to the present disclosure;

FIG. 40 is a plot of various ECG data according to the present disclosure;

FIG. 41 is a plot of sensitivity of the comparative algorithm and the HR algorithm according to the present disclosure;

FIG. 42 is a plot of positive predicitivity data of the comparative algorithm and the HR algorithm according to the present disclosure;

FIG. 43A-C are plots of the results of the sensitivity mean averaged over all 48 records in the MIT-BIH arrhythmia database with various added noise and the quality filters turned on in the HR algorithm according to the present disclosure;

FIGS. 44A-E are plots of ECG data of various patients as measured using the HR algorithm according to the present disclosure and a comparative heart rate monitor;

FIGS. 45A-D are plots of ECG data during various activities;

FIG. 46 is a flow chart illustrating the processing of ECG data to determine HRV metrics according to the present disclosure;

FIG. 47 is a flow chart illustrating the data flow of comparison of HRV metrics according to the present disclosure;

FIG. 48 is a plot illustrating HRV metrics for patient 5 according to the present disclosure;

FIG. 49 is a flow chart for determining resting according to the present disclosure; and FIG. 50 is a detailed flow chart illustrating the block for the punctuated inactivity calculation of FIG. 49.

DETAILED DESCRIPTION

Various examples are described and illustrated herein to provide an overall understanding of the structure, function, and use of the disclosed articles and methods. The various examples described and illustrated herein are non-limiting and non-exhaustive. Thus, an invention is not limited by the description of the various non-limiting and non-exhaustive examples disclosed herein. Rather, the invention is defined solely by the claims. The features and characteristics illustrated and/or described in connection with various examples may be combined with the features and characteristics of other examples. Such modifications and variations are intended to be included within the scope of this specification. As such, the claims may be amended to recite any features or characteristics expressly or inherently described in, or otherwise expressly or inherently supported by, this specification. Further, Applicant reserves the right to amend the claims to affirmatively disclaim features or characteristics that may be present in the prior art. The various examples disclosed and described in this specification can comprise, consist of, or consist essentially of the features and characteristics as variously described herein.

Any references herein to "various examples," "some examples," "one example," "an example," or like phrases mean that a particular feature, structure, or characteristic described in connection with the example is included in at least one example. Thus, appearances of the phrases "in various examples," "in some examples," "in one example," "in an example," or like phrases in the specification do not necessarily refer to the same example. Furthermore, the particular described features, structures, or characteristics may be combined in any suitable manner in one or more examples. Thus, the particular features, structures, or characteristics illustrated or described in connection with one example may be combined, in whole or in part, with the features, structures, or characteristics of one or more other examples without limitation. Such modifications and variations are intended to be included within the scope of the present examples.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

The grammatical articles "a," "an," and "the," as used herein, are intended to include "at least one" or "one or more," unless otherwise indicated, even if "at least one" or "one or more" is expressly used in certain instances. Thus, the foregoing grammatical articles are used herein to refer to one or more than one (i.e., to "at least one") of the particular identified elements. Further, the use of a singular noun includes the plural and the use of a plural noun includes the singular, unless the context of the usage requires otherwise.

A wearable device can be coupled (e.g., attached) to a body (e.g., skin) of a patient and can determine if the patient ingested digital medicine (e.g., ingestible event marker (IEM) embedded in a pill or other pharmaceutical product) and/or the frequency of ingestion from ingestible sensor data generated by the IEM. The ingestible sensor data can be generated of the IEM after contact with a bodily fluid of the patient, such as, for example, stomach acid. The wearable device can also determine physiological metrics, such as, for example, step count, body angle, heart rate, heart rate variability, rest, and resting heart rate. The wearable device can be battery operated and have limited resources, such as, for example, memory, battery life, computational power, and communication bandwidth, but the wearable device may have to detect all ingestions of digital medicine by the patient involving an IEM (e.g., high-frequency, in-body electric signals-10 KHz and higher) as well as detect and/or receive various types of physiological data (e.g., high resolution sensor data, such as, electrocardiogram (ECG) data and accelerometer data). Due to high performance requirements but limited resources, various algorithms and other innovations are presented herein to optimize performance and improve battery life of the wearable device and/or a system comprising the wearable device.

The various algorithms (e.g., step count algorithm, body angle algorithm, heart rate algorithm, peak finder algorithm, adaptive thresholding algorithm, heart rate variability algorithm, R-R cleaning Algorithm, deltaR-R cleaning algorithm, merge twin interval algorithm, split tall intervals algorithm, absorb short intervals algorithm, bimodal detection algorithm, resting algorithm) and other innovations can be solely on the wearable device or distributed across a wearable device and a remote device (e.g., a paired mobile device, a backend server, the cloud). The various algorithm can be executed by a processor on the wearable device and/or a processor on the remote device. The remote device may be less resource constrained, but the remote device may receive lower resolution data that was post-processed by the patch which may effect the accuracy of the physiological metrics. Thus, the various algorithms and other innovations can balance the limited resources of the wearable device and the need for high accuracy physiological metrics such as, for example, ANSI EC-13.

The wearable device and/or a system including the wearable device can be configured to detect and/or receive discontinuous data comprising frames of ingestible sensor data and frames of physiological data of the patient interspersed in time gaps between the frames of the ingestible sensor data. Different types of physiological data can be detected, received, and/or processed in parallel, while the ingestible sensor data can be detected, received, and/or processed in series with the physiological data. That is, the wearable device can switch between detecting, receiving, and/or processing ingestible sensor data and detecting, receiving, and/or processing physiological data in a rapid fashion. The ingestible sensor data and the physiological data may be serially detected, received, and/or processed and may not be parallel in time to each other. Piecing and/or stitching together the frames of physiological data to generate accurate physiological metrics while detecting if the patient ingested digital medicine can present challenges.

Therefore, examples of the present disclosure which can increase the accuracy of physiological metrics while detecting if the patient ingested digital medicine and/or improve performance of the wearable device can comprise the various algorithms according to the present disclosure. The examples of the present disclosure can process discontinuous data accurately which can enable reduced memory requirements and reduced process requirements.

The frames of data utilized can be prioritized based on a desired power consumption (e.g., battery life) of the wearable device and/or system including the wearable device, a desired accuracy, and/or a desired data transfer size. In various examples, the wearable device and/or a system including the wearable device can be configured to detect and/or receive a first continuous data comprising frames of ingestible sensor data and and a second continuous data comprising frames of physiological data.

Wearable Device Architecture

Figure 1:
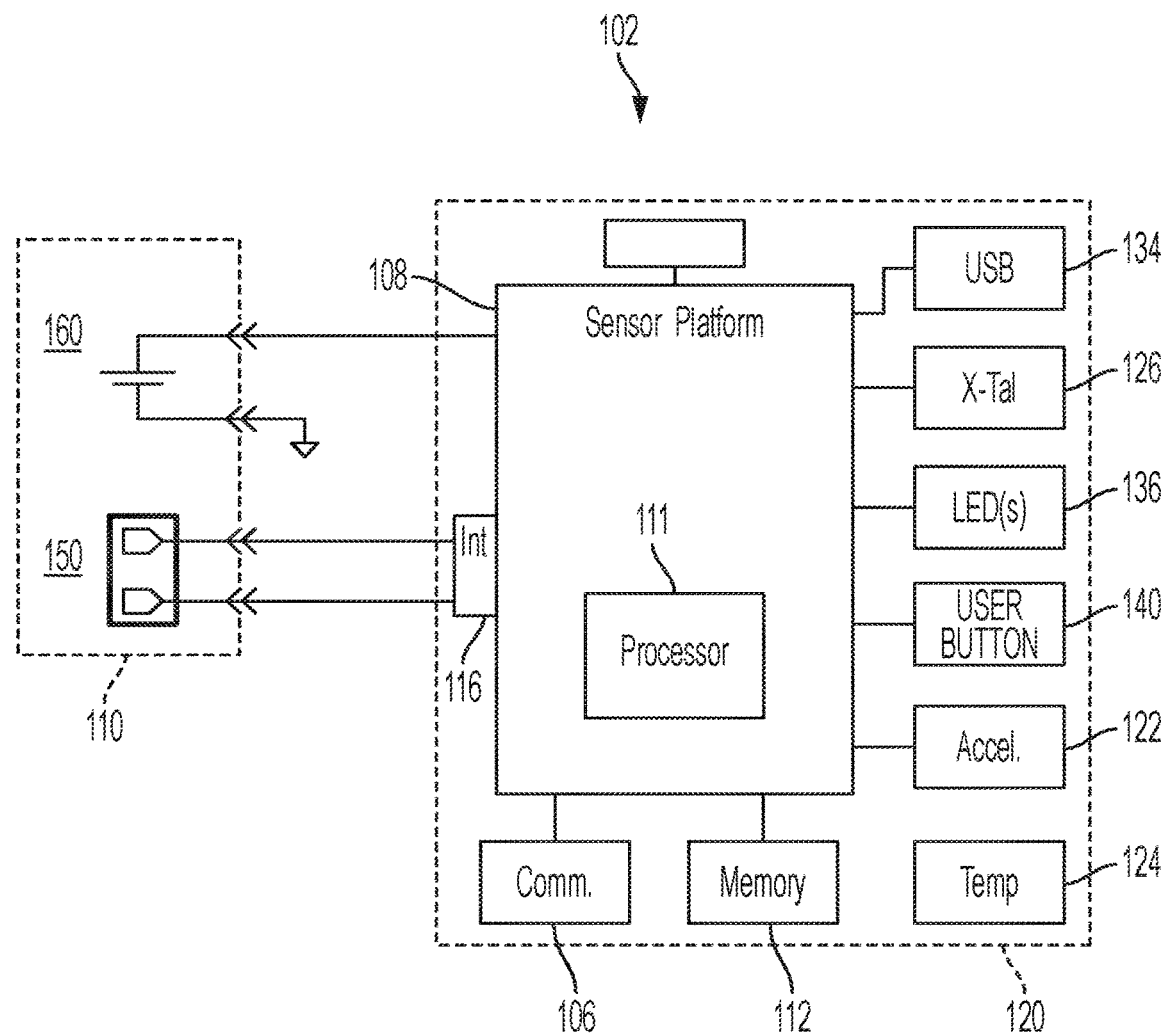
FIG. 1 is a system diagram illustrating a wearable device according to the present disclosure.

FIG. 1 illustrates a system diagram of an example of a wearable device 102. The wearable device can be configured to be removably attached to skin of a patient. The wearable device can be re-wearable or the wearable device can be disposable. The wearable device 102 can comprise at least two components including a disposable component 110 and an electronics module 120 (e.g., a reusable electronics module). Each of the disposable component 110 and the electronics module can comprise a printed circuit board assembly (PCBA). The electronics module 120 can comprise a computing platform 108, a processor 111 (e.g., a microcontroller unit (MCU)), a wireless communication circuit 106, a universal serial bus 134 (USB), an accelerometer (ACC) 122, memory 112, an LED 136, a 32 KHz crystal clock (X-Tal) 126, a user button 140 that may be used to initiate a communication connection with an external device, and sensor interfaces 116. In various examples, the electronics module 120 can comprise a gyroscope, a body composition circuit, a SpO$_2$ oximetry circuit, and circuits for processing ECG signals, temperature signals, and accelerometer signals. The SpO$_2$ pulse oximetry circuit can monitor functional oxygen saturation of arterial blood by calculating the ratio of oxygenated hemoglobin to hemoglobin that is capable of transporting oxygen. The SpO$_2$ pulse oximetry circuit can be configured to provide continuous, noninvasive measurements of SpO$_2$ and can display a plethysmographic waveform. Heart rate values can be derived from the SpO$_2$ pulse oximetry signal. The electronics module 220 also comprises a connection port to external memory, a connection port to external sensors, and a hardware accelerator.

The electronics module 120 can comprise an application specific integrated circuit (ASIC)-based computing platform 108 that can comprise a hardware architecture and software framework to implement various functionality of the wearable device 102. The computing platform 108 may be disposed on and interfaced with the PCBA of the electronics module 120. The disposable component 110 can interface with the PCBA of the electronics module 120. The electronics module 120 and the disposable component 110 each may comprise additional modules that may be disposed on the PCBA of the respective component, 110, 120 or may be disposed off of the PCBA of the respective module, 110, 120.

The computing platform 108 can comprise circuits designed to interface with various sensors and combinations of components of the wearable device 102. For example, the computing platform 108 can provide a combination of analog front-end, vector/digital signal processing, microprocessor and memory in a single low-power ASIC/chip that can comprise multiple functions, such as, for example, software-defined radio for detection of ingestible event markers, sensing and decoding of electrocardiogram (ECG) signals, AC skin impedance measurements, temperature measurements (e.g., of the skin and/or ambient), DC skin impedance (e.g., galvanic skin response (GSR)) measurements, accelerometer measurements, and other biological/medical data sensors.

The processor 111 can be a central processing unit (CPU). The processor 111 may be implemented as a general purpose processor, a chip multiprocessor (CMP), a dedicated processor, an embedded processor, a digital signal processor (DSP), a network processor, a media processor, an input/output (I/O) processor, a media access control (MAC) processor, a radio baseband processor, a vector co-processor, a microprocessor such as a complex instruction set computer (CISC) microprocessor, a reduced instruction set computing (RISC) microprocessor, and/or a very long instruction word (VLIW) microprocessor, or other processing device. The processor also may be implemented by a controller, a microcontroller, an application specific integrated circuit (ASIC), a field programmable gate array (FPGA), a programmable logic device (PLD), and so forth.

The processor 111 can be configured to run an operating system (OS) and various mobile applications. For example, an OS can include operating systems generally known under the trade name of Microsoft Windows OS, and any other proprietary or open source OS. Mobile applications can include, for example, a telephone application, a camera (e.g., digital camera, video camera) application, a browser application, a multimedia player application, a gaming application, a messaging application (e.g., e-mail, short message, multimedia), a viewer application, and so forth. The processor 111 may be arranged to receive information through a communications interface. The communications interface may comprise any suitable hardware, software, or combination of hardware and software that is capable of coupling the wearble device 102 to one or more networks and/or devices.

The processor 111 can comprise, for example, an ARM Cortex™ M3 processor, for real-time applications, a signal processing accelerator (e.g., vector co-processor) such as, for example, a Vector Math Accelerator, program memory, data memory, serial interfaces such as, for example, SPI, universal asynchronous receiver transmitter (UART), two-wire multi-master serial single ended bus interface (I2C), general purpose input/output (GPIO), a real-time clock, an analog-to-digital converter (ADC), gain and conditioning circuits for bio-potential signals, light emitting diode (LED) drivers, among other components. The processor 111 can receive a signal from each of the sensors by operating the analog front end for analog sensors and by receiving digital data from sensors with the ADC converter. The processor 111 can processes the data and store the results into the memory 112 in form of data records. In various examples, the processor 111 may have a very long instruction word (VLIW) processor architecture.

The wireless communication circuit 106, can be a mobile chipset radio frequency (RF) wireless circuit or simply cellular radio. The wireless communication circuit 106 may be a low power mobile chipset and can be configured to connect to the cellular network as well as other remote devices (e.g., wireless devices such as, cell-phones, smart phones, tablet computers, laptop computers, gateway devices, among others). The wireless communication circuit 106 can comprise an antenna to receive and transmit wireless signals, a transmitter circuit, a receiver circuit, and a link master controller that includes a mechanism to connect (establish a link) to another, external, wireless device and transfer data, as described in more detail herein below. The link master controller can establish connection to an external device such as a mobile device. As a master of the link, the link master controller can perform control of data transmission over the link to the external device, including timing control and radio frequency control (channel hopping). The link master controller can send a signal to a remote device with an instruction that gives a number of data records stored in memory (a total number of all data records and a total number of records of each data type). The wireless communication circuit 106 may be implemented using a mobile chipset available from a variety of vendors including, without limitation Tegra by Nvidia, Snapdragon by Qualcomm, OMAP by Texas Instruments, Exynos by Samsung, Ax by Apple, NovaThor by ST-Ericsson, Atom by Intel, i.MX by Freescale Semiconductor, RK3xxx by Rockchip, A31 by AllWinner, among others. Such mobile chipsets are employed by mobile telephones, otherwise known in the art as "mobile," "wireless," "cellular phone," "cell phone," "hand phone (HP)," "smart phone," among others. In various examples, the wearable device 102 can communicate via a wired circuit. In various examples, the wearable device 102 can communicate via Bluetooth.

After each connection, the processor 111 can continue to receive all sensor signals, processes the data, and store new data records into the memory 112. Upon each subsequent connection, the link master controller can sends a signal to a remote device (e.g., external to the wearable device 102) with new data records since last connection and confirm that the data records were transmitted successfully. The link master controller can receive a signal from the remote device that establishes if the remote device is ready to receive data records and also can receive a signal from the remote device that establishes which data records were not transferred successfully. The link master controller can avoid repeating the transmission of the data records that already have been transmitted, which can improve battery power use for a longer operation and resend all data records that were not transferred successfully. The link master controller may delete from the memory 112 all or some successfully transferred data records at a later time (for example, when the memory 112 gets full).

The memory 112 can be non-transitory memory and can comprise machine executable instructions that when executed by the processor 111 can cause the processor 111 and/or a processor on a remote device to perform the functions of the various algorithms and other innovations described herein. In various examples, at least part of the machine executable instructions are stored in memory on the remote device.

The sensor interface 116 can be disposed between electrodes 150 and a band pass filter or channel. The sensor interface 116 can provide an analog front end and may include programmable gain or fixed gain amplifiers, programmable low-pass filter, programmable high-pass filter. The sensor interface 116 may comprise active signal conditioning circuits including strain gauge measurement circuits, for example. One channel can receive low frequency information associated with the physiological data of the patient (e.g., user, subject) and another channel can receive high frequency information associated with an electronic device within the patient. The high frequency channel can receive DC data of the patient. The high frequency channel data can be passed to a digital signal processor (DSP) implemented in the computing platform 108 and then to processor 111 for decompression and decoding, or passed directly to the processor 111. The low frequency channel data can be passed to the DSP portion of the computing platform 108 and then to processor 111, or passed directly to the processor 111. The DSP portion and the processor 111 can decode the data from the high frequency channel and low frequency channel. The data can then be processed and prepared for transmission.

Signal processing may or may not be applied to the raw data collected from the channels. Signal processing may occur in the real space, complex number space, or in the polar coordinates space. Functions of the signal processing include filters, such as, finite impulse response (FIR) and infinite impulse response (IIR), mixers, fats Fourier transforms (FFTs), cordics, among others. Raw data may simply be stored in memory 112 and later processed downstream. The signal processing may occur in the processor 111 or may occur in the signal processing accelerator which can be incorporated into the computing platform 108. Physiological data from the various sensors on the wearable device 102 can be processed by the processor 111 and may be transmitted as real-time or raw data, or derived quantities or parameters may be transmitted. The physiological data can comprise accelerometer data, ECG data, and other physiological data. The accelerometer data can be parallel in time to the ECG data.

The electronics module 120 can comprise two temperature sensors 124 that are identical but placed in different locations, such as, for example, one close to the skin and another extending into the ambient environment for measuring additional data. The temperature sensors 124 may be configured to measure and record, skin, ambient, and circuit board temperature. The temperature sensors 124 may be used to measure heat flux between the skin and the ambient temperature sensor. The temperature sensors 124 can be thermistor devices with negative temperature coefficient (NTC) or positive temperature coefficient (PTC). The temperature sensors 124 can use integrated semiconductor devices. The temperature signals can be provided to the processor 111 and can be processed by the processor 111 and prepared for transmission by a transmitter portion of the wireless communication circuit 106.

Figure 2:
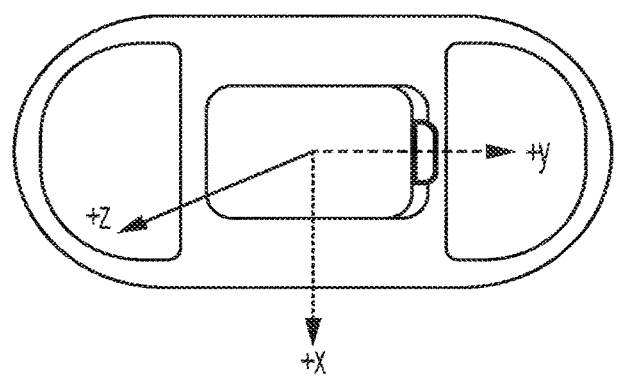
FIG. 2 illustrates a front view of a wearable device according to the present disclosure.

The accelerometer 122 can be a 3-axis accelerometer with a resampling frequency correction processor. As illustrated in FIG. 2, an example of a wearable device is provided and the associated X, Y, and Z axis that the embedded accelerometer of the wearable device may measure and output accelerometer data based on are shown. The accelerometer 122 can comprise different recording modes, such as, for example, the wearable device 102 can record raw accelerometer X, Y, Z data only or the wearable device 102 can record raw accelerometer X, Y, Z data and regular accelerometer metrics.

Referring back to FIG. 1, the accelerometer 122 can be a digital accelerometer comprising a MEMS-based acceleration sensor element, a digitizer, and digital interface control logic. The accelerometer 122 can use a resistor-capacitor (RC) oscillator with low accuracy to strobe the digitizer sampling input. The electronics module 120 can comprise an accelerometer sampling frequency correction processor that receives signals from the accelerometer 122 and performs re-sampling to compensate for RC oscillator error.

The accelerometer 122 can comprise a sampling frequency correction processor comprising a reference clock (high accuracy oscillator), a fixed up-sample block, a digital filter, a programmable down-sample block, and a control circuit that selects down-sample coefficient based on comparison of timing of the signal from accelerometer and the reference clock. The resampling function can keep alignment to a reference clock in a sliding window to generate a precise sampling rate. A time algorithm can calibrate the real time 32 kHz crystal clock (X-Tal) 126. The accelerometer 122 sampling frequency correction processor can set the down-sampling coefficient for each frame of data from the accelerometer signal. The timing of the accelerometer signal can be tracked continuously and the down-sampling coefficient can be selected to minimize accumulated timing errors. Thus, accelerometer data from the accelerometer 122 can be aligned to the accurate clock with high precision.

The electronics module 120 can employ a low-power low-memory data storage and transfer scheme. For example, the storage and transfer of data in the memory 112 can be optimized for low-power and low memory usage. Physiological data from sensor signals can be stored as data records in the memory 112, each with a type identifier. Data records can be transferred in a packet payload to a remote device by the wireless communication circuit 106. Data records can be stored sequentially with variable length to optimize space usage in memory 112. A data directory can be provided in memory 112 which can enable fast record read access from the memory 112. The data directory can also enable rapid counting of the data records by type.

The electronics module 120 can employ a high-assurance integrity data storage and transfer scheme. For example, the wearable device 102 memory storage and transfer scheme can be designed for high-assurance data integrity. For each data record stored in the memory 112 of the wearable device 102, there can be an error-detecting code that can be used to detect data record corruption. When the wearable device 102 reads a data record from the memory 112 prior to data packet transfer to the remote device, the error-detecting code can be checked. When the wearable device 102 detect corruption of the stored data record, an error signal can be sent to the remote device by the wireless communication circuit 106. Each packet transferred from the wearable device 102 to the remote device can contain an error-detecting code which can be used by the remote device to detect packet corruption.

The signal processing accelerator portion of the computing platform 108 can comprise a computational engine optimized for implementing high efficiency signal processing tasks. Signal processing functions can be hard coded in logic which can be 10 times or more efficient compared to software-based algorithms implemented in software running on processor 111 or other microcontroller unit. The efficiency can be a decrease in chip size, a decrease in power consumption, and/or a decrease in clock speed. The signal processing functions can maintain some level of programmability, but can utilize execution units that are optimized calculations. For example, the signal processing functions can employ a Fast Fourier Transform (FFT)-butterfly engine which can enable FFT calculations for various sized data sets, but maintain significant efficiency improvement over software running on the processor 111. The execution units also may be multiply accumulate units (MAC), which are a common DSP function block or could be a floating point calculation unit(s) or FIR filter primitives, etc. In these examples, the efficiency for a given integrated circuit process can be greater than that of software on the processor 111, but less than that of dedicated hardware, however they can be much more flexible in terms of balancing limited resources and accuracy of physiological measurements.

The signal processing accelerator can maintain an interface with the processor 111. This interface may include first-in-first-out (FIFO) registers, dual port memories, the direct memory access (DMA) engine of the processor 111, and/or registers. The interface can include some form of contention recognition or avoidance which may be handled at the register-level or at the memory block level. Mechanisms involved may include register flags set, which can be polled by the processor 111 and signal processing accelerator, interrupts to signal can either block or delay functions that hold a read or write request until the higher priority device has completed their activity.

The disposable component 110 can be coupled to the PCBA of the electronics module 120. The disposable component can comprise a sensor attached for interface to the item to be monitored (person, animal, machine, building, etc.), such as, for example, an electro-dermal activation (EDA) sensor, a GSR sensor, a temperature sensor (e.g., of the skin and/or ambient), a body composition sensor (50 Hz), SpO2/pulse oximetry sensor, strain gauge sensor, an accelerometer, and other biological/medical data sensors. Various algorithms executed by the computing platform 108 or the processor 111 provide can generate metrics, such as, for example, step count, body angle, heart rate, heart rate variability, rest, resting heart rate, heat flux, respiration rate, stress level, fall detection, and other physiological metrics.

The disposable component 110 may also comprise a battery 160, a cradle to hold the battery, battery holder or housing (covering), an adhesive, and an electrode 150 (e.g., at least two electrodes). Power can be provided to the wearable device 102 from the battery 160. The battery 160 can be a disposable coin cell with a battery life approximately equal to the useful life of the adhesive of the disposable component 110. The adhesive can adhere the wearable device 102 to skin of the patient. The adhesive can comprise a useful life of 3 to 10 days on most patients. The electrode 150 can comprise hydrogel electrodes and discrete stainless steel electrodes. The hydrogel electrodes can be used for detecting high-frequency, in-body electric signals (10 KHz and higher) which can indicate a patient has ingested digital medicine.

The memory 112 can comprise any machine-readable or computer-readable media capable of storing data, including both volatile and non-volatile memory. For example, memory 112 may include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferro-electric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

Step Counting

The wearable device 102 can be worn by a patient by attaching the wearable device to the patient with the adhesive of the disposable component 110 (e.g., adhesive strip). When the patient moves, the accelerometer 112 can provide an accelerometer signal based on the acceleration forces experienced by the accelerometer 122. Variation in acceleration can indicate motion/activity of the patient. The accelerometer signal can be converted into accelerometer data by the wearable device 102.

Figure 3:
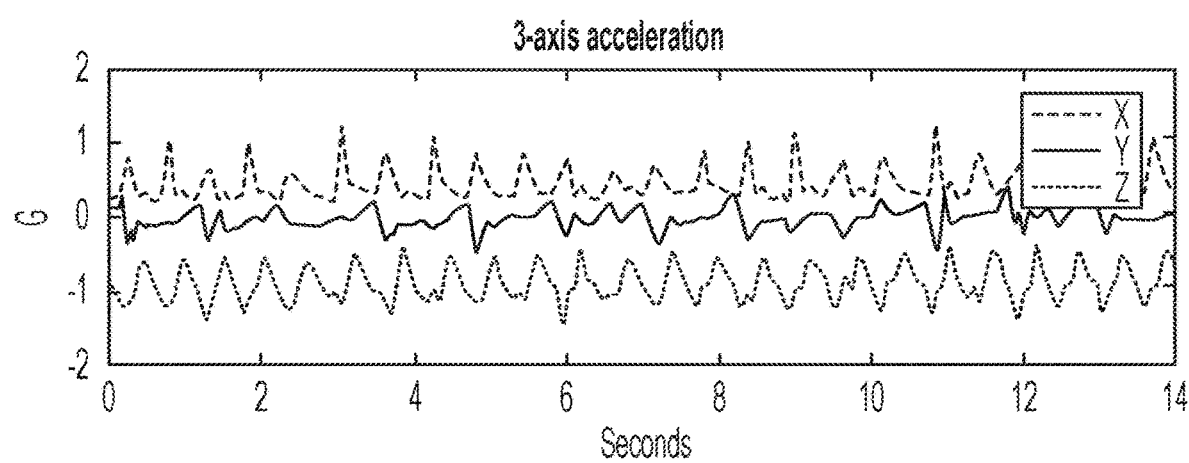
FIG. 3 illustrates accelerometer data comprising an individual trace for each axis according to the present disclosure.

Walking can be a periodic/regular motion which can be interpreted as strong peaks in the accelerometer data and/or auto-correlation data produced from the accelerometer signal. The accelerometer data can be analyzed and used to calculate a number of steps (e.g., step count) that the patient took. For example, as illustrated in FIG. 3, accelerometer data 302 is provided which can comprise an individual trace for each axis, X, Y, Z. The accelerometer data 302 comprises a 14 second block of acceleration data in which the patient wearing the wearable device 102 took 24 steps. Counting the number of times the accelerometer data 302 crosses a threshold can be used to determine the physiological metric of step count from the accelerometer data 302. The step count measured from the accelerometer data 302 is 103 steps per minute based on measuring 24 steps in a 14 second period.

The wearable device 102 may be used by patients who struggle with mobility (e.g., elderly patients) or otherwise walk at a slow pace. As used herein, "slow walking" refers to a step rate in a range of 15 to 80 steps per minute and normal walking refers to a step rate in a range of 80 to 150 steps per minute. Previous comparative algorithms may not be able to accurately calculate a step count from accelerometer data for patients who slow walk (e.g., shuffle and/or move slowly) or who may be driving. For example, the accelerometer data may not look like normal walking steps and the accelerometer data may not be easily analyzed for calculating a step count. For example, the top of FIG. 4A illustrates example accelerometer data at a movement rate of 100 steps/min (e.g., normal walking) and the top of FIG. 4C illustrates example accelerometer data at a movement rate of 50 steps/min (e.g., slow walking).

Figure 4A:
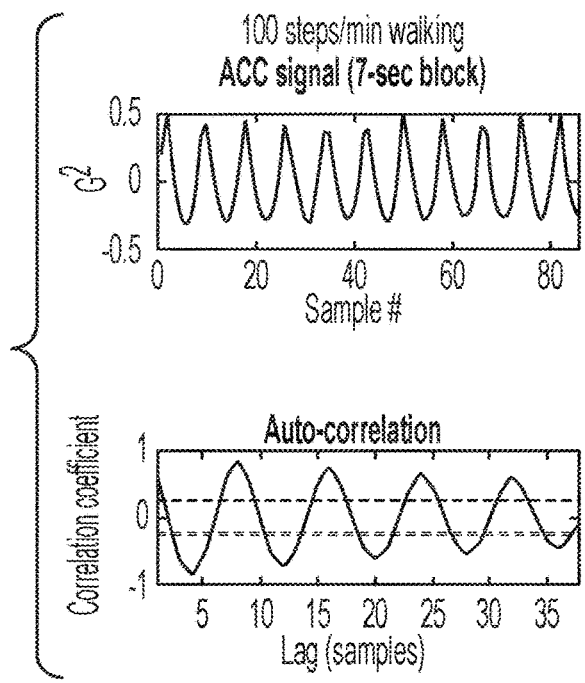
Figure 4B:
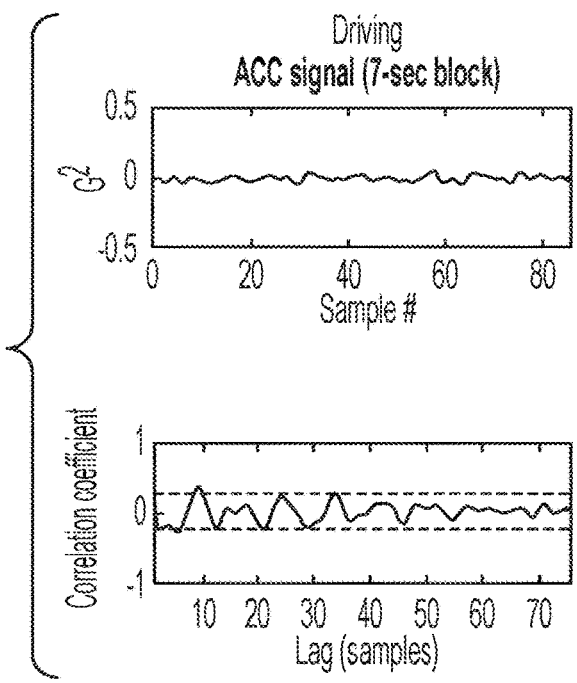
Figure 4C:
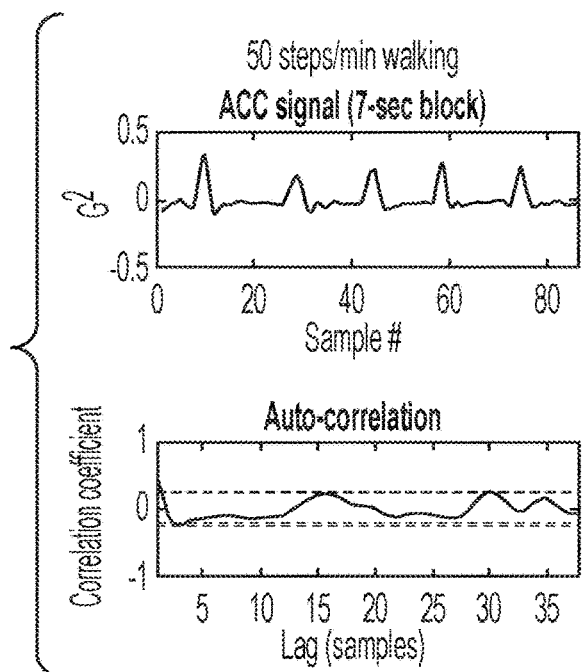
Figure 4D:
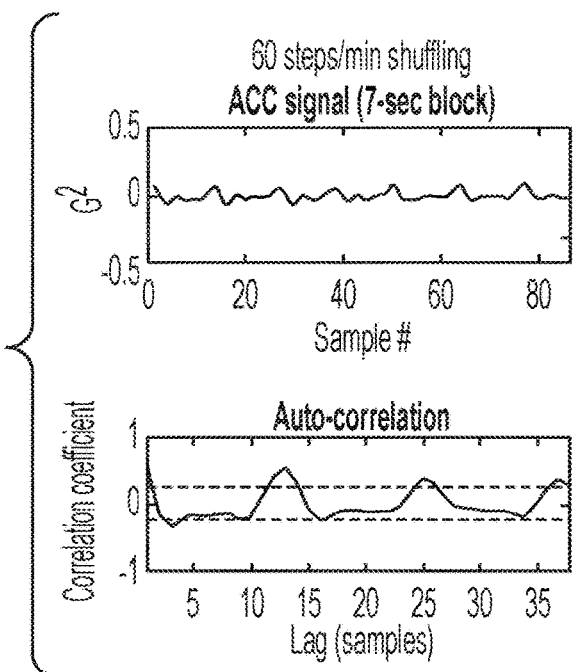

A comparative algorithm may rely solely on counting level crossings in auto-correlation data (e.g., thresholds as illustrated by dashed lines in FIGS. 4A-4E). As illustrated in the bottom of FIG. 4A, counting crossing of thresholds in auto-correlation data produced by normal walking may result in an accurate step count (e.g., greater than +/− 10%) based on solely level crossings. However, as illustrated in the bottom of FIG. 4C, counting level crossings in auto-correlation data produced by slow walking may result in an inaccurate step count based solely on level crossings.

Referring to FIG. 4E, a plot of points of step count data is provided where each point represents one seven second block of accelerometer data that consisted only of the respective activity as identified in FIG. 4E that has been analyzed from a comparative algorithm. The normal walking 100 steps per minute data was sampled over 4 minutes with an expectation of a value of 400 steps for the step count; the slow walking 50 steps per minute data was sampled over 4 minutes with an expectation of a value of 200 for the step count; the slow shuffling 60 steps per minute data was sampled over 4 minutes with an expected value of 240 for the step count; the medium-paced shuffling 80 steps per minute data was sampled over 4 minutes with an expected value of 320 for the step count; and the driving data (e.g., 0 steps per minute) was sampled over various times with an expected value of 0 for the step count.

In addition to the inaccurate step count for slow walking, as illustrated in FIGS. 4B, 4E, and 5, driving may cause false step counts. Additionally, as shown in Table 1, comparative pedometers that comprise comparative algorithms may provide an inaccurate step count (e.g., detect false steps while driving). Additionally, the comparative pedometers receive accelerometer data continuously (e.g., not in a discontinuous manner).

TABLE 1

Step counts of various devices

| Activity | Comparative Pedometer 1 | Comparative Pedometer 2 | Raw samples from Comparative Pedometer 2 processed with comparative algorithm (MATLAB) |
|---|---|---|---|
| Driving to work (50 mins) | 0 | 0 | 117 |
| Treadmill (400 steps) | 411 | 448 | 421 |
| Recumbent stationary bike (5 mins) | 124 | 615 | 210 |
| Upright stationary bike (5 mins) | 228 | 274 | 0 |
| Elliptical (3 mins) | 412 | 414 | 445 |

Therefore, a step count algorithm to accurately count steps in discontinuous data comprising accelerometer data generated by the wearable device 102 during slow walking is provided. The step count algorithm can determine the step count in a step rate range of 80 to 150 steps per minute using the detected physiological data with a mean error of plus or minus 3 percent as measured over at least 1000 steps. Additionally, the step count algorithm can limit, if not prevent, false step counts while driving or other during other types of movement.

The step count algorithm can save memory and power by estimating a continuous step rate from discontinuous data. For example, every minute the wearable device can collect a 14-second frame of accelerometer data and compute a step rate on this frame and interpolate the step rate to derive the number of steps for the whole minute. In order to optimize accuracy, the algorithm can consider half-steps at the boundaries of the 14-second frame.

In addition, the wearable device 102 can be configured to classify the data based on an activity level. For example, the wearable device 102 can distinguish "purposeful walking" that includes faster, more defined steps (e.g., a first activity level), compared to casual walking, such as simply walking to the bathroom or to the kitchen (e.g., a second activity level less than the first activity level). The types of walking can be distinguished by the step count algorithm based on the accelerometer data.

The step count algorithm can receive accelerometer data and can be distributed across a wearable device 102 and a remote device for execution by a control circuit. For example, the step count algorithm can be stored in memory 112 and can be utilized by processor 111 to transform accelerometer data received from accelerometer 122 into a physiological metric, such as, for example, a step count.

For the purposes of describing the configurations of the algorithms herein, the accelerometer values are to be interpreted in units of "g", where "g" is the acceleration due Earth's gravity (~9.8 m/s$^2$) unless stated to the contrary. For performance optimization, the design implementation can operate on raw accelerometer counts.

The step count algorithm can comprise fixed parameters as described in Table 2 that can be set to default values within the source code but can be adjusted (with full recompilation of the software) without whole or partial redesign of the step count algorithm.

TABLE 2

Fixed parameters

| Parameter | Type | Description |
|---|---|---|
| ACC_AC_LIM | CONSTANT | Autocorrelation maximum search limit |
| ACC_NUM_BINS | CONSTANT | The number of bins per dimension (X, Y, and Z) for the body angle algorithm |
| ACC_MIN_MODE | CONSTANT | The minimum bin count in each dimension before the reference vector calculation starts. |
| ACC_MAX_MODE | CONSTANT | The maximum bin count in any dimension before reference vector calculation is frozen |

The step count algorithm can comprise programmable parameters as described in Table 3. The step count algorithm can be set to default values and can be re-configured during production and/or use via a wireless/wired interface. Each programmable parameter can maintain its set value through all state transitions and complete removal of power (such as battery disconnect) from the wearable device 102.

TABLE 3

Programmable parameters

| Parameter | Type | Description |
|---|---|---|
| ACC Event Interval | UINT16 | Sets the interval at which the ACC measurement is scheduled |
| ACC Duration | UINT16 | Sets the duration of the ACC measurement. |
| ACC Recording Mode | UINT16 | Controls which records are produced<br>1: ACC records<br>2: ACR records<br>3: ACC and ACR records |
| ACC Num Crossing | UINT16 | The number of auto-correlation crossings that must be met to consider counting steps. |
| ACC Total Activity Threshold | FLOAT | Activity threshold that must be met to consider counting steps. |
| ACC Total Activity Low Threshold | FLOAT | Lower bound on the activity threshold that must be met to consider counting steps at lower step rates |
| ACC Energy Expenditure Threshold | FLOAT | Energy expenditure threshold that must be met to consider counting steps |
| ACC Energy Expenditure Low Threshold | FLOAT | Lower bound on the energy expenditure threshold that must be met to consider counting steps at lower step rates |
| ACC Step Zero Crossing Threshold | FLOAT | The raw signal must cross zero and this threshold to be considered a step. |
| ACC Corr Zero Crossing Threshold | FLOAT | The auto-correlation signal must cross zero and this threshold to be considered a correlation crossing. |
| ACC BA Num Records | UINT16 | Number of valid ACC records needed before updating the reference vector |
| ACC BA Min Step Threshold | UINT16 | The Minimum number of steps per minute to allow the ACC record to be valid for Body angle calculations |

TABLE 3-continued

Programmable parameters

| Parameter | Type | Description |
| --- | --- | --- |
| ACC BA Max Step Threshold | UINT16 | The Maximum number of steps per minute to allow the ACC record to be valid for Body angle calculations |

The step count algorithm can process the accelerometer data in a select time window sampled at select frequency. In examples with a 14 second time window and a select frequency of 12.5 GhZ, 175 samples would be produced. A step count can be derived with a sample buffer comprising a single block as illustrated in FIG. 6 or the sample buffers can be broken into two blocks, period 1 (P1) and period 2 (P2) as illustrated in FIGS. 7A-B. In examples where the number of samples is odd, one point may be excluded so each period is equal. In examples where the number of samples is 175, the 175th sample can be excluded so each period is equal.

The step count algorithm can perform evaluations, calculations, and transformations described herein and produce the accelerometer record (ACR) as described in Table 4. The ACR can be produced once per measurement period or more times if desired.

TABLE 4

ACR

| Name | Type | Description |
| --- | --- | --- |
| StepCount | FLOAT | Step Count per duration/interval |
| AStepCount | UINT16 | Step Counts per minute |
| Body Angle | FLOAT | Body Angle |
| Total Activity (p1, p2) | FLOAT x2 | Total activity |
| Zero Crossing (p1, p2) | UINT16 x2 | Number of zero crossings of auto-correlation of total acceleration |
| Accel Mean(X, Y, Z) | FLOAT x3 | Mean acceleration per dimension. |
| Accel Ref Vector(X, Y, Z) | FLOAT x3 | Reference Vector |
| Energy Expenditure (p1, p2) | FLOATx2 | Energy expenditure |
| Signal Enhanced | UINT8 | Flag (e.g., Signal Enhanced Flag) to indicate signal enhancement was executed on the data and if the reference data has been calibrated (MSB). |
| Accel StdDev(X, Y, Z) | FLOAT x3 | Standard Deviation of acceleration per dimension |

Accelerometer data can be normalized to "g" (or $g^2$, if it is a measure of squared acceleration) using fixed conversion value G which is defined by the sensitivity of the accelerometer used as illustrated in Equation 1. The default may be 2G sensitivity.

$$x\_out_i = (x\_raw_i) \times (x\_gain/G)^K \quad K \in \{1,2\} \qquad \text{Equation 1}$$

G=1 g value in raw acclerometer units (For each
K=The square value. Will be one unless it is applied to exponent acceleration X,Y,Z)

FIG. 6 illustrates an example flowchart of a step count algorithm that can accurately determine a step count during slow walking of a patient. As illustrated, x-axis accelerometer data, y-axis accelerometer data, and z-axis accelerometer data, collectively accelerometer data, can be processed by the step count algorithm.

The raw acceleration data (e.g., vectors) in each axis of the accelerometer data can be processed by the step count algorithm using a boxcar filter to smooth noise and eliminate high frequency components of the signal according to Equation 2, 602.

$$X_i = \sum_{j=0}^{M-1} F_j x_{i+j} \quad \text{(For each } X, Y, Z) \qquad \text{Equation 2}$$

Where each FIR tap value of $F_j = 1/M$,
M is number of taps (calculated as floor(sampling_rate/5))
$X_i$ denotes the $i^{th}$ output sample
$X_j$ denotes the $j^{th}$ input sample In examples with the default parameter values AccFs=12.5 Hz and M=2, frequency components below 3.125 Hz can be reproduced accurately.

Accelerometer data sampled at 12.5 Hz can have a tap filter applied to the raw accelerometer data, such as, for example, a 2-tap filter. The more taps in the filter the more averaging of the accelerometer data. The tap filter can determine the high frequencies which can be faithfully represented. Different length of tap filters can be applied to the raw accelerometer data to characterize the sensitivity of the step counting during activity (e.g., gym exercises). The sampling rate and the digital filters (e.g., tap filter) applied to the raw accelerometer data can be configured to the desired application. In various examples, the hardware of the wearable device 102 can support a different sampling rate (e.g., a higher sampling rate).

Post boxcar filtering acceleration data in each axis of the accelerometer data can be transformed into total acceleration (totAcc, $Acc_{total,i}$) by calculating the squared L2 norm from each axis of the accelerometer data as illustrated in Equation 3, 604.

$$Acc_{sqr,i} = (x_i^2 + y_i^2 + z_i^2)/2 \qquad \text{Equation 3}$$

The step count algorithm can utilize the squared L2 norm instead of the L2 norm as a computational simplification. The scaling factor (e.g., division by 2) in Equation 3 can prevent overflow/saturation of a buffer in memory. When determining and/or programming a threshold related to total acceleration (e.g., totActThresh, totActThreshLo), the scaling factor can be taken into account.

The total activity (totActivity) of the total acceleration data can be calculated by taking the standard deviation of the total acceleration data (std (totAcc)) as shown in Equation 4, 4606.

$$\text{Activity}_{total} = \text{StdDev}(acc_{total,i}) \qquad \text{Equation 4}$$

The total activity can be computed independently for blocks P1 and P2 in examples with two blocks of accelerometer data, resulting in two floating point values as illustrated in FIGS. 7A-B.

Referring back to FIG. 6, the total activity can be used by the step count algorithm to evaluate whether a block of accelerometer data contains valid step activity, 608. For example, the step count algorithm can evaluate whether or not the total activity data meets or exceeds an activity threshold. If the total activity meets or exceeds the activity threshold, the step count algorithm proceeds to step 624 and proceeds to mean adjust the accelerometer data and evaluate the acceleration data for a step count.

However, if the total activity does not meet or exceed the activity threshold, the step count algorithm can evaluate whether the accelerometer data should be enhanced, 610. For example, the step count algorithm can evaluate whether or not the total activity meets or exceeds a lower activity threshold. If the total activity does not meets or exceeds the lower activity threshold, the accelerometer data can be determined to contain no valid step activity and no steps are counted in the block of accelerometer data.

However, if the total activity meets or exceeds the lower activity threshold (e.g., measurement of low-amplitude activity), the block of accelerometer data can be enhanced, 612-622. For example, the total accelerometer data can be enhanced. The lower activity threshold can enable a further distinction between true steps (e.g., slow walking) and false steps (e.g., driving) in the accelerometer data.

Accelerometer data enhancement can be performed based on the total activity and in various examples, energy expenditure. In various examples comprising two blocks of accelerometer data as illustrated in FIGS. 7A-B, the enhancement can be performed independently for blocks P1 and P2. Accelerometer data enhancement can enhance the periodicity in the accelerometer data where true steps may have introduced additional artifacts which are distinguishable from false steps based on the enhancement.

Referring back to FIG. 6, the lower total activity threshold can be adjusted based on the block of accelerometer data evaluated, 612. Thereafter, the acceleration data can be mean adjusted for further computations as illustrated in Equation 6 thereby creating mean adjusted acceleration data (inpZM$_0$), 614.

$$Acc_{total,i} = Acc_{sqr,i} - \overline{Acc_{sqr,i}} \qquad \text{Equation 6}$$

The mean adjustment can be done independently for each block in the accelerometer data (e.g., P1 and P2 as illustrated in FIGS. 7A-B). The absolute value of the mean adjusted accelerometer data can be calculated, 616.

The absolute accelerometer data can be processed through a low pass filter (LPF). Namely, the absolute value can be determined followed by a five-point moving average filter as a means of envelope detection as illustrated in Equation 7, 618.

$$X_i = \frac{1}{5}\sum_{j=0}^{4} x_{i-j} \qquad \text{Equation 7}$$

where $X_i$ denotes the $i^{th}$ output sample and $x_i$ denotes the $i^{th}$ input sample.

The low pass filtered accelerometer data can then be processed through a high pass filter (HPF), 620. For example, a $4^{th}$-order non-recursive high pass filter can be utilized on the accelerometer data to remove drift as illustrated in Equation 8.

$$X_i = 0.5x_i - 0.5x_{i-4} \qquad \text{Equation 8}$$

where $X_i$ denotes the $i^{th}$ output sample and $x_i$ denotes the $i^{th}$ input sample.

The high pass filtered accelerometer data can be scaled, 4622 and utilized as input for the computation of the auto-correlation.

FIG. 8 illustrates an example of enhancing accelerometer data to determine whether steps are being taken or if the accelerometer data is indicative of other activity. Namely, the raw accelerometer data 802 from the accelerometer can be transformed into processed accelerometer data 804 by taking the processing the raw accelerometer data 802 through an absolute value filter and a low pass filter (e.g., envelope detection). The processed accelerometer data 804 can be further transformed into enhanced accelerometer data 806 by processing the accelerometer data 804 a high pass filter (e.g., drift removal), mean normalization, and smoothing. The steps shown in FIG. 8 can be performed in any order. Thereafter, the step count algorithm can extracts features from the enhanced signal.

Referring back to FIG. 6, as illustrated accelerometer data that is mean adjusted at 624 (inpZM) or signal enhanced data from 622 (inpZM) can be transformed in auto-correlation data (e.g., AC, aCorr), 626. The auto-correlation data at lag t is described in Equation 9. The number of lags, t, of auto-correlation which are computed can be governed by the parameter the ACC_AC_LIM as described in Table 2.

$$AC(t) = \frac{\vec{x}_{1:N-t} \cdot \vec{x}_{t:N}}{\|\vec{x}_{1:N-t}\| \|\vec{x}_{t:N}\|}, \text{ where } \vec{x}_i = Acc_{total,i} \qquad \text{Equation 9}$$

In various examples comprising two blocks of acceleration data, the auto-correlation can be computed independently for each block (e.g., blocks P1 and P2 in FIGS. 7A-B). The mean adjustment of the input and the normalization of the output can imply that AC(t) represents the auto-covariance at lag t, even though the term auto-correlation can be used to describe this quantity.

The step count algorithm can calculate the number of level crossings (numLC) in the auto-correlation data, 628. A level crossing is when the signal in the data crosses and a level crossing threshold. Upward and downward level crossings of the auto-correlation data can be counted independently. The level crossings in the auto-correlation data can be determined according to the state machine illustrated in FIG. 9. The level crossings can be used to determine whether the block of acceleration data contains valid step activity, 630. For example, the step count algorithm can evaluate whether or not the number of level crossings meets or exceeds a level crossing threshold (numLCThresh). If the number of level crossings in the acceleration data does not meet or exceed the level crossing threshold, the accelerometer data can be determined to not have valid step activity and no steps are counted.

If the number of level crossings meets or exceeds the level crossing threshold, the number of level crossings (numZC) are counted in the accelerometer data that is mean adjusted at 4624 (inpZM) or signal enhanced data from 4622 (inpZM), 632. In various examples, at step 632, the level crossings can be zero crossings (e.g., the threshold is 0) or the number of level crossings can be different than zero crossings (e.g., the threshold is a non-zero number). A zero crossing is when the signal in the data changes sign (e.g., goes from positive to negative or vice versa). In acceleration data which is considered to contain valid step activity, the step count algorithm can calculate the number of steps based on the total number of level crossings in the mean adjusted acceleration data (inpZM). The level crossings in the accelerometer data (inpZM) can be determined according to the state machine illustrated in FIG. 9. Upward and downward level crossings can be counted independently as illustrated by the state machine in FIG. 9, thus the total step count can be divided by 2 to determine actual step counts. For example, each step of the patient comprises physically lifting up his/her foot (generating a downward crossing), followed by bringing down his/her foot back to the ground (generating an upward crossing). Thus, an upward/downward crossing pair constitute one step.

The step count algorithm can create output data comprising output values (e.g., physiological metrics) derived from the accelerometer data and the raw accelerometer data itself as an accelerometer record (ACR). The ACR can be structured as shown in Table 4 herein. The ACR can be stored in the memory 112 of the wearable device 102 (e.g., onboard flash memory) and/or a remote device.

Referring to FIGS. 7A-B, the mean of acceleration data in each of the axis (X, Y, Z) can be calculated by the step count algorithm and the mean acceleration data can be reported as an output value in floating point according to Equation 10. Mean acceleration data can be used as an input to the body angle algorithm and can be also used for calculating standard deviation metrics. These metrics may be computed only once per measurement period for the accelerometer data.

$$\bar{x} = \frac{1}{N}\sum_{i=1}^{N} x_i \text{ (For each } X, Y, Z)\quad \text{Equation 10}$$

N=the number of samples

Standard Deviation of acceleration data in each of the axis (X, Y, Z) can be calculated by the step count algorithm and reported as an output metric in floating point as illustrated in Equation 11. The standard deviation of acceleration data can be computed once per measurement period for both P1 and P2 blocks of accelerometer data.

$$\sigma_x = \sqrt{\frac{1}{N}\sum_{i=1}^{N}(x_1 - \bar{x})^2} \text{ (For each } X, Y, Z)\quad \text{Equation 11}$$

$\bar{x}$=the mean acceleration (in the dimension of interest)
N=the number of samples The energy expenditure (EE) can be calculated by the step count algorithm as the summation of the absolute value of all negative values in the total acceleration vector according to Equation 12. The EE can be computed independently for blocks P1 and P2, resulting in two floating point values. EE can be used to determine whether a block contains valid step activity, and also to determine whether signal enhancement of the accelerometer data should occur.

$$EE = \sum_{i=1}^{N} |Acc_{total,i}|, \text{ for } Acc_{total,i} < 0 \quad \text{Equation 12}$$

Where N=the number of samples

As illustrated in FIGS. 7A-B, the total acceleration, total activity, energy expenditure, and auto-correlation information from blocks P1 and P2 can be combined to produce a single step count number (UINT16 value) for every measurement period. The step count algorithm can comprise the following steps: (i) determining whether a block qualifies as a moderate-to-high amplitude or low amplitude activity block, (ii) performing signal enhancement on the low amplitude activity blocks, (iii) determining whether a block contains valid step activity, and (iv) counting the number of steps in a valid block. The steps counts from blocks P1 and P2 are simply added up to determine the total number of steps in a given measurement period. Computing steps independently for blocks P1 and P2 allows for finer granularity in tracking user step counts.

A block (P1 or P2) is declared to have valid step activity if both of the following conditions are satisfied (i) Total activity in the block exceeds threshold "the accelerometer Total Activity Low Threshold" and (ii) The number of level crossings of the auto-correlation exceeds threshold "the accelerometer Num Crossing".

For a block which satisfies the conditions enumerated above, the number of steps are calculated as the total number of level crossings of the total acceleration data. The step counts from blocks P1 and P2 are added up to produce the total number of steps in a measurement period. This number is then scaled appropriately to determine the adjusted step count (i.e. AStepCount), which is an approximate measure of steps per minute. The adjusted step count can be used as an input to algorithms implemented on the wearable device and/or the remote device.

The wearble device 102 can contain a scheduler (e.g., a software module external to the step count algorithm) that starts and stops acquisition of accelerometer data according to the accelerometer Interval and/or the accelerometer Duration parameters which can be programmable parameters. The accelerometer can acquire data at a fixed sampling rate (e.g., 12.5 Hz) for the length of the accelerometer Duration parameter set.

In various examples, the step count algorithm can comprise additional evaluations, such as, for example, minimum and/or maximum value, a time interval between detected steps, and amplitude variation between detected steps evaluation. The step count algorithm can use at least one of the following optional features, process each axis separately instead of combining into a total acceleration, use a reference vector to determine orientation of patch before deciding which axis/axes to use, and tune thresholds based on more physiological data, combine data from two axes. The step count algorithm can be ±3% accurate for normal walking (80 to 150 steps per minute) and ±10% accurate for slow walking (15 to 80 steps per minute) as measured over at least 1000 steps. In various examples, the step count algorithm can be ±5% accurate for slow walking (15 to 80 steps per minute) as measured over at least 1000 steps.

Referring to FIGS. 10A-E, the step count algorithm may provide more accurate step counts than a comparative algorithm. Dashed lines in FIGS. 10A-E represent activity thresholds. As shown in the slow walking example of FIG. 10C, the step count algorithm has enhanced the data such that the level crossings in the auto-correlation data produced by slow walking can result in a more accurate step count.

Figure 10B:
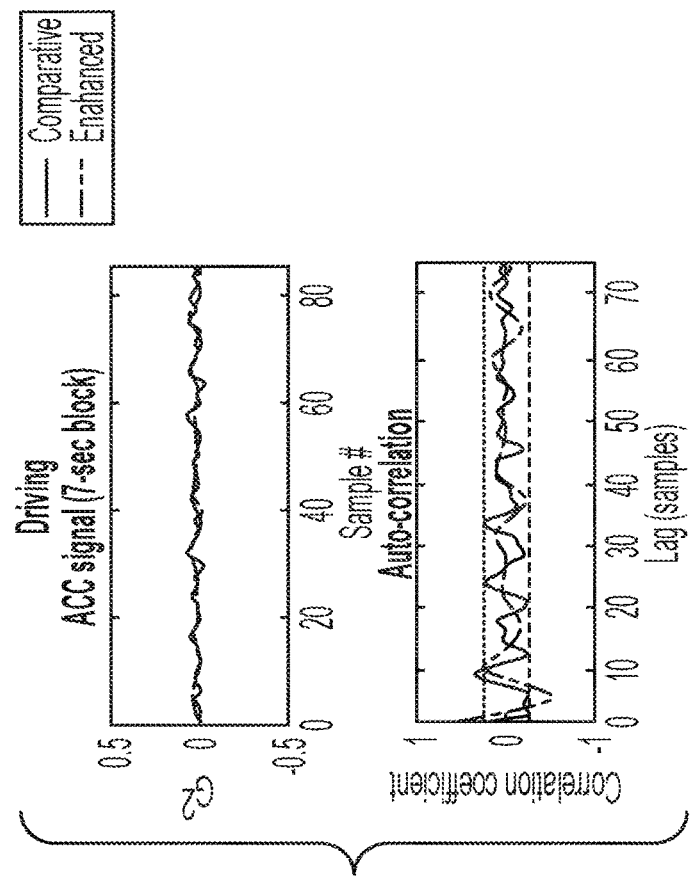
Figure 10A:
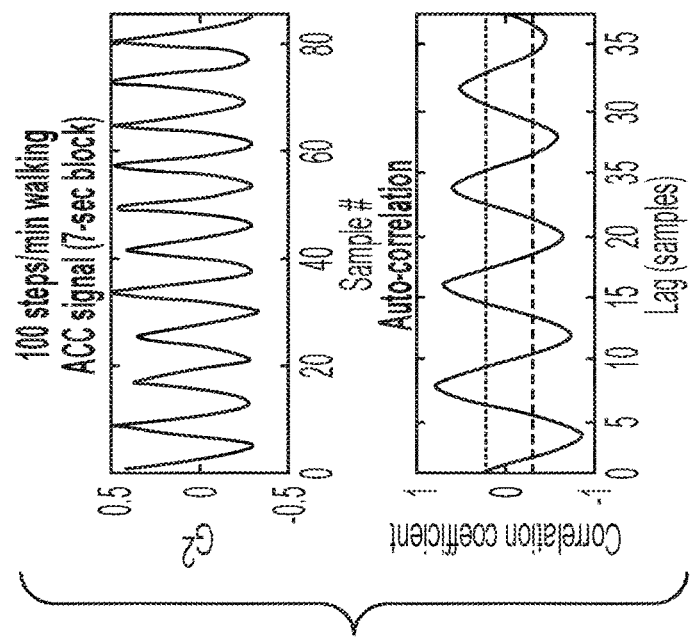
Figures 10C, 10D, 10E:
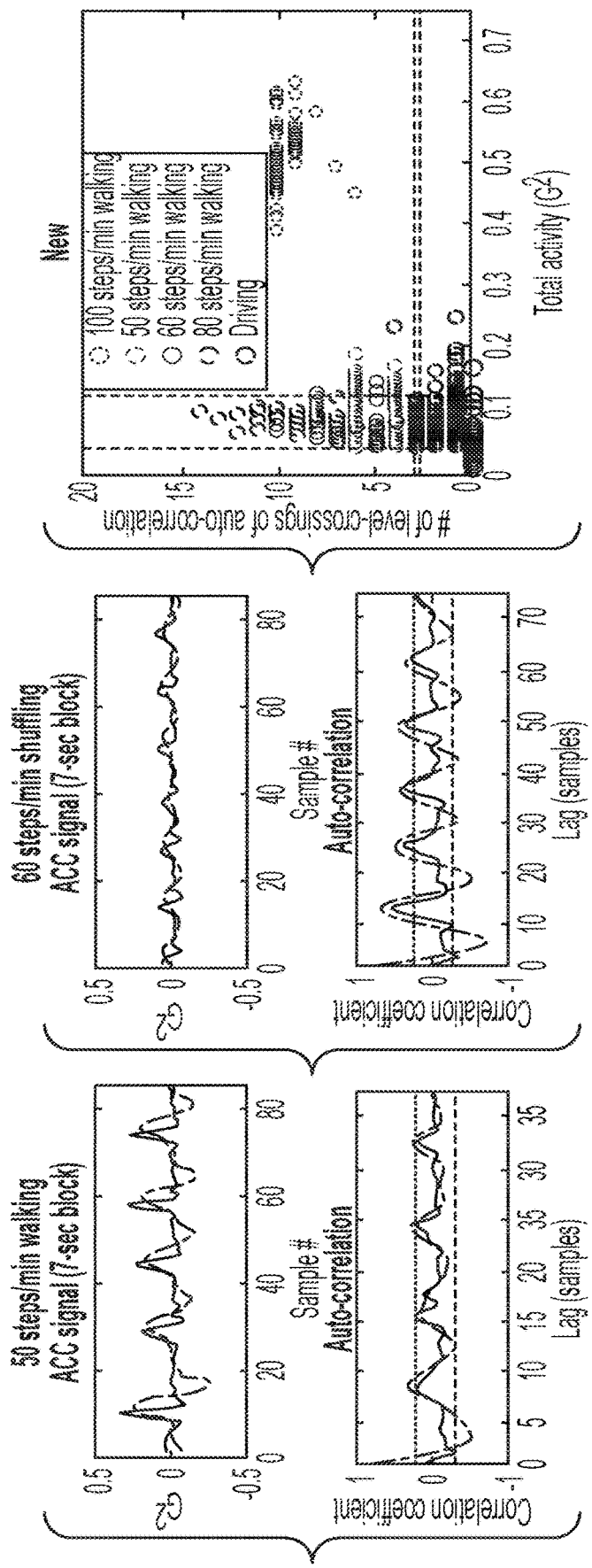

FIG. 10E illustrates the step count values as determined by a comparative algorithm and the step count algorithm from accelerometer data from normal walking, slow walking, slow shuffling, and driving. The normal walking 100 steps per minute data was sampled over 4 minutes with an expectation of a value of 400 steps for the step count; the slow walking 50 steps per minute data was sampled over 4 minutes with an expectation of a value of 200 for the step count; the slow shuffling 60 steps per minute data was sampled over 4 minutes with an expected value of 240 for the step count; the medium-paced shuffling 80 steps per minute data was sampled over 4 minutes with an expected value of 320 for the step count; and the driving data (e.g., 0 steps per minute) was sampled over various times with an expected value of 0 for the step count.

FIG. 10E is a plot of points of step data where each point represents one seven second block of accelerometer data that consisted only of the respective activity as identified in FIG. 10E that has been analyzed by the step count algorithm. FIG. 10E illustrates the activity threshold 4402 and the lower activity threshold 4404. As illustrated, the lower activity thresholds 4404 enables the detection of slow walking.

Additionally, the thresholds for the step count algorithm can be adjusted as shown in FIGS. 11A-C. The are in upper right of the plot of each of FIGS. 11A-C illustrates that by adjusting the thresholds, false step counts while driving may be limited, if not prevented by the step count algorithm.

As shown in FIG. 12A, acceleration data in the form of a periodic signal is produced from walking and the data is auto-correlated to produce the auto-correlated data shown in FIG. 12B. Additionally, FIGS. 13A-13B illustrates the auto-correlation data for different activities such as, for example, walking, driving, and sitting produced with the step count algorithm.

The step count algorithm was tested and results were reported as shown in the following tables. Namely, Tables 5-8 illustrate step counts from a wearable device placed on patients with the accelerometer data processed utilizing a comparative algorithm and the step count algorithm during different activities. Additionally, results of comparative pedometer 1 are illustrated. Table 5 illustrates the results of a wearable device placed on the left side of patients, Table 6 illustrates the results of a wearable device placed on the medial side of patients, Table 7 illustrates the results of a wearable device placed on the right side of patients, and Table 8 illustrates the results of a wearable device placed on the lateral side of patients.

TABLE 5

| | | | | Left side of patients | | |
|---|---|---|---|---|---|---|
| Activity | Duration (mins) | Comparative Pedometer 1 (left side) | Comparative Algorithm 1 | Comparative Algorithm 2 (MATLAB) | Comparative Algorithm 3 (MATLAB) | Inventive Algorithm (MATLAB) |
| Sitting | 72 | 0 | 0 | 0 | 0 | 0 |
| Walking | 40 | 4575 | 4565 | 4690 | 4690 | 4581 |
| Driving (freeway) | 24 | 0 | 147 | 151 | 0 | 0 |
| Driving (street) | 14 | 0 | 155 | 146 | 0 | 0 |
| Elliptical | 23 | 3144 | 3052 | 3176 | 3147 | 3090 |
| Treadmill | 13 | 1576 | 1618 | 1681 | 1655 | 1602 |
| Stationary bike | 16 | 1672 | 2668 | 2758 | 530 | 2571 |
| Around the house | 54 | 117 | 345 | 328 | 25 | 94 |

TABLE 6

| | | | | Medial side of patients | | |
|---|---|---|---|---|---|---|
| Activity | Duration (mins) | Comparative Pedometer 1 (left side) | Comparative Algorithm 1 | Comparative Algorithm 2 (MATLAB) | Comparative Algorithm 3 (MATLAB) | Inventive Algorithm (MATLAB) |
| Sitting | 27 | 0 | 0 | 0 | 0 | 0 |
| Walking | 28 | 2577 | 2617 | 2693 | 2649 | 2615 |
| Walking | 40 | 1463 | 1744 | 1796 | 1354 | 1463 |
| Driving (freeway) | 27.5 | 0 | 335 | 324 | 0 | 0 |
| Driving (street/freeway) | 55 | 0 | 91 | 61 | 0 | 0 |
| Driving | 21 | 0 | 109 | 111 | 0 | 0 |
| Driving | 18.5 | 0 | 244 | 252 | 0 | 0 |
| Around office | 242 | 656 | 890 | 910 | 437 | 612 |
| Around the house | 10 | 20 | 63 | 67 | 27 | 22 |

TABLE 7

Right side of patients

| Activity | Duration (mins) | Comparative Pedometer 1 (right side) | Comparative Algorithm 1 | Comparative Algorithm 2 (MATLAB) | Comparative Algorithm 3 (MATLAB) | Inventive Algorithm (MATLAB) |
|---|---|---|---|---|---|---|
| Sitting | 72 | 0 | 0 | 0 | 0 | 0 |
| Walking* | 40 | 4556 | 4533 | 4742 | 4742 | 4659 |
| Driving (freeway) | 24 | 0 | 101 | 76 | 0 | 0 |
| Driving (street) | 14 | 0 | 87 | 87 | 0 | 0 |
| Elliptical** | 23 | 3143 | 3026 | 3127 | 3109 | 3067 |
| Treadmill** | 13 | 1442 | 1578 | 1636 | 1623 | 1597 |
| Stationary bike** | 16 | 1430 | 2364 | 2452 | 0 | 1995 |
| Around the house | 54 | 151 | 188 | 193 | 0 | 46 |

TABLE 8

Lateral side of patients

| Activity | Duration (mins) | Comparative Pedometer 1 (right side) | Comparative Algorithm 1 | Comparative Algorithm 2 (MATLAB) | Comparative Algorithm 3 (MATLAB) | Inventive Algorithm (MATLAB) |
|---|---|---|---|---|---|---|
| Sitting | 27 | 0 | 0 | 0 | 0 | 0 |
| Walking | 28 | 2599 | 2609 | 2678 | 2630 | 2558 |
| Walking | 40 | 1404 | 1799 | 1834 | 1398 | 1350 |
| Driving (freeway) | 27.5 | 0 | 391 | 388 | 0 | 0 |
| Driving (street/freeway) | 55 | 0 | 67 | 68 | 0 | 12 |
| Driving | 21 | 5 | 98 | 106 | 0 | 16 |
| Driving | 18.5 | 0 | 81 | 73 | 0 | 0 |
| Around office | 242 | 629 | 909 | 930 | 506 | 580 |
| Around the house | 10 | 20 | 68 | 71 | 23 | 28 |

The comparison between Tables 5 and 7 show that the step counts output from the wearable device on the left side of patients and the right side of the patients were comparable and indicate that the placement of the patch may not have an effect on the step count and that the step count algorithm can reproducibly count steps. The comparison between Tables 6 and 8 show that the step counts reported from the wearable device on the medial side of patients and the lateral side of the patients were comparable and indicate that the placement of the patch may not have an effect on the step count and that the step count algorithm can reproducibly count steps.

Tables 9 through 14 illustrate the step count values output from the comparative algorithms, comparative pedometer 1, and the step count algorithm on various patients.

TABLE 9

| | | Patient 1 | | | |
|---|---|---|---|---|---|
| Activity | Duration (mins) | Comparative Pedometer 1 | Comparative Algorithm 1 | Comparative Algorithm 2 (MATLAB) | Inventive Algorithm (MATLAB) |
| Driving (street) | 9 | 0 | 29 | 26 | 0 |
| Driving (freeway) | 11 | 0 | 78 | 81 | 0 |
| Visit to gym* | 60 | 2494 | 2836 | 2893 | 2443 |

TABLE 10

| | | Patient 2 | | | |
|---|---|---|---|---|---|
| Activity | Duration (mins) | Comparative Pedometer 1 | Comparative Algorithm 1 | Comparative Algorithm 2 (MATLAB) | Inventive Algorithm (MATLAB) |
| Driving (street) | 9 | 0 | 73 | 44 | 0 |
| Driving (freeway) | 11 | 0 | 179 | 186 | 0 |
| Visit to gym* | 60 | 2780 | 2891 | 2996 | 2604 |

*Includes walk to the gym and back, and 2 min spurts of various gym activities, interspersed with rest

TABLE 11

| | | Patient 3 | | | |
|---|---|---|---|---|---|
| Activity | Duration (mins) | Comparative Pedometer 1 | Comparative Algorithm 1 | Comparative Algorithm 2 (MATLAB) | Inventive Algorithm (MATLAB) |
| Driving (street) | 9 | 0 | 79 | 134 | 0 |
| Driving (freeway) | 11 | 0 | 91 | 96 | 0 |
| Visit to gym* | 60 | 2747 | 3150 | 3254 | 2769 |

TABLE 12

| | | Patient 4 | | | |
|---|---|---|---|---|---|
| Activity | Duration (mins) | Comparative Pedometer 1 | Comparative Algorithm 1 | Comparative Algorithm 2 (MATLAB) | Inventive Algorithm (MATLAB) |
| Driving (street) | 9 | 0 | 63 | 49 | 0 |
| Driving (freeway) | 11 | 0 | 78 | 82 | 0 |
| Visit to gym* | 60 | 2613 | 2679 | 2761 | 2339 |

*Includes walk to the gym and back, and 2 min spurts of various gym activities, interspersed with rest

TABLE 13

| | | Patient 5 | | | |
|---|---|---|---|---|---|
| Activity | Duration (mins) | Comparative Pedometer 1 | Comparative Algorithm 1 | Comparative Algorithm 2 (MATLAB) | Inventive Algorithm (MATLAB) |
| Driving (street) | 9 | 0 | 77 | 78 | 0 |
| Driving (freeway) | 11 | 0 | 111 | 116 | 0 |
| Visit to gym* | 60 | 2655 | 2779 | 2874 | 2232 |

TABLE 14

| | | Patient 6 | | | |
|---|---|---|---|---|---|
| Activity | Duration (mins) | Comparative Pedometer 1 | Comparative Algorithm 1 | Comparative Algorithm 2 (MATLAB) | Inventive Algorithm (MATLAB) |
| Driving (street) | 9 | 0 | 38 | 39 | 0 |

TABLE 14-continued

Patient 6

| Activity | Duration (mins) | Comparative Pedometer 1 | Comparative Algorithm 1 | Comparative Algorithm 2 (MATLAB) | Inventive Algorithm (MATLAB) |
|---|---|---|---|---|---|
| Driving (freeway) | 11 | 0 | 48 | 49 | 0 |
| Visit to gym* | 60 | 2542 | 2883 | 2970 | 2477 |

*Includes walk to the gym and back, and 2 min spurts of various gym activities, interspersed with rest Tables 5 to 14 illustrate the step count algorithm according to the present disclosure can have an improved accuracy for step counting while minimizing false step counts during driving.

The step count algorithm can have an accuracy of +/−10% or +/−12 steps per minute, whichever is greater, for step counting compared to a manual counting of the steps. The step count algorithm can have an accuracy of +/−3% of the steps, compared to a known step reference, over an input range of 80 to 150 steps per minute or 80 to 180 steps per minute, measured over greater than or equal to 1,000 simulated steps. In various examples, the step count algorithm can have an accuracy that is equal to or better than JIS S72000-1993 Japanese pedometer standard which is hereby incorporated by reference.

Table 15 illustrates the step count value as output by a comparative algorithm that analyzed acceleration data at various step rates.

TABLE 15

Comparative algorithm

| Patch # | Rate (Steps Per Minute) | | | | | | |
|---|---|---|---|---|---|---|---|
|  | 60 | 80 | 90 | 100 | 120 | 150 | 180 |
| 1 | 1000 | 975 | 998 | 973 | 964 | 993 | 972 |
| 2 | 950 | 981 | 967 | 974 | 983 | 987 | 980 |
| 3 | 951 | 978 | 988 | 977 | 983 | 967 | 978 |
| 4 | 967 | 976 | 967 | 971 | 975 | 980 | 961 |
| 5 | 1008 | 974 | 967 | 978 | 992 | 983 | 969 |
| 6 | 967 | 979 | 967 | 977 | 983 | 993 | 974 |
| 7 | 983 | 973 | 989 | 978 | 975 | 987 | 967 |
| 8 | 952 | 979 | 978 | 978 | 983 | 980 | 983 |
| 9 | 983 | 973 | 978 | 974 | 967 | 983 | 994 |

Table 16 illustrates the step count value output from the step count algorithm according to the present disclosure that analyzed acceleration data at various step rates.

TABLE 16

Inventive algorithm

| Patch # | Rate (Steps Per Minute) | | | | | | |
|---|---|---|---|---|---|---|---|
|  | 60 | 80 | 90 | 100 | 120 | 150 | 180 |
| 1 | 1000 | 1003 | 1011 | 996 | 983 | 993 | 1003 |
| 2 | 1017 | 1005 | 1011 | 997 | 1008 | 1007 | 1000 |
| 3 | 1050 | 1005 | 1011 | 995 | 992 | 1002 | 994 |
| 4 | 1017 | 1002 | 1011 | 996 | 993 | 1000 | 994 |
| 5 | 1017 | 1010 | 1000 | 993 | 998 | 993 | 1000 |
| 6 | 1033 | 1008 | 1011 | 999 | 992 | 993 | 1000 |
| 7 | 1017 | 1001 | 989 | 991 | 1000 | 1000 | 994 |
| 8 | 1028 | 1007 | 989 | 998 | 992 | 1007 | 1006 |
| 9 | 1039 | 1002 | 989 | 1001 | 992 | 993 | 999 |

Table 17 illustrates the step count value output from the step count algorithm according to the present disclosure that analyzed acceleration data at various step rates while oriented at 45° during measurement.

TABLE 17

Inventive algorithm oriented at 45°

| Patch # | Rate (Steps Per Minute) | | | | | | |
|---|---|---|---|---|---|---|---|
|  | 60 | 80 | 90 | 100 | 120 | 150 | 180 |
| 1 | 1017 | 1003 | 1000 | 994 | 992 | 1007 | 994 |
| 2 | 1016 | 1010 | 989 | 999 | 1000 | 997 | 986 |
| 3 | 1050 | 1008 | 1000 | 1001 | 992 | 1000 | 994 |
| 4 | 1017 | 1007 | 989 | 995 | 1000 | 989 | 1006 |
| 5 | N/A | N/A | 1000 | 999 | 992 | 987 | 983 |
| 6 | 1017 | 1009 | 1011 | 1001 | 1008 | 987 | 997 |
| 7 | 1033 | 1004 | 1011 | 995 | 992 | 1000 | 994 |
| 8 | 1000 | 1001 | 1000 | 994 | 1000 | 1000 | 1011 |
| 9 | 1049 | 1005 | 1011 | 995 | 1008 | 993 | 994 |
| 10 | 1033 | 1003 | 1011 | 996 | 1000 | 993 | 989 |

Tables 16 and 17 comprise substantially similar results showing that the orientation of the patch may have a minimal effect on the step count.

Table 18 illustrates the summary of various metrics of Tables 15 to 17 computed over the 80 to 150 steps per minute or 80 to 180 steps per minute range. The bias, absolute error, and variation in error are lower for the step count algorithm according to the present disclosure versus the comparative algorithm. Additionally, the step count algorithm according to the present disclosure improves overall performance of the wearable device.

TABLE 18

Summary of metrics

| Algorithm* | Mean error (%) | Mean abs error (%) | Std dev of error (%) |
|---|---|---|---|
| Comparative | −2.22% | 2.22% | 0.82% |
| Inventive | −0.076% | 0.56% | 0.69% |
| Inventive @ 45° | −0.012% | 0.57% | 0.72% |

The step count algorithm according to the present disclosure overall provides a more accurate step count as measured by the number of data points that have an accuracy of equal to or less than +/−3%.

FIG. 14 illustrates a plot of reported steps count rates of various patients as output by various pedometers and the wearable device comprising a comparative algorithm and the step count algorithm according to the present disclosure. The patients 1-12 wore the wearable device. As illustrated, most devices performed well at 100 steps per minute. However, the step count algorithm according to the present disclosure on the wearable device outperformed the other devices comprising comparative algorithms at 50 steps per minute walking while minimizing false step counts from driving.

When an accelerometer doesn't have an external clock (X-Tal) and there are no trim settings, variation in the sampling rate can occur. In various examples, there may be some sampling rate variation across different wearable devices. The variation across the different wearable devices can lead to a perceived shift in input frequency (e.g., step rate) and hence can be reported as different step rates. The step count algorithm can factor the sampling rate into the step rate calculation.

Boundary Effects

The wearable device can handle discontinuous data such as, for example, discontinuous data 1500 as illustrated in FIG. 15 comprising frames of ingestible sensor data 1504 and frames of physiological data 1502 of the patient interspersed in time gaps 1506 between the frames of the ingestible sensor data 1504. For example, the wearable device can receive the ingestible sensor data 1504 serially with the physiological data 1502. The discontinuous data can create some inaccurate readings due to boundary effects caused by switching from one type of the data to the other (e.g., physiological data to ingestible sensor data and/or ingestible sensor data to physiological data), which may result in an inaccurate physiological metric (e.g., step count, heart rate, heart rate variability, body angle).

For example, FIG. 16 illustrates a first sub-frame of acceleration data on the left and a second sub-frame of acceleration data on the right. The first and second sub-frames are parts of a single frame that have been received in a discontinuous manner by the wearable device. As illustrated, the single frame can be 14 second frame of accelerometer data and each frame can be broken into smaller sub-frames (e.g., a 7 second portion of the 14 second frame), which may improve accuracy of the accelerometer data and facilitate the serial communication of different data types.

Since, the sub-frames have been received and may be processed in a disjointed manner, boundary effects at the start and end of each frame may occur. The circles in FIG. 16 illustrate level crossings which are counted by the step count algorithm to get half-steps. A missed level crossing at sub-frame boundary can lead to a missed half-step (e.g., an inaccurate step count). As illustrated in FIG. 16, a level crossing has been missed between the end 1602 of the first sub-block (e.g., near sample index 90) and the beginning 1604 of the second sub-block (e.g., near sample index 0) as a result of boundary effects and the configuration of the discontinuous data. In various examples, the level crossing can be a zero crossing (e.g., the threshold level is zero) or the level crossing can be a crossing further than a zero crossing (e.g., the threshold is a non-zero number).

To handle the boundary effects, various measures can be taken. As discussed herein, the step count can be based on counting level crossings (e.g., one level crossing counts as a half step) and the heart rate determination and heart rate variability can be determined based on counting peaks. An upward level crossing can be defined as going from negative values to positive values on the Y-axis until or greater than an upward threshold. A downward level crossing can be defined as going from positive values to negative values on the Y-axis until or greater than a downward threshold. In order to handle boundary effects, one measure can be if the last level crossing of a first sub-frame and the initial level crossing of a second sub-frame are of the same type (i.e. both upward or both downward), the step count algorithm can increment the step count by a half step. Additionally, the step count algorithm can comprise an extended precision value of step count to account for half steps in the step rate calculation.

FIG. 17 show an example of a boundary effects in a frame of accelerometer data that may affect step count when discontinuous data is received by the wearable device. As illustrated, the first sub-frame and the second sub-frame are each a seven second portion of a 14 second data block of total acceleration data. The circles in FIG. 17 illustrate level crossings which are counted to get half-step counts. Not counting the partial half-step 1706 at the beginning of the first sub-frame and/or the end of the second sub-frame 1708 can lead to an inaccurate step count (e.g., an underestimation of the step count).

In order to handle boundary effects, before the first level crossing or after the last level crossing in a sub-frame or frame, if there is a slope change (e.g., a change in the sign of the slop, computed as x[n]−x[n−1]) of the physiological data, the step count algorithm can add a half-step. The area 1810 in FIG. 18 illustrates a slope change. Responsive to the slope change, the step count algorithm can add a half-step. In general, the measures to handle boundary effects can be applied to other devices that similarly handle different types of data serially, resulting in discontinuous data collection. Additionally, the measured for handling boundary effects in accelerometer data apply to other types of physiological data, such as, for example, ECG data.

To demonstrate the accuracy of the step count algorithm, a wearable device comprising the step count algorithm was used to output a step count via the firmware and the acceleration data from the wearable device was also post-processed in MATLAB to determine if any steps may have been missed. The wearable device was collecting output values (e.g., physiological metrics) derived from the accelerometer data and the raw accelerometer data. The MATLAB model analysed the raw accelerometer data. As illustrated in FIG. 19, the step count values output from the step count algorithm processed on processor of the wearable device and a MATLAB model post-processing raw accelerometer data from the wearable device on a remote device matched perfectly.

Additionally, FIG. 20A, illustrates the total activity output from the step count algorithm over time (the step rate is indicated above the data in steps/min (e.g., 30, 60, 120, 150, 180, 210). The threshold for total activity can be set based on the lowest step rate that should be detected and measured by the wearable device. For example, for detecting a step rate of 60 steps/min and ignoring a step rate of 30 steps or less, a threshold in a range of 0.03 to 0.28 may be set based on the data illustrated in FIG. 20A. FIG. 20B illustrates raw acceleration data from an accelerometer at various step rates on the left (the step rate is indicated above the data in steps/min (e.g., 30, 60, 120, 150, 180, 210) and acceleration data that has been box car filtered on the right. The sampling frequency was 12.5 Hz, the nyquist frequency was 6.25 Hz, and the boxcar filter length was 2 with a 3 dB cutoff at 3.2 Hz. As illustrated at the 210 steps per minute step rate, the box-car filter may blur some of the steps (e.g., two steps counted as one) of the data due to the length of the filter and the frequency of the steps measured. However, a sufficient amount of signal gets through the box-car filter to make a measurement at 210 steps per minute.

Body Angle

The wearable device 102 can comprise functionality for automatically determining an orientation of the wearable device relative to the body of a patient utilizing the detected physiological data. The determination may not require the patient to initialize and/or calibrate the wearable device 102. Thus, the wearable device 102 may be installed in various orientations, such that the wearable device 102 may not require exact placement of the wearable device 102 on the skin of the patient in a particular position and/or orientation. For example, the wearable device 102 could be right side up, upside down, or in other orientations.

The body angle algorithm can determine a body angle of the patient without any input from the patient that might typically be used to initialize a comparative pedometer. The body angle algorithm can further be used to determine whether the wearer is asleep and/or lying down as described herein. The body angle algorithm can enable the wearable device 102 to reduce power consumption during the time the patient is asleep and/or laying down since steps may not be taken while the patient is lying down. Additionally, the body angle algorithm can enable an efficient body angle determination after a power loss event in the wearable device 102.

The body angle algorithm can receive accelerometer data and can be distributed across a wearable device 102 and a remote device for execution by a control circuit. For example, the body angle algorithm can be stored in memory 112 and can be utilized by processor 111 to transform accelerometer data received from accelerometer 122 into a physiological metric, such as, for example, a body angle. The body angle algorithm can enable an orientation determination without an active calibration of the wearable device.

In various examples, the body angle algorithm can be stored and computed on a remote device and the accelerometer data used to calculate the body angle could be stored over longer periods of time which can offer an improvement in accuracy due to an increased time frame over which to exclude potentially erroneous body angle values.

Determination of a body angle can rely on a reference vector, which can be derived from the per-dimension mean acceleration data from the accelerometer. The reference vector can correspond to the orientation of the wearable device when the patient is upright (e.g., walking, standing), while the body angle can be the projection of the instantaneous mean acceleration vector from the acceleration data on the reference vector. As used herein, "lying down" means a position of the patient associated with a 0 degree body angle while "upright" means a position of the patient associated with a −90 degrees body angle.

The reference vector can be a output as a unitless quantity in floating point (one number per X, Y, Z dimension) and the body angle can be output in degrees. The reference vector can be updated once per measurement period after the number of measurement periods have exceeded ACC BA Num Records parameter. The body angle can be calculated once per measurement period and can rely on the most recently updated reference vector.

The reference vector calculation may use as input qualifying ACRs which comprise a step rate in a select range (e.g., between that parameters ACC BA Min Step Thr and ACC BA Max Step Thr). Thus, the reference vector calculation can assume the patient upright since the patient is taking steps at a step rate in the select range. The qualifying ACRs are binned based on their mean acceleration data. The binning can be done independently in for each of the axis (e.g., X, Y, Z) in the accelerometer data. Then the select bin in each of the axis with the most qualifying records (but may be no less than "ACC_MIN_MODE") can be set as the reference vector.

If the wearable device has not stored and/or received enough qualifying ACRs to set a reference vector, the wearable device can use a default vector (e.g., {−1,0,0}) under the nominal assumption that the X-axis of the accelerometer should be perfectly aligned with gravity when the patient is upright. In examples where the patient has placed the wearable device upside down on the body and a sufficient number of qualifying ACRs have not been collected (e.g., wearable device placed and the patient lies down), the wearable device can invert the reference vector (e.g., {1,0,0}). The wearable device can invert the reference vector if a majority of the ACRs have x-axis values greater than a threshold, such as, for example, greater than 0.8 g with a minimum of 3 ACRs. For example, the wearable device can assume that the wearable device has been placed upside down.

The reference vector updates can be frozen (e.g., no further updates) when the bin count reaches a bin count threshold (e.g., ACC_MAX_MODE) in any of the axis. Freezing the updates can optimize memory utilization so that the bin counts can be stored as 8-bit integers. Given that the orientation of the wearable device relative to the body of the user can be relatively fixed (except for some possible variation due to skin deformation), freezing the reference vector may not affect the accuracy of the reference vector.

As stated herein, the body angle algorithm can calculate the reference vector without having the patient position and/or orient the wearable device in a select position and/or orientation. In this way, the wearable device can be easier for a patient to use and automatically continue with body angle determinations in the event of a power loss.

The body angle algorithm can be configured to balance memory and accuracy of the reference vector as desired. For example, another parameter, ACC_NUM_BINS, can be used to trade-off memory requirements for accuracy. In this way, examples of the present disclosure can enable a decrease in chip size, a decrease in power consumption, and/or a decrease in clock speed.

FIGS. 21A-D illustrate an example of generation of a reference vector by filling bins with ACRs. The wearable device can be configured to perform the reference vector calculations. Upon start-up (e.g., initialization) of the wearable device, the reference vector bins can be empty. The number of bins can be based on default compile time parameters. In various examples, there can be 40 reference vector bins.

Figures 21A, 21B, 21C:
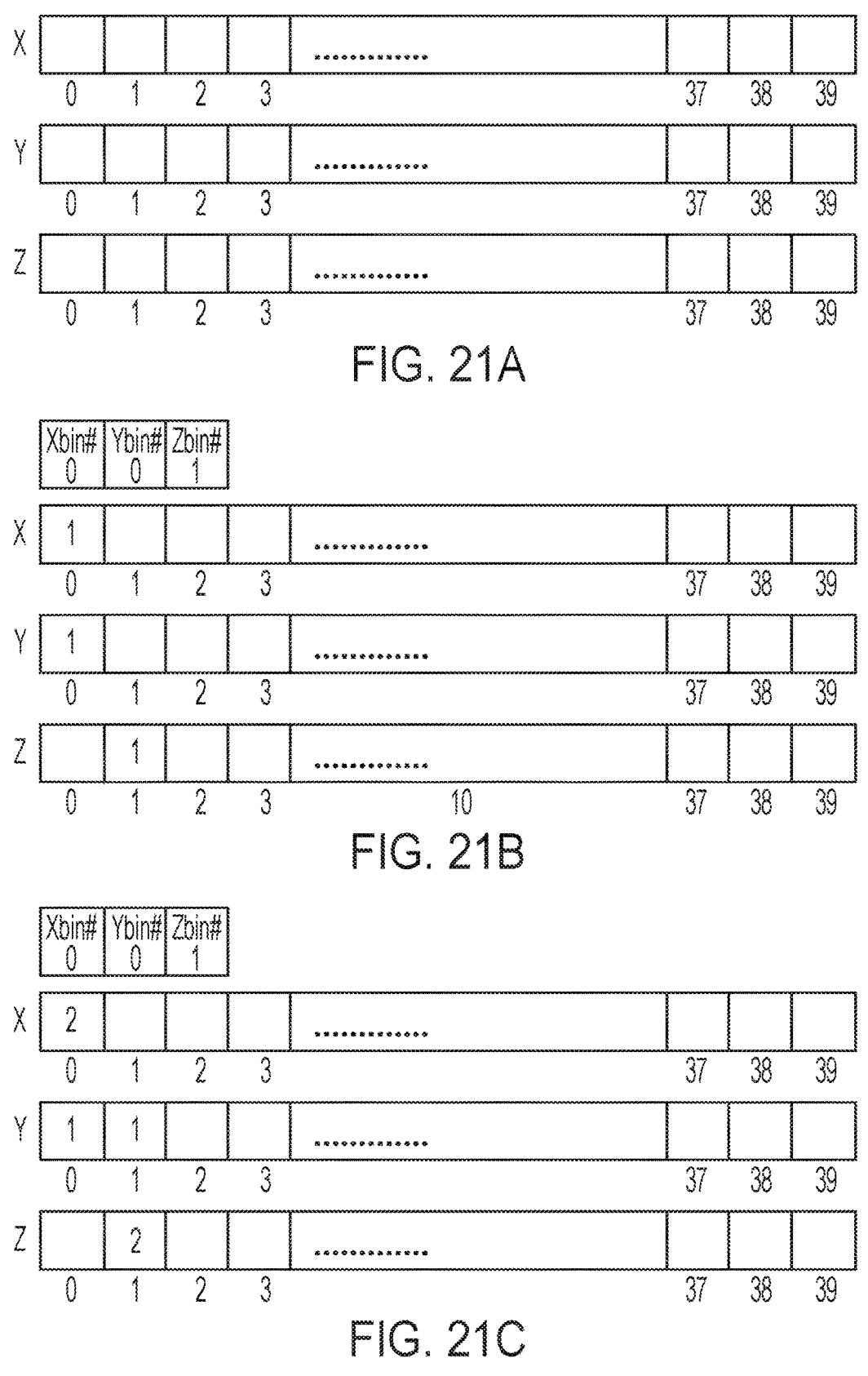

Referring to FIG. 21A, an initial state for the reference vector determination is illustrated in which the reference vector bins are empty. The default 40 reference vector bins are shown for the axis, X, Y, and Z. Acceleration data (e.g., an ACR) with step counts greater than "ACC BA Min Step Thr" and less than "ACC BA Max Step Thr" can be considered a qualifying record for the reference vector calculation and can be added to a reference vector bin. Upon receiving the qualifying record, the body angle algorithm can calculate the mean result of the acceleration data (e.g., packet of data). That is, the body angle algorithm can calculate the $X_{Bin\ \#}$ bin, $Y_{Bin\ \#}$ bin, and $Z_{Bin\ \#}$ bin based on the MeanX, MeanY, and MeanZ in the Equation 13. The $Y_{Bin\ \#}$ bin and $Z_{Bin\ \#}$ bin are calculated in a similar fashion to the $X_{Bin\ \#}$ bin.

$$X_{Bin\ \#} = ((MeanX - ACC\_BIN\_LOW)/ACC\_BIN\_WIDTH) \quad \text{Equation 13}$$

Where ACC_BIN_LOW=minimum value of the mean after normalization

ACC_BIN_WIDTH=Quantization size of a bin from −2 g to +2 g

The body angle algorithm can increment the count in the $X_{Bin\ \#}$ bin, $Y_{Bin\ \#}$ bin, and/or $Z_{Bin\ \#}$ bin based on the mean result of the acceleration data. Referring to FIG. 21B, a populated state of the reference vector bins is illustrated. As illustrated the count of qualifying acceleration data in the reference vector bins is provided. To determine the reference vector, the body angle algorithm can evaluate the reference vector bins of each axis and determine which reference vector bins in each axis contain the most counts relative to the other reference vector bins. In FIG. 21B, the reference vector may not yet be calculated by the body angle algorithm since there is only one qualifying record present in the reference vector bins of each axis. The body angle algorithm may only calculate the reference vector once a threshold number of records is reached (e.g., ACC BA Num Records). Waiting for a threshold number of records can increase the accuracy of the calculated reference vector. Additional qualifying records that are received can be added to the reference vector bins.

Referring to FIG. 21C, a second qualifying record has been received and populated in to the reference vector bins. There is a tie in the reference vector bins for the Y-axis. In examples where reference vector bins have a tie, the first reference vector bin that reaches the count will be selected. However, the threshold number of records (e.g., ACC BA Num Records) has not yet be reached (e.g., less than three qualifying records). Therefore, no reference vector bins have been selected for a reference vector calculation.

Referring to FIG. 21D, a third qualifying record has been received and populated into the reference vector bins. The threshold number of records (ACC BA Num Records) has been reached. Thus, the body angle algorithm can select the reference vector bins with the highest counts on each axis (as illustrated by the shaded bins) and the body angle algorithm can calculate the reference vector from the selected bins. As illustrated, the body angle algorithm selected XBin=0, YBin=0, and ZBin=1. Thereafter, the body angle algorithm can calculate the reference vector from Equation 14. The Reference Vector Y, and Reference Vector Z can be calculated in a similar fashion to Reference Vector X.

Reference Vector X=ACC_BIN_LOW+
((XBin−1.0)*ACC_BIN_WIDTH)+
(ACC_BIN_WIDTH/2.0)     Equation 14

Where ACC_BIN_LOW=minimum value of the mean after normalization

ACC_BIN_WIDTH=number of bins per X, Y, Z dimension

The reference vector can be a combination of the reference vectors for each axis. For example, the reference vector can be output as {Reference Vector X, Reference Vector Y, Reference Vector Z}. As additional qualifying records are received and populated into the reference vector bins, the counts in the reference vector bins can change which can result in a new maximum within each axis. Thus, the reference vector can be recalculated (e.g., updated) after each qualifying record is received. After a threshold amount of qualifying records have been received (ACC_MAX_MODE), the reference vector may be frozen and may not be recalculated.

After the reference vector is calculated or based on a default reference vector, in order to determine the body angle of the patient, the body angle algorithm can calculate a normalized projection of the mean acceleration vector on the reference vector according to Equation 15.

$$\text{Body Angle} = \arccos\left(\frac{\vec{m}\cdot\vec{r}}{\|\vec{m}\|\|\vec{r}\|}\right) - 90° \quad \text{Equation 15}$$

Where $\vec{m}$=mean acceleration vector $\vec{r}$=most recent reference vector

According to Equation 15, an acceleration vector aligned with the reference vector can result in a body angle of −90° (e.g., upright). An acceleration vector radially offset from the reference vector can result in a body angle of 0 degrees (e.g., lying down) or a body angle of 90 degrees (e.g., upside down.) The body angle can be quantized by the body angle algorithm or other software (embedded on the wearable device and/or on a remote device), and mapped to one of the possible states. In various examples, there may only be four possible states, upright, leaning, lying down, and upside down. In this way, the body angle algorithm can be used by the wearable device to lower power consumption (e.g., frequency of accelerometer measurements) during a particular state (e.g., lying down) since the patient will likely not be taking steps during the particular state.

Heart Rate

A heart rate of a patient can be determined by measuring the electrical activity of the heart caused by cardiac muscle depolarization and repolarization during a cardiac cycle. The electrical activity can be detected by placing electrodes on the body of a patient and detecting ECG signals (voltage versus time). ECG signals typically comprise, among others, a P-wave, a QRS complex, and a T-wave. The P-wave represents depolarization of the atria and typically occurs for 80 milliseconds (ms) or less. The QRS complex is a combination of a Q-wave (downward deflection after the P-wave), an R-wave (upward deflection following the Q-wave), and an S-wave (downward flection following the R-wave) that typically corresponds to the depolarization of the right and left ventricles of the human heart and contraction of the large ventricular muscles. The QRS complex typically occurs for 80 ms to 100 ms and typically has the largest amplitude in the ECG signal as represented by the R-wave peak. The T-wave follows the QRS complex and represents the repolarization of the ventricles which can typically occur for 160 ms.

Methods for determining a heart rate can focus on R-wave peak detection in ECG data and can assume reliably periodic and continuous data. For example, a heart rate metric of the patient can be calculated according to Equation 16. As used herein, the term "heart rate" means the median heat rate unless stated to the contrary. The mean heat rate may also be calculated, but median heart rate is the typical output.

$$HR_{median} = 60 * \frac{F_s}{d} \bigg/ \text{median } (RR) \quad \text{Equation 16}$$

where Fs=256 Hz, d=4 (down-sampling factor)

Given peak locations:

$\{P_n;\ n=1,2,\ldots,N\}$

R-R intervals are computed as:

$\{RR_n = P_n - P_{n-1}\}$

The R-R interval refers to the time between two adjacent R-wave peaks in the ECG signal. However, discontinuous data comprising frames of ingestible sensor data and physiological data can present challenges when determining a heart rate of a patient from ECG data. Namely, handling burst data from a wearable device and accurately determining a heat rate from ECG data can present challenges.

The heart rate algorithm can receive ECG data and can be distributed across a wearable device 102 and a remote device for execution by a control circuit. For example, the heart rate algorithm can be stored in memory 112 and can be utilized by processor 111 to transform ECG data into a physiological metric, such as, for example, a step count. In various examples, the vector co-processor portion of the heart rate algorithm can be stored in memory 112 of the wearable device and executed on the wearable device 102 and the processor portion of the heart rate algorithm can be stored in memory of the remote device and executed on the remote device. The processing of the ECG data on the patch can reduce the data that is transferred to a remote device for further processing.

FIG. 22A illustrates example data of a comparative algorithm for determining a heart rate from ECG data which is missing large blocks of data due to a patient sleeping or resting during a period of time as illustrated the body angle of the patient versus time in FIG. 22B (0 degrees corresponding to the patient lying down). The large blocks of data that are missing were filtered out utilizing a comparative quality filter. FIG. 22C illustrates three frames of a raw ECG signal which were filtered out with comparative quality. However, as illustrated, heart beats are still observable in the raw ECG signal.

In order to obtain an ECG metric, referring to FIG. 15, the physiological data 1502 can comprise ECG data for an ECG event duration during the time gaps 1506. The ingestible sensor data 1504 can be received in between ECG data (e.g., during the ECG measurement interval). A frame of ECG data can be a duration of an ECG signal acquisition and a sub-frame can be a portion of the frame. In various examples, each frame comprises 4 sub-frames.

A heart rate (HR) algorithm to process the ECG data can comprise the parameters in Table 19.

TABLE 19

| Parameter | Notes |
| --- | --- |
| ECG Measurement Interval | Can be reduced via programmable parameters (this parameter can affect power, memory, and other measurements) |
| ECG Measurement Duration | Can be changed via programmable parameters |
| ECG Sampling Rate | This parameter may not be programmable and a change can require reconfiguration of AFE registers |

A quality metric of the ECG data can be calculated and used to filter which ECG data can be used for a heart rate metric which can improve the accuracy of a heart rate metric calculated from noisy ECG data. In extensively corrupt ECG data it may not be possible to accurately identify R-wave peaks and their location in the ECG data which can lead to an inaccurate heart rate metric. Thus, the extensively corrupt ECG data can be ignored and/or discarded, rather than outputting and/or displaying an incorrect heart rate to the patient.

The HR algorithm can produce outputs for each frame of ECG data, such as, for example, (i) a heart rate metric in beats per minute and (ii) a flag indicating whether the heart rate metric reported in the corresponding frame is valid (e.g., flag is set to 1 if the measurement is valid and set to 0 otherwise or vice versa). The HR algorithm can also produce other auxiliary metrics which may be used by the wearable device and/or remote device.

FIG. 23 illustrates a flowchart for receiving and process ECG data. Namely, ECG signal is received from electrodes of the wearable device that are placed on a patient. The raw ECG signal can be processed in an analog processing block 2302 and output as raw ECG data. The raw ECG data can be input to a processing block 2304 for processing by the HR algorithm. The HR algorithm can process the ECG data in a vector co-processor 2306 (e.g., a vector math co-processor such as, for example, a dual-core DSP processor) and a processor 2308 (e.g., ARM Cortex™ M3 processor). The vector co-processor 2306 and processor 2308 can be co-located on the wearable device or one can be on the wearable device and one can be on the remote device. The vector co-processor can be a vector math co-processor on an ASIC and the processor can be an advanced reduced instruction set computing machine processor on the ASIC. The processing block 2304 can extract features from the data and output metrics, such as, for example, heat rate and/or other metrics.

In the comparative algorithms, processing of the ECG data was not performed in the vector co-processor 2306 and the RAW ECG data would have been input to the processor 2308. However, the HR algorithm according to the present disclosure processes the ECG data in the vector co-processor 2306. Namely, the vector co-processor 2306 enhances the raw ECG data received from the analog processing block 2302 and outputs enhanced ECG data to the processor 2308 where features can be extracted from the enhanced ECG data. That is, the processing of the raw ECG data can be split across the vector co-processor 2306 and the processor 2308. Namely, the vector co-processor 2306 can de-noise the raw ECG data by converting the raw ECG data into an enhanced ECG data with accentuated R-wave peaks that can be more facile to identify and/or locate while calculating a heart rate metric. For example, the enhanced ECG data can require less processing by the processor 2308 and/or a different processor to identify and locate R-wave peaks.

The vector co-processor 2306 can reduce the sampling rate of the ECG data if desired or output the enhance ECG data at the same sampling rate as the raw ECG data.

For example, the vector co-processor 2306 can receive raw ECG data sampled at a first frequency (e.g., 256 Hz) and produce enhanced ECG data at the same first frequency (e.g., 256 Hz) or at a different second frequency less than the first frequency (e.g., 64 Hz). By utilizing the vector co-processor 2306 to create the enhance ECG data, efficiency can be increased in downstream filtering operations, the quantity of data moved can be less, and the efficiency of memory utilization in the processor 2308 can be increased. Utilizing the vector co-processor 2306 and processor 2308 can enable more flexibility in hardware design of the wearable device and modification of the vector co-processor 2306 or processor 2308 with minimal, if any affect, to the one not being modified.

Various programmable parameters for use with the HR algorithm according to the present disclosure are provided in Table 20.

TABLE 20

Programmable Parameters

| Parameter | Description |
| --- | --- |
| ECG Event Interval | Interval at which the ECG measurement is scheduled |
| ECG Event Duration | Duration of the ECG measurement. |
| ECG Recording Mode | Controls which records are produced by the heart rate algorithms (e.g., 0: Disable ECG, 1: Measurement only) |
| ECG Quality Threshold | The number of processing sub-frames which must be valid for a frame to be valid. In examples where an ECG frame is split into 4 sub-frames for processing, this threshold can take values from {0, 1, 2, 3, 4} |
| ECG Peak Spread Threshold | The maximum allowable spread in the number of R-wave peaks discovered across sub-frames for a frame to be valid |
| ECG MAD Threshold | The maximum allowable median absolute deviation (MAD) for the R-R interval vector for a frame to be valid (0: disable) |
| ECG HRV Interval | Interval at which the HRV mode measurement is scheduled |
| ECG HRV Block | Number of frames in an HRV measurement |
| ECG HRV Gap | Time duration between frames comprising an HRV measurement |
| ECG Act Threshold | Threshold for total activity (computed from the synchronous accelerometer data frame) above which a frame is declared invalid (0: disable). For example, total activity can be the standard deviation of the net acceleration vector computed over an accelerometer data frame |

Once ECG signal acquisition starts (e.g., controlled by the programmable parameter of ECG Event Interval), the vector co-processor 2306 can operate on frames of ECG data (e.g., 512 samples at 256 Hz), while maintaining the states of the filtering operations across processing frame boundaries until the ECG signal acquisition is complete (e.g., controlled by the programmable parameter of ECG Event Duration). The states of the filter operations can be reset at the start of every acquisition of an ECG signal. For example, the vector co-processor 2306 can receive raw ECG data and enhance the ECG data through a series of linear and/or non-linear filtering operations, such as, for example, the sequence of filtering operations as depicted in FIG. 24 and described herein.

As illustrated in FIG. 24, to enhance the raw ECG data, the raw ECG data can be processed through a high pass filter by the vector co-processor, 2402. The high pass filter can suppress low frequency sources of noise, such as, for example, baseline wander and motion artifacts. The high pass filter can be implemented as FIR filter (e.g., 31-tap) with a magnitude response as illustrated in FIG. 25 and the parameters enumerated in Table 21.

TABLE 21

Design Parameters for a High Pass Filter

| Design parameter | Value |
| --- | --- |
| Impulse response | FIR |
| Order | 30 |
| Sampling rate (Hz) | 256 |
| Passband frequency (Hz) | 13 |
| Stopband frequency (Hz) | 3 |
| Stopband attenuation (dB) | 40 |
| Design method | Equi-ripple |

Referring back to FIG. 24, the high pass filtered ECG data can be processed through a low pass filter to suppress high frequency sources of noise, such as, for example, 60 Hz power line interference, 2404. The low pass filter can be implemented as a FIR filter (e.g., 31-Tap) with magnitude response as illustrated in FIG. 26 and the parameters enumerated in Table 22.

TABLE 22

Design Parameters for a Low Pass Filter

| Design parameter | Value |
| --- | --- |
| Impulse response | FIR |
| Order | 30 |
| Sampling rate (Hz) | 256 |
| Passband frequency (Hz) | 16 |
| Stopband frequency (Hz) | 30 |
| Stopband attenuation (dB) | 40 |
| Design method | Equi-ripple |

Referring back to FIG. 24, the low pass filtered ECG data can be processed through a down-sampling filter, 2306. The down-sampling filter can reduce the sampling rate of the ECG data which can reduce processing cycles required to process the ECG data and the size of the ECG data in memory. For example, the down-sampling filter can remove 1 out of 2 samples, 2 out of 3 sample, 3 out of 4 samples, or another amount of samples can be removed. In various examples, the low pass filtered ECG data is not processed through a down-sampling filter.

The ECG data can be processed through a derivative filter to further enhance the R-wave peaks and sharpen (i.e., increase the slope) of features in the R-wave peaks of the ECG data, 2408. The derivative filter can process the ECG data using a FIR filter (e.g., 5-tap). The coefficients of the derivative filter can be set to a scaled version of [0.5, 0, 0, 0, −0.5]. The derivative filter can be implemented with a magnitude response as illustrated in FIG. 27. The stopband frequencies of the preceding high-pass filter and low-pass filter are illustrated by dashed lines in FIG. 27 for reference.

Referring back to FIG. 24 yet again, the derivatized ECG data can be processed through a rectification filter (i.e., absolute value of the ECG data) to make the polarity of the R-wave peaks deterministic (i.e., always positive), 2410.

The rectification filter can eliminate ambiguity associated with the polarity of the ECG data. The rectification filter can prepare the ECG data for the subsequent step of boxcar averaging. In various examples, the rectification filter can be the only non-linear filtering operation executed by the vector co-processor.

The rectified ECG data can be processed through a boxcar filter, 2412. For example, the rectified ECG data can be averaged using a 24-tap boxcar filter with all coefficients set to a scaled version of 1/24. The boxcar filter can boost, localize, and/or isolate QRS complexes and further enhance R-wave peaks. The data output from the boxcar filter can be the enhanced ECG data which can be passed on to the processor. The boxcar filter can be implemented with a magnitude response as illustrated in FIG. 28.

In this way, processing of the ECG signal in the vector co-processor prior to the processor can lower the processing cycles required in the processor, the clock speed of the processor, and/or the memory utilization in the processor. Additionally, the enhancement of the ECG data can comprise a computational engine optimized for implementing high efficiency signal processing tasks. These signal processing functions can be hard coded in logic which can be 10 times or more efficient compared to software-based algorithms implemented in software running on processor 111 or other microcontroller unit. The efficiency can be a decrease in chip size, a decrease in power consumption, and/or a decrease in clock speed. Additionally, the heart rate algorithm can maintain some level of programmability, but can utilize execution units that are optimized calculations. The HR algorithm can enable the wearable device to be indiscriminately placed on a patient and still obtain an accurate heart rate metric. For example, depending on the location of the wearable device on the body of the patient, the ECG signal detected by the wearable device can have a similar overall structure but the amplitudes of the ECG signals can vary between locations. The variance in the amplitude of the ECG signal can be accounted for by adjustment of various thresholds in the HR algorithm.

Referring to FIGS. 29A-G, an example of raw ECG data as processed by the vector co-processor including down-sampling is provided. FIGS. 29A-G visually depict a frame of ECG data (1 frame=14 sec) collected from a patient while resting, wearing a wearable device on the torso. FIG. 29A illustrates the raw ECG data and FIG. 29B illustrates a high pass filtered ECG data after processing the raw ECG data from FIG. 29A through a high pass filter. FIG. 29C illustrates a low pass filtered ECG data after processing the high pass filtered ECG data from FIG. 29B through a low pass filter. FIG. 29D illustrates a down-sampled ECG data after processing the low pass filtered data from FIG. 29C through a down-sampling filter. FIG. 29E illustrates a derivatized ECG data after processing the down-sampled ECG data from FIG. 29D through a derivative filter. FIG. 29F illustrates a rectified ECG data after processing the differentiated ECG data from FIG. 29E through a rectification filter. FIG. 29G illustrates an enhanced ECG data after processing the rectified ECG data from FIG. 29F through a box car filter.

Referring to FIGS. 30A-F, an example of raw ECG data as processed by the vector co-processor without down-sampling is provided. FIGS. 30A-G visually depict a frame of ECG data (1 frame=14 sec) collected from a patient while resting, wearing a wearable device on the torso. FIG. 30A illustrates the raw ECG data and FIG. 30B illustrates a high pass filtered ECG data after processing the raw ECG data from FIG. 30A through a high pass filter. FIG. 30C illustrates a low pass filtered ECG data after processing the high pass filtered ECG data from FIG. 30B through a low pass filter. FIG. 30D illustrates a derivatized ECG data after processing the low pass filtered ECG data from FIG. 30C through a derivative filter. FIG. 30E illustrates a rectified ECG data after processing the differentiated ECG data from FIG. 30D through a rectification filter. FIG. 30F illustrates an enhanced ECG data after processing the rectified ECG data from FIG. 30E through a box car filter.

The enhanced ECG data output of the vector co-processor can be output in 24-bit resolution. Due to memory constraints in some processors, each frame of ECG data of ECG data can be normalized to fit in 16-bit resolution and the resultant shift factor (e.g., NR_shifts) can be stored and used in downstream processing. The shift factor can be computed based on the maximum value (Max) observed in the frame, which may also computed by the vector co-processor.

Referring to FIG. 31, an example of normalization of the ECG data is provided. In various examples, the vector co-processor can process data as a first number of bits (e.g., 24 bit numbers) and the processor can process data as a second number of bits less than the first number of bits (e.g., 16 bit numbers) to save memory. In order to normalize the data from the vector co-processor to the processor, the number of bit shifts required to align (e.g., shift factor) to the least significant bit (e.g., bit 23) is determined in the enhanced ECG data. As illustrated the shift factor of a frame of ECG data is computed to be 5 in order to normalize the maximum value observed in the frame of ECG data. The instruction to compute the shift factor can be "(INT32 EcgFileRead::Normp24(UINT32 inp32)". Thereafter, a shift (e.g., shift left) is performed based on the shift factor and saved into memory. A number of least significant bits (e.g., 16 as illustrated in FIG. 31) are kept and passed to the processor. Normalization can be a method to stich together various sub-frames of ECG data and account for shifts in amplitude between sub-frames.

Referring back to FIG. 23, the enhanced ECG data from the vector co-processor 2306 can be input into the processor 2308. The processor 2308 can identify and locate the R-wave peaks in the enhanced ECG data and translate the locations of the R-wave peaks into a heart rate metric. The processor 2308 can also calculate quality metrics which can be used to determine the validity of the output heart rate metric. Determining the validity of the output heart rate metric can limit, if not prevent, the wearable device from outputting an inaccurate heart rate due to the input raw ECG data being extensively corrupt. The validity determination can be used downstream by the wearable device and/or a remote device to filter out and discard inaccurate output heart rate metrics.

The processor 2308 can wait until an amount of enhanced ECG data spanning a duration is buffered as determined by a programmable parameter (e.g., ECG Event Duration) before beginning to process the enhanced ECG data from the vector co-processor 2306. For example, at a ECG sampling rate of 256 Hz and a nominal ECG event duration of 14 sec, 3584 samples of the enhanced ECG data should be buffered by the processor 2308 prior to processing the enhanced ECG data. The buffer for the enhanced ECG data can partitioned into sub-frames with partial overlap. For example, as illustrated in FIG. 32, the buffer can be partitioned into four sub-frames with partial overlap. The four sub-frames can be 3.5 seconds each of enhanced ECG data. The sub-frames can be overlapped in order to avoid missing peaks due to processing of boundary effects. The last sub-frame in a frame may not have any overlap. An overlap factor of, such as, for example, 0.125 can be used.

FIG. 33 illustrates a flowchart for processing enhanced ECG data in the processor. Namely, the processor can utilize a peak finder (PF) algorithm and an adaptive thresholding (AT) algorithm to find peaks in the sub-frames partitioned in the buffer, 3302. Peak finding can be based on finding pairs of rising and falling edges, given a level crossing of a peak threshold. The peak threshold can be defined according to the AT algorithm described herein. The processor can utilize a peak finding (PF) algorithm as illustrated in FIG. 34. The PF algorithm and AT algorithm can be sub-components of the HR algorithm.

A rising edge can be declared when a number of consecutive samples are found to be above the peak detection threshold and the local derivative is positive. A falling edge can be declared when a number of consecutive samples are found to be below the peak detection threshold. A tentative peak can be declared when a falling edge is found following a rising edge (e.g., a falling edge and rising edge pair). The PF algorithm may only looks for level crossings and not for local maxima, thus peak refinement may be required as described herein.

Referring to FIG. 35A, a rising edge 3502 is declared after 3 consecutive samples are found after threshold 3506. A falling edge 3504 is declared after 3 consecutive samples are found after threshold 3506 and a peak is declared based on a falling edge 3504 and a rising edge pair 3502.

The processor can also utilize an AT algorithm in conjunction with the PF algorithm in order identify peaks in each sub-frame. The AT algorithm can comprise dynamically adapting (e.g., changing, adjusting) peak thresholds (e.g., a lower peak threshold L, an upper peak threshold U) until they converge (i.e., result in a substantially identical number or an identical number of identified R-wave peaks) or fail to converge due to one or more exit criteria being met. The AT algorithm can be initialized with data dependent thresholds to account for signal amplitude variations across sub-frames.

For each sub-frame, the AT algorithm can compute equation 17.

$$M=\min\{m, \mu+3\sigma\} \quad \text{Equation 17}$$

where m is the maximum value of the ECG data;
 $\mu$ is the mean of the ECG data; and
 $\sigma$ is the standard deviation of the ECG data.

A first quantity of samples (referred to as the transient region) in the first sub-frame can be omitted to allow for the filter operations in the vector co-processor to converge since the filter operations may need to initialize at the beginning of acquisition an ECG signal. In various examples, the first quantity of samples is 60. The duration of the transient region can be chosen based on the aggregate step response of all the filter operations in the vector co-processor. Thereafter, the AT algorithm can initialized the peak thresholds. For example, the initial peak thresholds can be based on a statistic of the ECG data, such as, for example, a maximum, a mean, and/or a standard deviation. The PF algorithm can calculate the number of peaks based on threshold U (nU) and the number of peaks based on threshold L (nL) while the conditions in Equation 18 are met.

$$nU \neq nL \quad \text{Equation 18}$$

where number of iterations≤max number of iterations

The thresholds can be refined according to Equation 19 and the PF algorithm can re-calculate nU and nL as long as the conditions in Equation 18 are still met.

$$\Delta = U - L;$$

$$U = U - \Delta/4;$$

$$L = L + \Delta/4 \quad \text{Equation 19}$$

The AT algorithm can declare a sub-frame as valid if the iterations converge (i.e., nU=nL when the while loop terminates) and declare the sub-frame as invalid otherwise (e.g., number of iterations>max number of iterations).

Figure 36A:
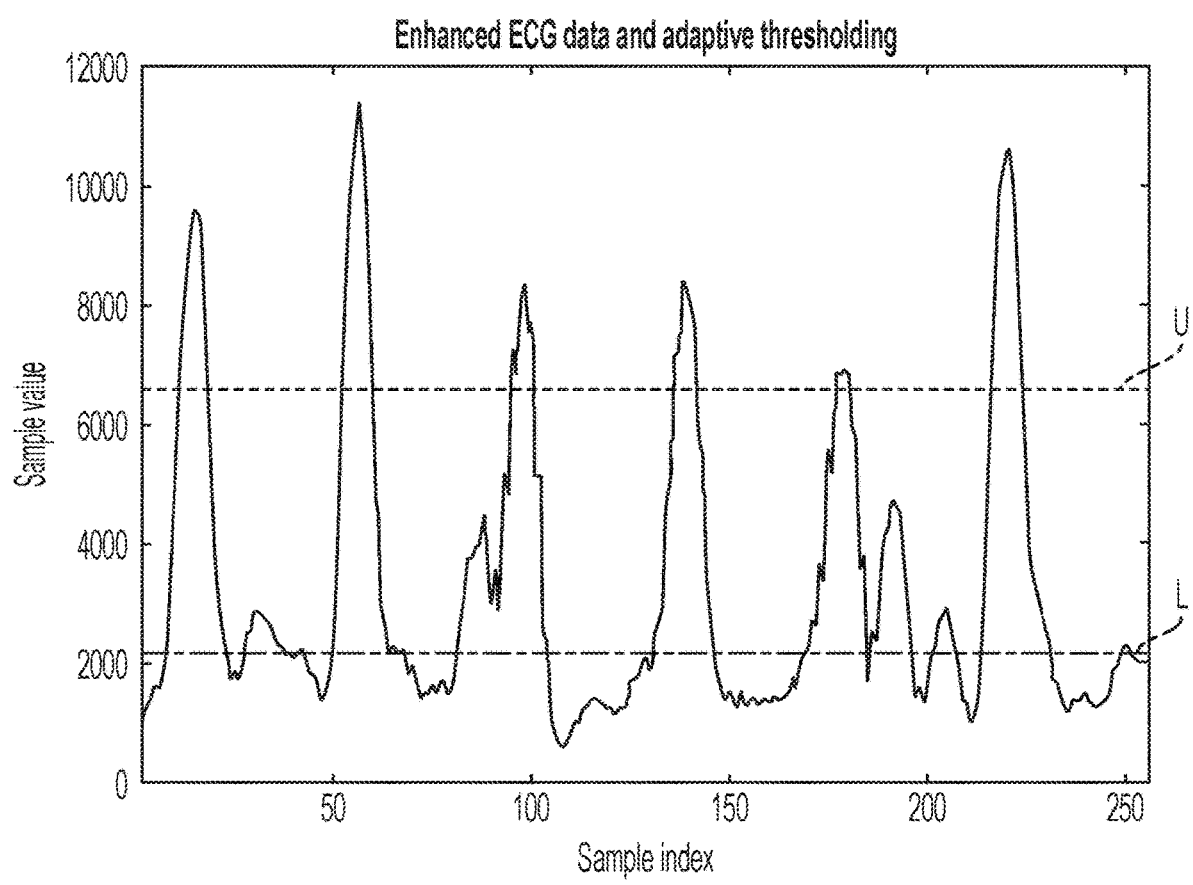
Figure 36B:
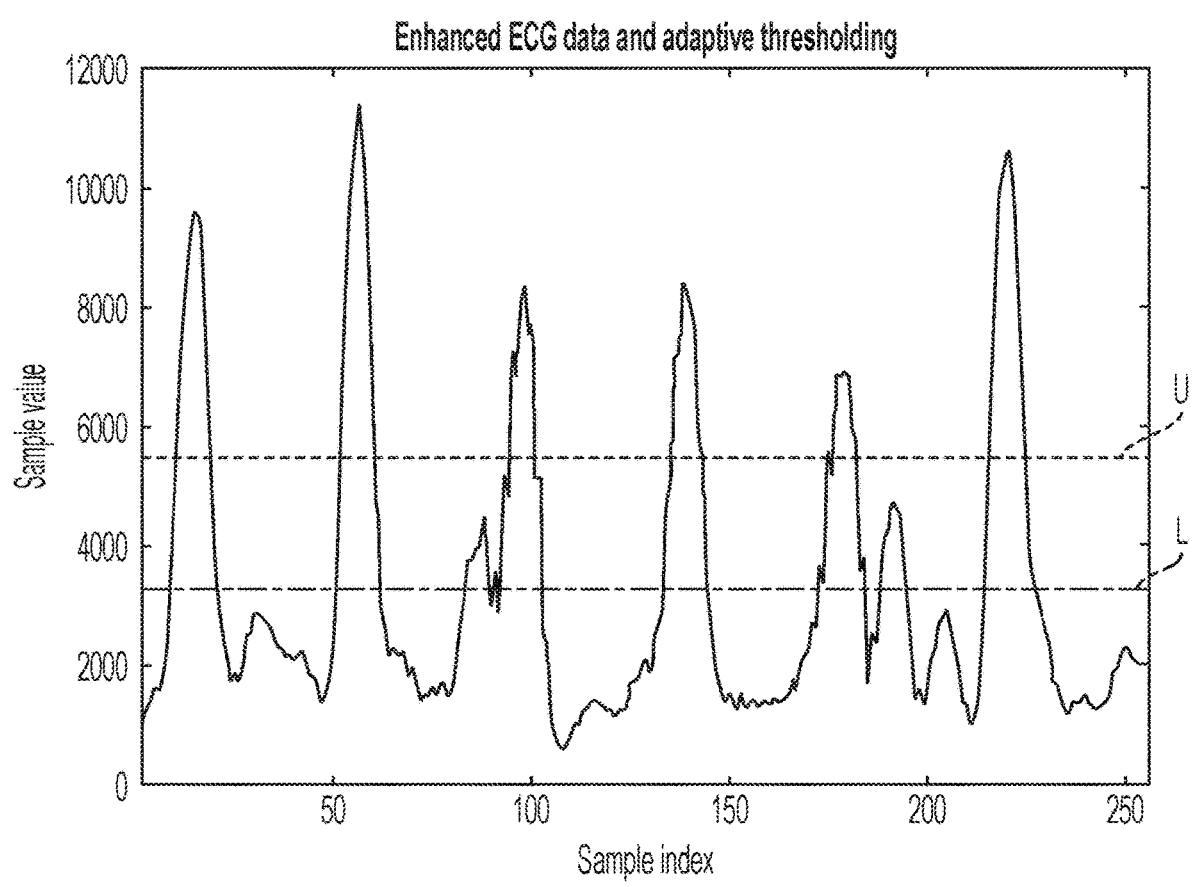
Figure 36C:
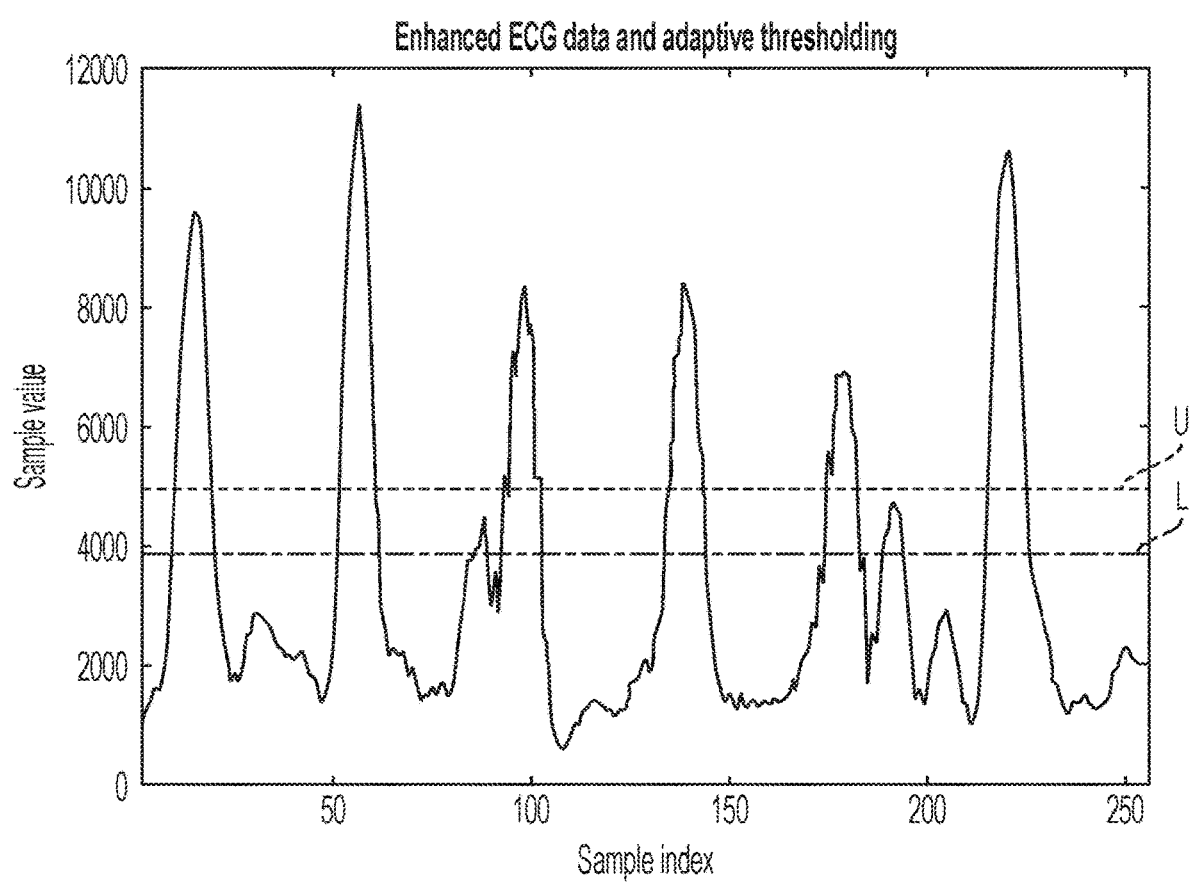
Figure 36D:
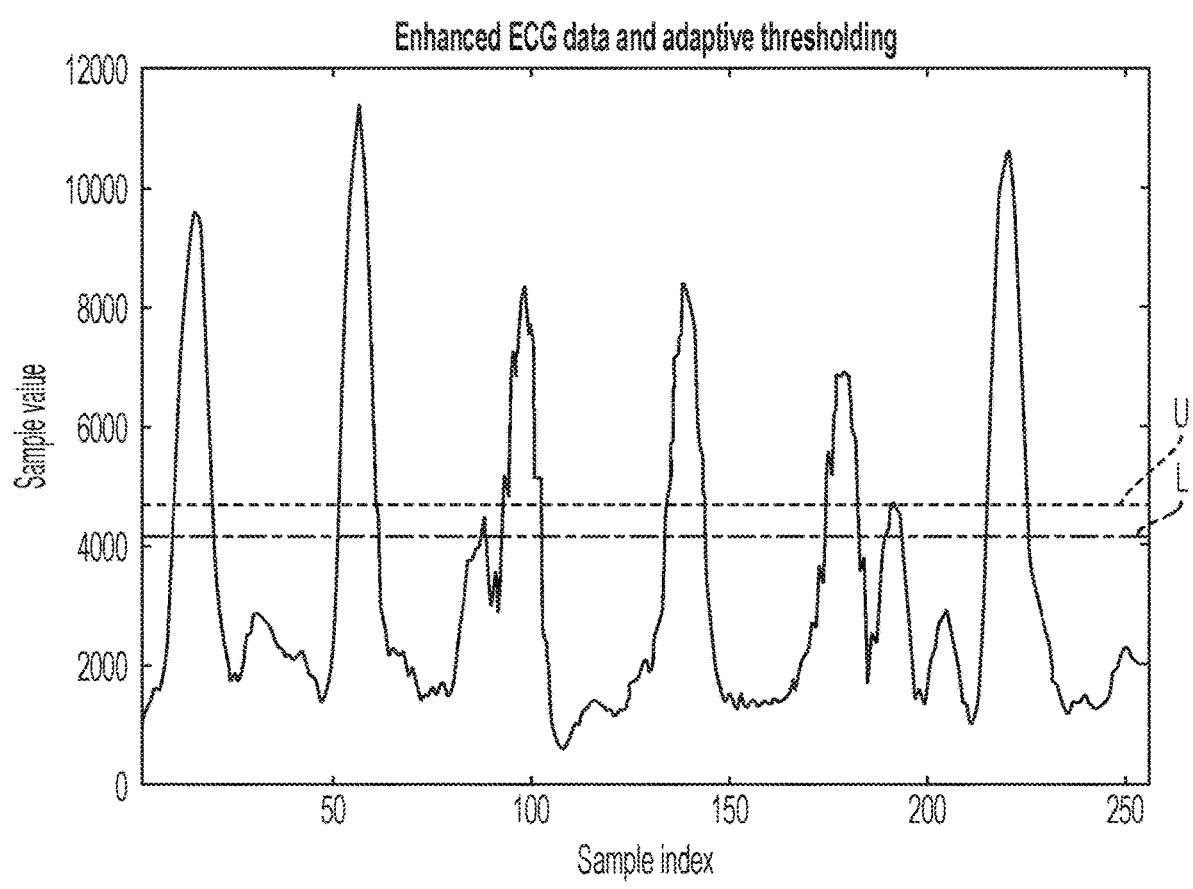
Figure 36E:
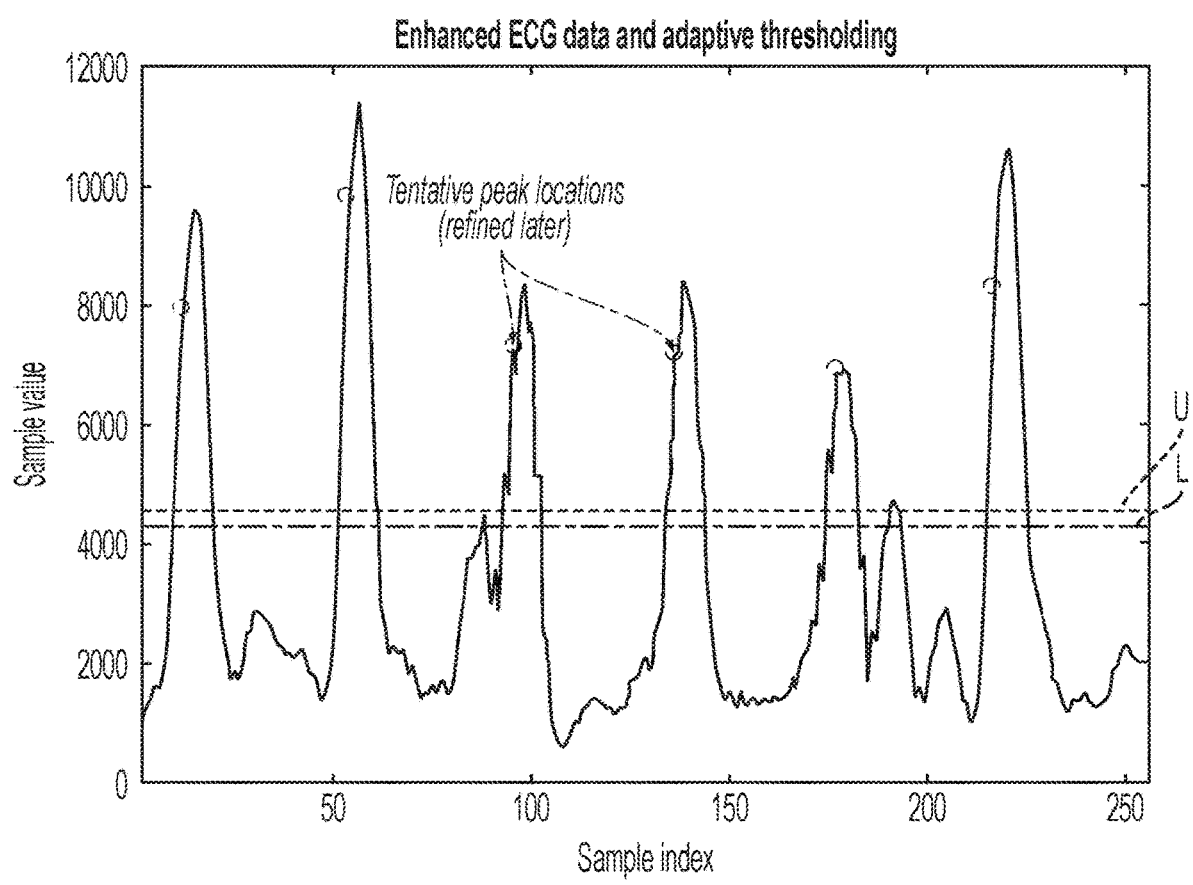

Referring to FIGS. 36A-E, an example of dynamically adapting thresholds in ECG data utilizing an adaptive thresholding algorithm. The thresholding algorithm can be a sub-component of the HR algorithm. In FIG. 36A, threshold L is initialized as 20% of the maximum value in the ECG data and threshold U is initialized as 60% of the maximum value. The max number of iterations is defined as 10. Thereafter, a first iteration of the number of peaks is calculated based on each initial peak threshold, U and L. Namely, based on threshold U there are 6 peaks and based on threshold L there are 8 peaks in FIG. 36A. The AT algorithm evaluates Equation 18 and determines the conditions are met and continues dynamically adapting the peak thresholds, U and L.

The thresholds, U and L, are dynamically adapted by the AT algorithm based on Equation 19. Thereafter, a second iteration of the number of peaks, nU and nL, is calculated based on each adapted peak threshold, U and L. Namely, based on threshold U there are 6 peaks and based on threshold L there are 8 peaks in FIG. 36B. The AT algorithm evaluates Equation 18 and determines the conditions are met and continues dynamically adapting the peak thresholds, U and L.

The peak thresholds, U and L, are dynamically adapted based on Equation 19 for the second time. Thereafter, a third iteration of the number of peaks, nU and nL, is calculated based on each twice adapted peak threshold, U and L. Namely, based on threshold U there are 6 peaks and based on threshold L there are 7 peaks in FIG. 36C. The AT algorithm evaluates Equation 18 and determines the conditions are met and continues dynamically adapting the peak thresholds, U and L.

The peak thresholds, U and L, are dynamically adapted based on Equation 19 for the third time. Thereafter, a fourth iteration of the number of peaks, nU and nL, is calculated based on each thrice adapted peak threshold, U and L. Namely, based on threshold U there are 6 peaks and based on threshold L there are 7 peaks in FIG. 36D. The AT algorithm evaluates Equation 18 and determines the conditions are met and continues dynamically adapting the peaks thresholds, U and L.

The peak thresholds, U and L, are dynamically adapted based on Equation 19 for the fourth time. Thereafter, a fifth iteration of the number of peaks, nU and nL, is calculated based on each four time adapted peak threshold, U and L. Namely, based on threshold U there are 6 peaks and based on threshold L there are 6 peaks in FIG. 36E. The AT algorithm evaluations Equation 18 and determines the conditions are no longer met since the number of peaks (nU) based on U equals the number of peaks (nL) based on L. Thus, the AT algorithm ceases the dynamically adapting the peak thresholds, U and L, and the PF algorithm defines tentative peaks based on the adapted peak thresholds. Additionally, since the number of iterations is less than the max number of iterations, the sub-frame is declared as valid.

Referring back to FIG. 33, the tentative peaks found from the PF algorithm can be aggregated, 3304. For example, peaks found in all sub-frames can be collated and peaks found in the transient region of the first sub-frame can be discarded. In various examples, peak aggregation may not occur. The peaks found by the PF algorithm may include additional peaks (e.g., T-wave peaks) rather than just R-wave peaks. Thus, the tentative peaks should be validated and/or adjusted to ensure that the found peaks correspond to R-wave peaks.

The tentative peaks identified by the PF algorithm can be refined based on a local maximum search, 3306. For example, a peak search window can be defined based on the rising edge based on the peak thresholds and the local maximum in the search window can be declared as the location of the peak. The peak search window can span a number of samples (e.g., 40) starting at the location of the rising edge and looking forward (e.g., towards the paired falling edge). The number of samples can be defined to accommodate substantially all of the QRS complex durations of interest (e.g., up to 120 ms). The PF algorithm may not declare a location of a peak which occurs after an actual nearby peak which can prevent the need for a backward search.

As illustrated in FIG. 35B, a search window 3510 can be defined based on rising edge 3502. Thereafter, a location of a refined peak 3508 can be declared based on a maximum search in the peak search window 3510.

Referring back to FIG. 33, once the locations of the peaks have been declared and the locations have been refined to correspond to local maximum, the processor can eliminate spurious peaks, 3308. For example, peaks which are closer than a distance threshold to each other (e.g., as dictated by the cardiac refractory period which may to be no smaller than 170 ms) can be eliminated. For example, the locations of the peaks are scanned sequentially and if successive peaks are found to be within 44 samples of each other, the peak with the higher amplitude can be retained and the other peak or peaks can be eliminated. Additionally, the peaks in the transient region can be eliminated.

The processor can eliminate peaks based on amplitude variation rejection, 3310. For example, in cases of high amplitude T-wave peaks, the PF algorithm may occasionally identify a T-wave peaks as a tentative peak which can occur as a bimodal amplitude distribution in the enhanced ECG data. In order to avoid declaring the T-wave peak from the tentative peaks as a valid R-wave peak, a bimodal amplitude detector can be activated by the processor. If a bimodal amplitude distribution is detected, the peak distribution can be analyzed and only peaks corresponding to R-waves may be considered for the Heart Rate metrics.

In order to determine if bimodal amplitude is present in the enhanced ECG data, the bimodal amplitude detector can adjust the amplitudes of the tentative peaks for a shift factor, compute a minimum peak amplitude, $A_{min}$, and compute a maximum peak amplitude, $A_{max}$. The peak amplitudes can be binned into $N_b$ bins and the bin ranges can be determined to dynamically to cover the ranges of the peak amplitudes (e.g., 0.8 minimum amplitude ($A_{min}$) 1.2 maximum amplitude ($A_{max}$)). The bimodal amplitude detector can determine the bin with the most entries, $n_1$, and the bin with the second most entries, $n_2$. The amplitude, $A_1$, of the bin, $n_1$, and the amplitude, $A_2$, of the bin, $n_2$, can be computed. Then the processor can determine if the conditions (i)-(v) in Equation 20 are valid.

(i) $r_1 > thresh_1$ (ii) $r_2 > thresh_2$ (iii) $[B(n_1)+B(n_2)]/K > thresh_3$ (iv) $|n_1 - n_2| > 2$ (v) $K > thresh_4$  Equation 20 where K is the total number of peaks $r_1 = B(n_2)/B(n_1)$

B(n) is the number of elements in bin n $r_2 = \max(A_2/A_1, A_1/A_2)$

If all of the conditions (i)-(v) in Equation 20 are valid, then the bimodal amplitude detector can declare that the enhanced ECG data comprises a bimodal amplitude distribution. Responsive to the declaration of bimodal amplitude distribution, the processor can retain peaks which correspond to valid R-waves and remove the peaks which correspond to T-waves from the tentative peaks. For example, if $A_1$ is greater than $A_2$, the processor can retain peaks in the enhanced ECG data that have an amplitude in a first range corresponding to the bin with the most entries, $n_1$ (e.g., 0.8 $A_1$ to 1.2 $A_1$). However, if $A_2$ is greater than $A_1$, the processor can retain peaks in the enhanced ECG data that have an amplitude in a second range corresponding to the bin with the second most entries, $n_2$ (e.g., 0.8 $A_2$ to 1.2 $A_2$). The determination of condition (v) can ensure that there are enough peaks available for binning to construct a reliable histogram. In various examples, $N_b=10$, $thresh_1=0.25$, $thresh_2=1.3$, $thresh_3=0.8$, $thresh_4=15$.

Additionally, the bimodal amplitude detector can determine if the at least one of the following conditions is met: a number of entries in bin $n_2$ is greater than or equal to a bin threshold; the difference between $A_1$ and $A_2$ is greater than or equal to a difference threshold; the number of entries in bins $n_1$ and $n_2$ is greater than a threshold portion of the total number of peaks; and $n_1$ and $n_2$ are not adjacent bins. In various examples, the bimodal amplitude detector can determine if all the conditions are met.

Referring to FIG. 37, tentative peaks have been declared at the locations marked by a circle in the ECG data 3702. The tentative peaks comprise both R-wave peaks and T-wave peaks. Thereafter, the amplitudes of the tentative peaks in FIG. 37 were binned into 10 bins and the bin ranges cover the ranges of the peak amplitudes. The amplitude histogram output of the binned peak amplitudes is illustrated in FIG. 38. Thereafter, the bimodal amplitude detected determined the conditions (i)-(v) in Equation 20 were valid and declared that the enhanced ECG data comprises a bimodal amplitude distribution. Response to the declaration of the bimodal amplitude declaration, peak with amplitudes in a range of 80% to 120% of the peaks in bin 8 are retained and other peaks are removed (e.g., peaks in bin 2 and 3 are removed). The surviving peaks from FIG. 37 that were not removed by the bimodal amplitude detector are marked by a circle in the ECG data 3902 in FIG. 39.

Any peaks not removed by peak aggregation at step 3304, spurious peak elimination at step 3308, and the amplitude variation peak rejection at step 3310 are declared as valid R-wave peaks. The valid R-wave peaks can be used for the Heart Rate metric.

Examples of ECG data were modeled in MATLAB. Each example comprised T-waves and the amplitude of the T-waves was varied between the examples. The heart rate (based on an R-R interval) was kept constant at 80 beats per minute. The examples were processed with a comparative algorithm and a bimodal amplitude detector according to the present disclosure and based on the valid R-wave determination output, a heart rate metric was calculated. Table 23 illustrates the results of a comparative algorithm for determining a heart rate based on the examples of ECG data and Table 24 illustrates the results of a HR algorithm according to the present disclosure with the bimodal amplitude rejection.

TABLE 23

| T-wave amplitude (mV) | # input frames of ECG data | # valid frames of ECG data | Mean/Min/Max HR in valid frames (bpm) | Pass/Fail |
|---|---|---|---|---|
| 0.0 | 18 | 18 | 80/80/80 | P |
| 0.2 | 17 | 17 | 80/80/80 | P |
| 0.4 | 17 | 17 | 80/80/80 | P |
| 0.6 | 17 | 17 | 80/80/80 | P |
| 0.8 | 17 | 17 | 132/132/132 | F |
| 1.0 | 17 | 10 | 136/132/160 | F |
| 1.2 | 17 | 17 | 178/128/213 | F |

TABLE 24

| T-wave height (mV) | # input frames | # valid frames | # frames with bimodal amp detected | Mean/Min/Max HR in valid frames (bpm) | Pass/Fail |
|---|---|---|---|---|---|
| 0.0 | 22 | 22 | 0 | 80/80/80 | P |
| 0.2 | 22 | 22 | 0 | 80/80/80 | P |
| 0.4 | 22 | 22 | 0 | 80/80/80 | P |
| 0.6 | 22 | 22 | 0 | 80/80/80 | P |
| 0.8 | 22 | 22 | 22 | 80/80/80 | P |
| 1.0 | 22 | 21 | 21 | 80/80/80 | P |
| 1.2 | 22 | 22 | 22 | 80/80/80 | P |

As shown, the comparative algorithm did not reliably succeed beyond a T-wave amplitude of 0.6 mV. However, the bimodal amplitude detector according to the present disclosure rejected the T-waves so that an accurate heart rate metric can be calculated at T-wave amplitudes of greater than 0.6 mV.

Additionally, referring to FIG. 30G, is an example of enhanced ECG data from FIG. 30F as processed by the processor. The peak thresholds are illustrated by solid horizontal lines, the boundaries of each frame are illustrated by a dashed vertical line, the R-wave peaks determined to be valid are marked by a circle.

Referring back to FIG. 33, once the tentative peaks are determined to be valid R-wave peaks, a HR algorithm can calculate the R-R interval for the enhanced ECG data, 3312. The R-R interval can be calculated according to Equation 21.

$$RR = \{R_n - R_{n-1}, 2 \leq i \leq N\} \qquad \text{Equation 21}$$

where the R-wave peak locations are defined as $R = \{R_n, 1 \leq i \leq N\}$, while appropriately accounting for discontinuities due to discarded sub-frames.

Based on the R-R vector interval calculation, a HR algorithm can calculate the mean and median heart rate, 3314. The mean heart rate can be determined from the R-R interval according to Equation 22 and the median heart rate can be determined from the R-R interval according to Equation 23.

$$\text{Mean Heart Rate} = 60 * (F_s / \text{mean}(RR)) \text{ beats/min} \qquad \text{Equation 22}$$

where $F_s$ is the sampling rate of the enhanced ECG data.

$$\text{Median Heart Rate} = 60 * (F_s) / \text{median}(RR) \text{ beats/min} \qquad \text{Equation 23}$$

where $F_s$ is the sampling rate of the enhanced ECG data (e.g., 256 Hz).

The enhanced ECG data acquired from discontinuous data by wearable device can be susceptible to noise which may not be suppressed using the signal processing associated with the vector co-processor and the processor. Thus, a quality metric of the enhanced ECG data can be calculated and used to determine if the enhanced ECG data is valid, 3316. The quality metric calculations can be performed in parallel with the heart rate calculations at step 3314. The quality metrics can comprise at least one of peaks spread, a median absolute deviation, and a quality score.

The quality metric can be used to decide (i) which R-wave peaks, if any, in the frame of ECG data should be used for heart rate calculation and (ii) whether a heart rate metric value should be presented to the patient. Valid R-wave peaks present in a valid frame of enhanced ECG data can be used in the heart rate calculation and the heart rate metric value can be presented to the user based on a valid frame. While invalid frames of the enhanced ECG data may not be used in the heart rate calculation and the heart rate value calculated from an invalid frame may not be presented to the user. The quality metrics can be used to determine if a frame of the enhanced ECG data is valid based on a comparison of the quality metric to a quality threshold as described herein. The HR algorithm can ignore a frame or frames of physiological data based on the comparison. In this way, the HR algorithm can accurately determine a physiological metric, such as, a heart rate, from discontinuous data and lower power consumption by not processing invalid frames during calculation of the physiological metric.

The number of peaks spread (PS) can be calculated according to Equation 24 given $n_i$ identified peaks in the $i^{th}$ sub-frame.

$$PS = \max_i\{n_i\} - \min_i\{n_i\} \qquad \text{Equation 24}$$

The Median Absolute Deviation (MAD) can be calculated according to Equation 25 given the R-R interval (RR) and the median absolute deviation metric (median(RR)). The MAD can be a measure of variation around the median.

$$MAD = \text{median}(|RR - \text{median}(RR)|) \qquad \text{Equation 25}$$

The Quality Score (QS) can be calculated as the total number of sub-frames which are deemed valid (e.g., a value in a range of 0 to 4 in examples comprising 4 sub-frames). As stated herein, a sub-frame can be deemed invalid due to (i) non-convergence of the adaptive thresholding and/or (ii) peak rejection due to a bimodal amplitude determination.

A frame can be considered valid if the following conditions (i)-(iii) (e.g., comparisons of the quality metrics to quality thresholds) in Equation 26 are valid.

(i) $MAD < ECG\ MAD$ thresh (ii) $PS < ECG$ PeaksSpread thresh (iii) $QS > ECG\ QS$ thresh. \qquad Equation 26

ECG MAD threshold, ECG Peak Spread threshold and ECG Quality threshold are illustrated in Table 19. In various examples, the MAD quality filter can be disabled by setting the programmable parameter ECG MAD threshold to 0.

As illustrated in FIG. 40, 5 frames of raw ECG data, 3802-3810 are provided and were processed by the vector co-processor and the processor. Namely, each frame of raw ECG data, 3802-3810, was processed through the vector co-processor to enhance the ECG data and the enhanced ECG data was processed in the processor to calculate the median heart rate metric and quality metrics. The ECG MAD threshold was set to 12, the ECG Peak Spread threshold was set to 4, and the ECG Quality threshold was set to 3. The validity of each frame was determined according to Equation 26. The median heart rate metric and quality metrics are shown in Table 25.

TABLE 25

Median Heart Rate Metric and Quality Metrics of Various ECG Data

| Frame of ECG data in FIG. 40 | Median HR | PS | MAD | QS | Validity |
|---|---|---|---|---|---|
| 3802 | 63 | 1 | 2 | 4 | Valid |
| 3804 | 61 | 1 | 2 | 4 | Valid |
| 3806 | 89 | 1 | 19 | 4 | Invalid |
| 3808 | 54 | 0 | 4 | 4 | Valid |
| 3810 | 56 | 1 | 2 | 4 | Valid |

As illustrated, raw ECG data 3806 is invalid and may not be used in a heart rate metric calculation and a heart rate metric value based on raw ECG data 3806 may not be displayed to a patient. Raw ECG data 3802, 3804, 3808, and 3810 are valid and may be used in a heart rate calculation and a heart rate value based on raw ECG data 3802, 3804, 3808, and 3810 may be displayed to a patient.

Additionally, the HR algorithm can utilize features extracted from the raw ECG data and/or enhanced ECG data to determine if the electrodes from the wearable device are in contact with the skin of the patient or not in contact with the skin of the patient. If the HR algorithm determines the electrodes are not attached to the skin of the patient, the HR algorithm can declare the ECG data invalid, otherwise the HR algorithm can declare the ECG data valid. Further example descriptions for how ECG data is used in this case are described in Attorney Docket No. PRTS-220PRV, which is again incorporated herein by reference.

The HR algorithm according to the present disclosure can reduce the number of processing cycles during execution of the HR algorithm and the size (e.g., code space) of the HR algorithm. Therefore, the HR algorithm according to the present disclosure may require less power and memory to execute. For example, the HR algorithm according to the present disclosure can result in an 85% reduction in processing cycles (e.g., from 3.9 million to 0.59 million) during execution of the HR algorithm and a 46% reduction in code space (e.g., from 4.78 kB to 2.6 kB). The reduction in processing cycles and/or memory usage can enable additional features/algorithms to operate in a memory constrained environment. The additional features and/or algorithms can be an HRV measurement, a respiration measurement, and/or IEM dual decode operations. The reduction in processing cycles can reduce power required to process the HR algorithm and can enable faster processing of the HR algorithm. In various examples, the reduction in processing cycles can enable operation of a processor at a lower clock speed which can further reduce power required to process the HR algorithm.

An emulation of the processor employed in firmware of the wearble device was compared to a MATLAB model of the processor that both analyzed enhanced ECG data from a MATLAB model of the vector co-processor. The MATLAB model and emulation resulted in substantially identical heart rate calculations.

An emulation of the vector co-processor and processor employed in firmware of the wearable device that received ECG data in a binary format was compared to a MATLAB model of the vector co-processor and processor that analyzed raw ECG data. The MATLAB model of the processor and the emulation resulted in substantially identical heart rate metric values.

The HR algorithm was evaluated on ECG data in the MIT-BIH arrhythmia database (available at "http://www-.physionet.org/physiobank/database/mitdb/") utilizing a comparative algorithm and the HR algorithm according to the present disclosure. There were 48 ECG data recordings of 30 minutes each (47 patients) in a clinical setting present in the MIT-BIH arrhythmia database. The MIT-BIH arrhythmia database is commonly used for evaluating QRS detection algorithms. Separate noise traces are available for evaluating performance under noisy conditions.

The raw ECG data from the MIT-BIH arrhythmia database was processed with WaveForm Database (WFDB) tools (available at "http://physionet.org/physiotools/matlab/wfdb-app-matlab/"). The WFDB tool processed ECG data is input into a MATLAB model of the HR algorithm according to the present disclosure and evaluated for sensitivity and positive predictability based on annotated results of the ECG data processed only with WFDB tools. Sensitivity was evaluated according to Equation 27 based on the number of true positives (TP) and number of false negatives (FN).

$$\text{Sensitivity} = TP/(TP+FN) \qquad \text{Equation 27}$$

Positive predictability was evaluated according to equation 28 based on the number of true positives (TP) and the number of false positives (FP).

$$\text{Positive predictability} = TP/(TP+FP) \qquad \text{Equation 28}$$

The results of the evaluation of records in the MIT-BIH arrhythmia database with no noise and the quality metrics turned off in the HR algorithm are illustrated in FIGS. 41 and 42. Namely, the results of the sensitivity of the comparative algorithm and the HR algorithm according to the present disclosure are illustrated in FIG. 41. The overall sensitivity mean averaged over all 48 records in the MIT-BIH arrhythmia database for the comparative algorithm was 93.6% and for the HR algorithm according to the present disclosure it was 97.9%. Sensitivity for the HR algorithm can be limited to 98% due to processing of the ECG data in frames.

The results of the positive predictability of the comparative algorithm and the HR algorithm according to the present disclosure are illustrated in FIG. 42. The overall positive predictability mean averaged over all 48 records in the MIT-BIH arrhythmia database for the comparative algorithm was 90.1% and for the HR algorithm according to the present disclosure it was 99.5%.

The results of the sensitivity mean averaged over all 48 records in the MIT-BIH arrhythmia database with added noise and the quality filters turned on in the HR algorithm are illustrated in FIGS. 43A-C. To add the noise to the 48 records, noise traces were added separately with different scaling to vary signal-to-noise ration (SNR) as described at "http://www.physionet.org/physiobank/database/nstdb/".

FIG. 43A illustrates valid frames that were detected with added noise based on electrode motion, FIG. 43B illustrates valid frames that were detected with added noise based on baseline wander, and FIG. 43C illustrated valid frames that were detected with added noise based on muscle artifacts.

The HR algorithm can be effective in clinical settings. Namely, performance of the HR algorithm has been validated in the field after implementation with 10 patients who wore wearable device proximal to the torso for 24-48 hours which resulted in an aggregate of 13.7 days of ECG data. The wearable device performed an ECG measurement every 19 seconds and obtained ECG data therefrom.

The patients also wore a comparative heart rate monitor (CHRM) attached to the torso with standard ECG electrodes. R-R intervals were recorded on the CHRM with a 1 millisecond resolution and the ECG data was provided continuously from the CHRM (e.g., not in a discontinuous manner). The data obtained from the CHRM was post-processed offline (in 14 sec blocks) to calculate the median heart rate. The median heart rate metric value from the CHRM data was compared with a median heart rate metric value from the wearable device after timing synchronization (based on cross-correlation) as illustrated in Table 26.

illustrate the step rate metric value output from the step count algorithm on the wearable device.

The wearable device in conjunction with the HR algorithm can be able to determine a heart rate metric value from ECG data with an accuracy of ±10% or ±beats per minute, whichever is greater, in a heart beat range of 30 to 250 beats. The accuracy can be tested on test waveforms from ANSI/AAMI EC13:2002 Cardiac Monitors, heart rate meters, and alarms, Section 5 Test Methods with a QRS duration between 40 ms and 120 ms and a QRS amplitude between 0.2 mV and 2 mV. The wearable device can be configured to meet the line frequency voltage tolerance requirements (Section 4.2.6.2 of ANSI/AAMI EC13:2002) and drift tolerance requirements (Section 4.2.6.3 of ANSI/AAMI EC13:2002). Additionally, during the testing of accuracy, greater than or equal to 95% of the ECG data should be marked as valid.

FIGS. 45A-D show examples of how the heart rate monitoring may perform in additional settings, such as during active periods. The HR algorithm may be accurate under rest/sleep and limited mobility conditions, with lim-

TABLE 26

Comparison of heart rate metric values calculated from the CHRM which receives ECG data continuously and the wearable device which receives ECG data discontinuously

| Patient | Duration (hours) | % data retained | Normalized cross-correlation Full | Absolute error (bpm) Quarters | Median error (bpm) 90th p | Linear fit 95th p | | Slope | Intercept |
|---|---|---|---|---|---|---|---|---|---|
| 1 | 41.1 | 50% | 0.683 | 0.96/0.68/0.59/0.47 | 1.9 | 2.7 | 0.67 | 0.93 | 4.84 |
| 2 | 32.5 | 97.6% | 0.987 | 0.98/0.99/0.97/0.97 | 2.4 | 3.2 | 0.66 | 0.99 | 1.4 |
| 3 | 46.6 | 92.1% | 0.977 | 0.92/0.99/0.94/0.98 | 5.4 | 7.3 | 0.99 | 0.99 | 2.31 |
| 4 | 25.5 | 98.9% | 0.986 | 0.99/0.99/0.98/0.95 | 2.4 | 3.3 | 0.69 | 1.04 | −2.08 |
| 5 | 49.4 | 94.6% | 0.959 | 0.91/0.98/0.94/0.99 | 3.4 | 5.2 | 0.91 | 1.00 | 0.95 |
| 6 | 36.3 | 97.1% | 0.979 | 0.97/0.98/0.96/0.97 | 2.6 | 3.5 | 0.76 | 0.98 | 1.87 |
| 7 | 61.6 | 88.7% | 0.971 | 0.97/0.98/0.99/0.88 | 3.5 | 5.1 | 0.96 | 0.98 | 2.75 |
| 8 | 9.4 | 97.8% | 0.983 | 0.98/0.68/0.81/0.99 | 4.3 | 6.3 | 1.3 | 0.99 | 2.32 |
| 9 | 3.9 | 87.3% | 0.868 | 0.96/0.65/0.83/0.68 | 2.6 | 5.8 | −0.5 | 1.02 | −1.90 |
| 10 | 22.1 | 97.4% | 0.972 | 0.99/0.94/0.94/0.97 | 2.4 | 3.3 | 1.0 | 0.95 | 4.06 |
| Weighted average | 32.8 | 88.7% | 0.937 | | 3.2 | 4.5 | 0.84 | | |

As shown, the HR algorithm according to the present disclosure performed well compared to the CHRM ECG data even though the HR algorithm utilized discontinuous data.

Figure 44A:
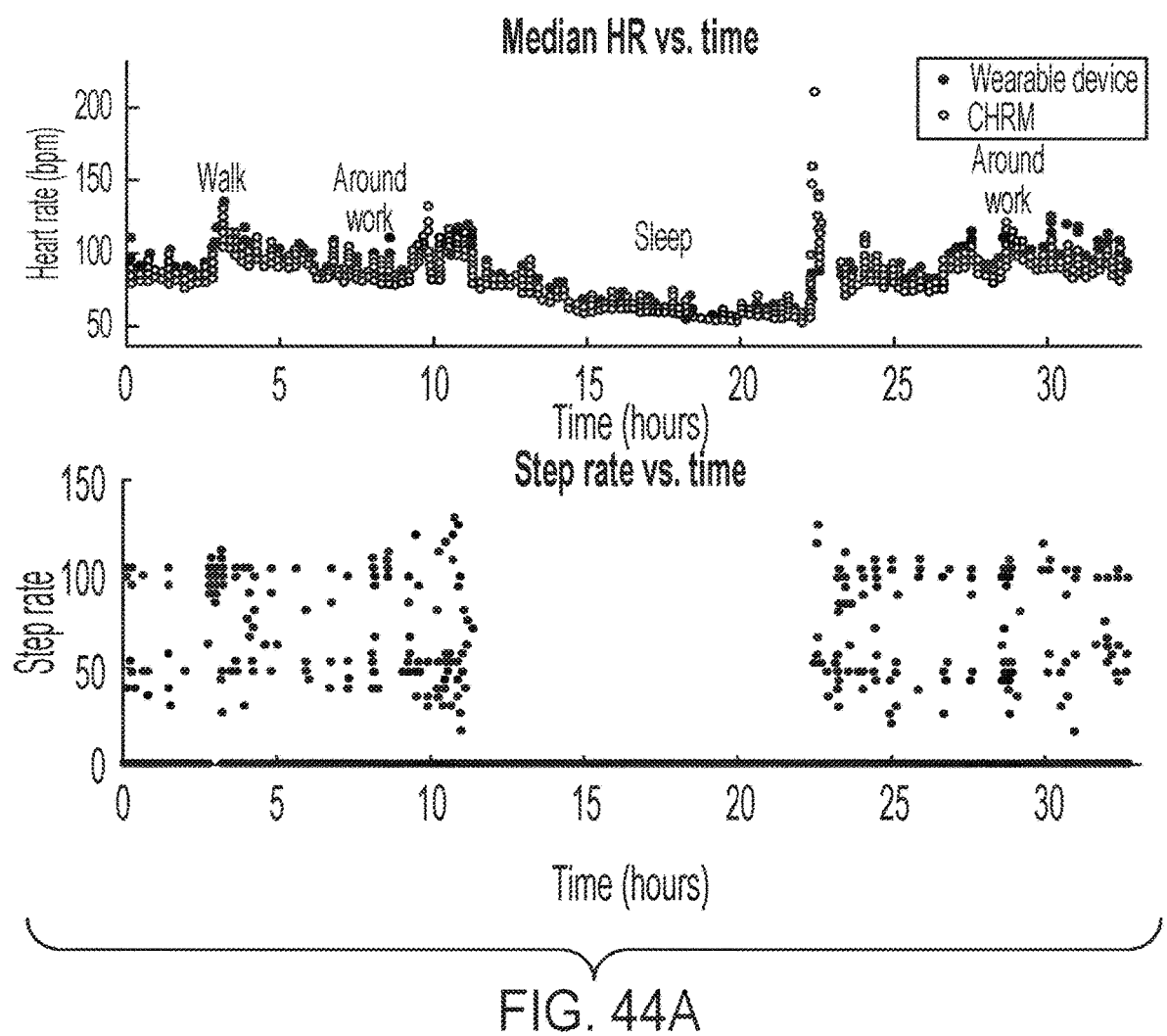
Figure 44B:
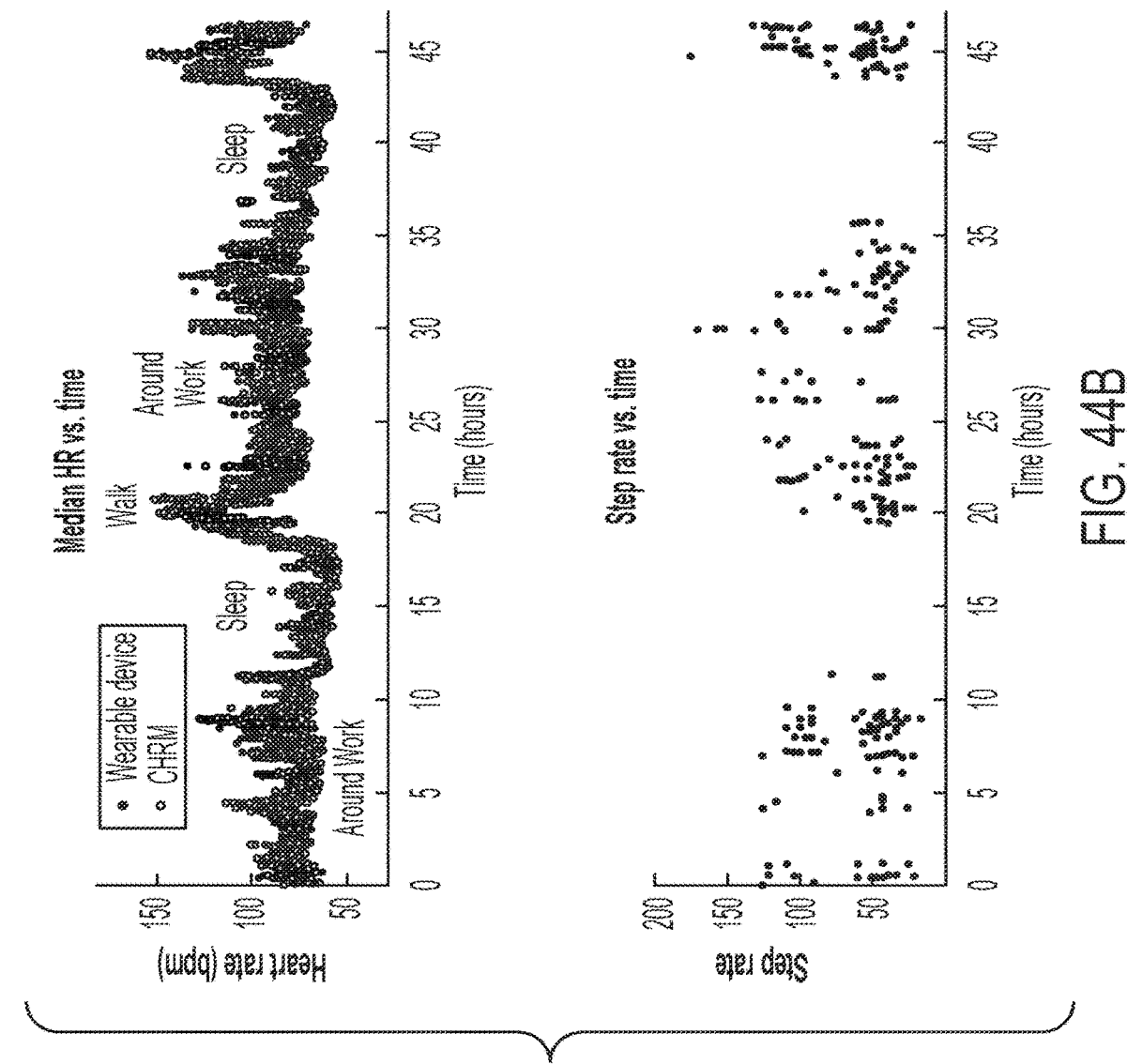
Figure 44C:
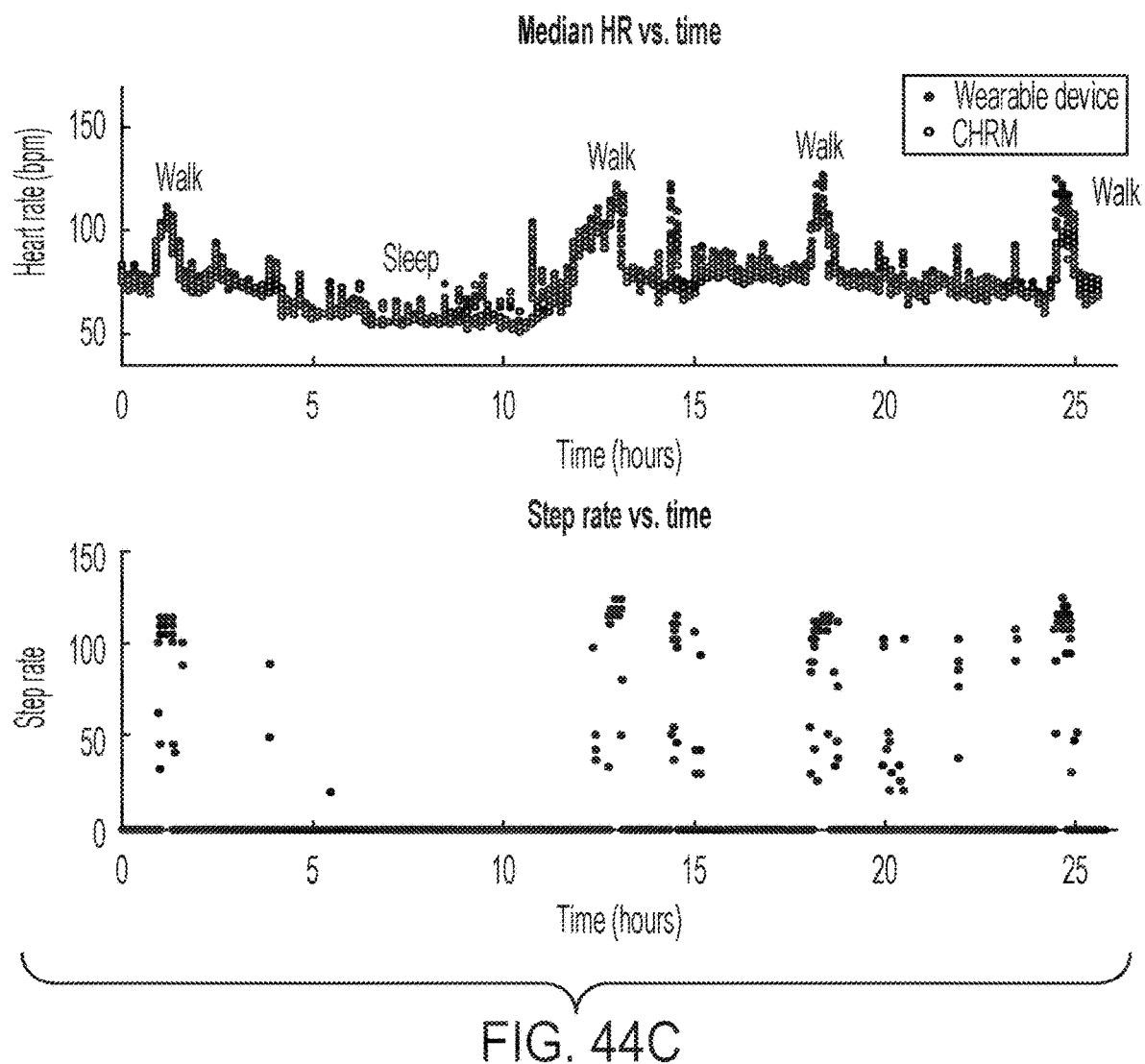
Figure 44D:
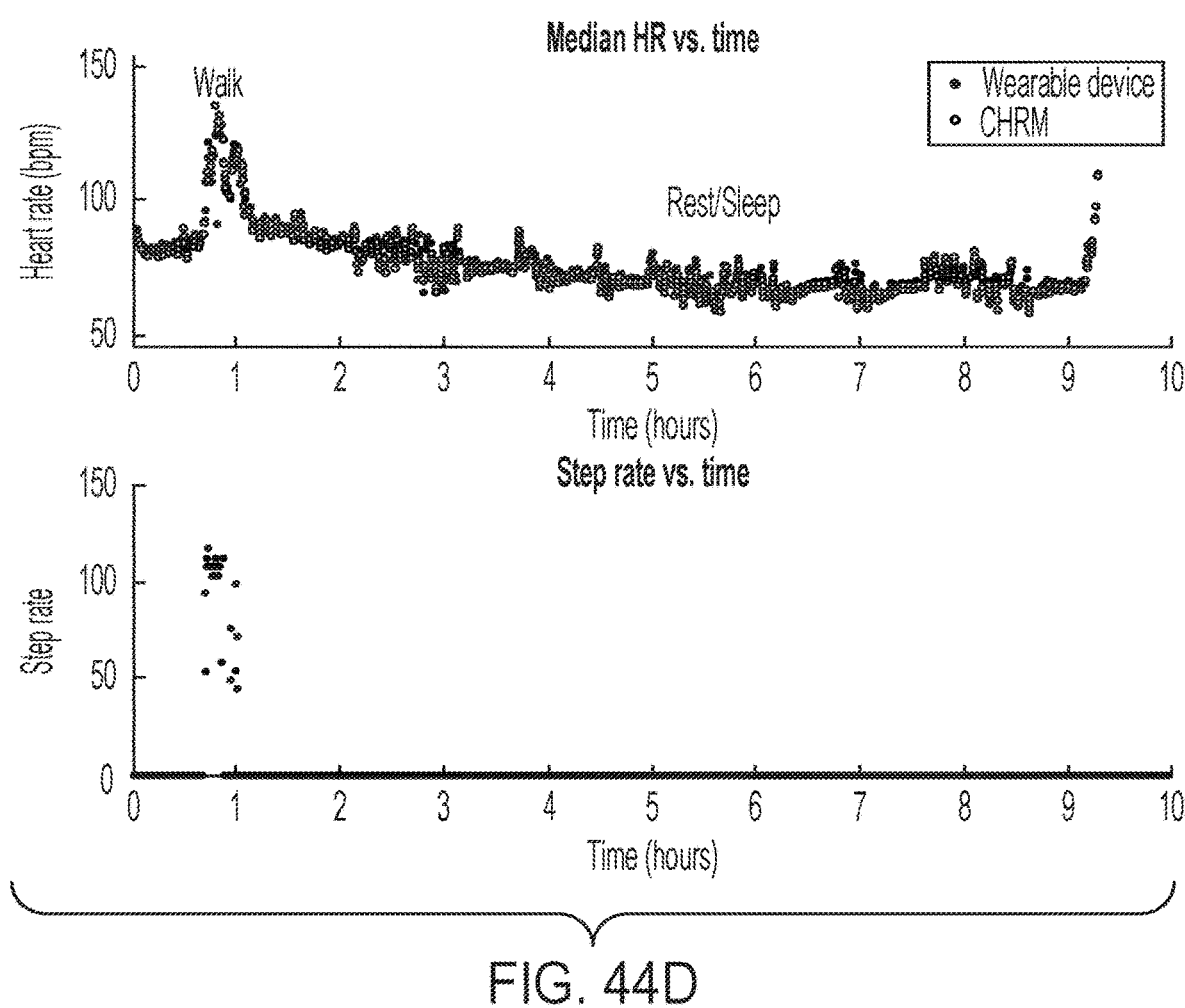
Figure 44E:
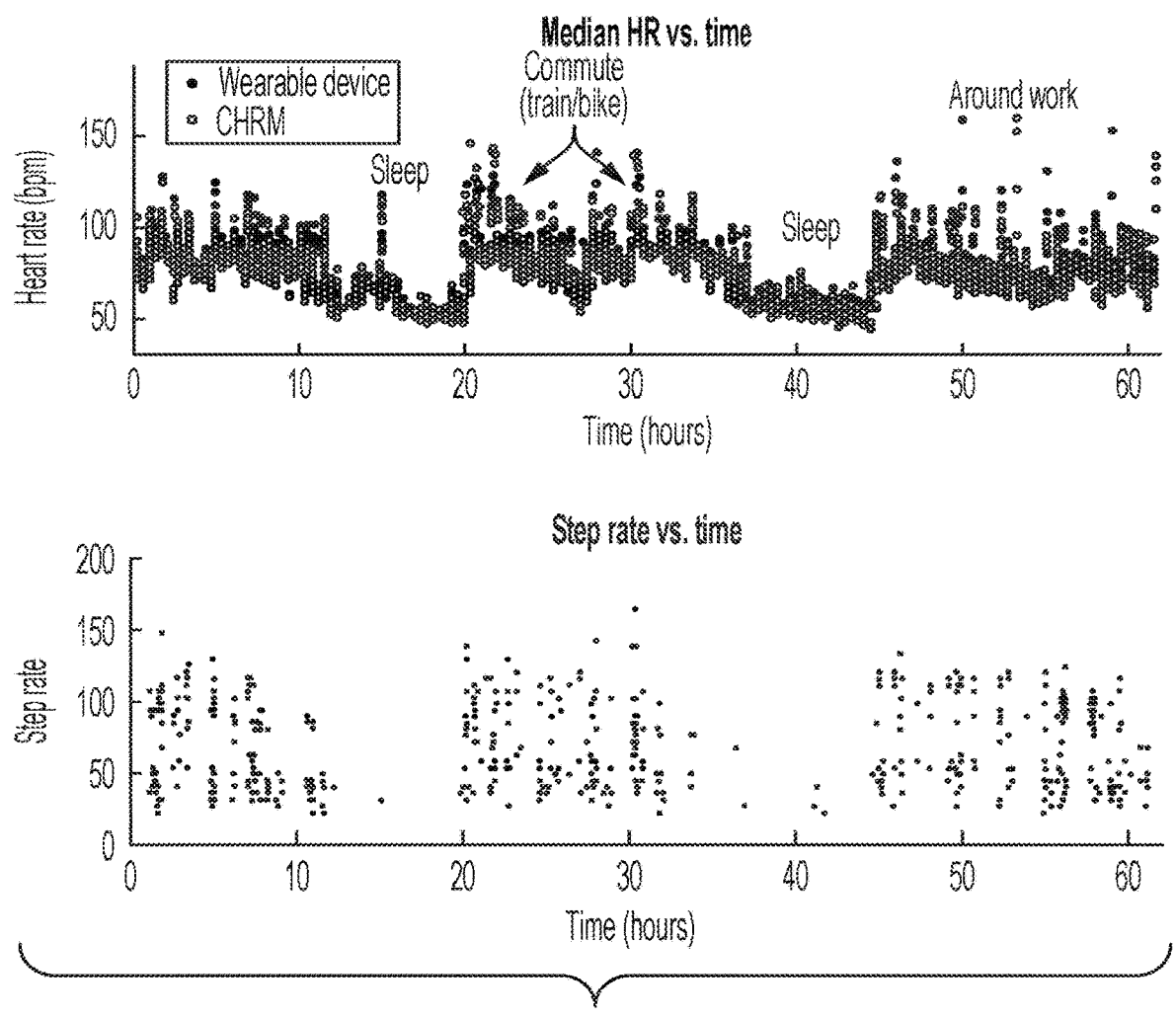
Figure 45A:
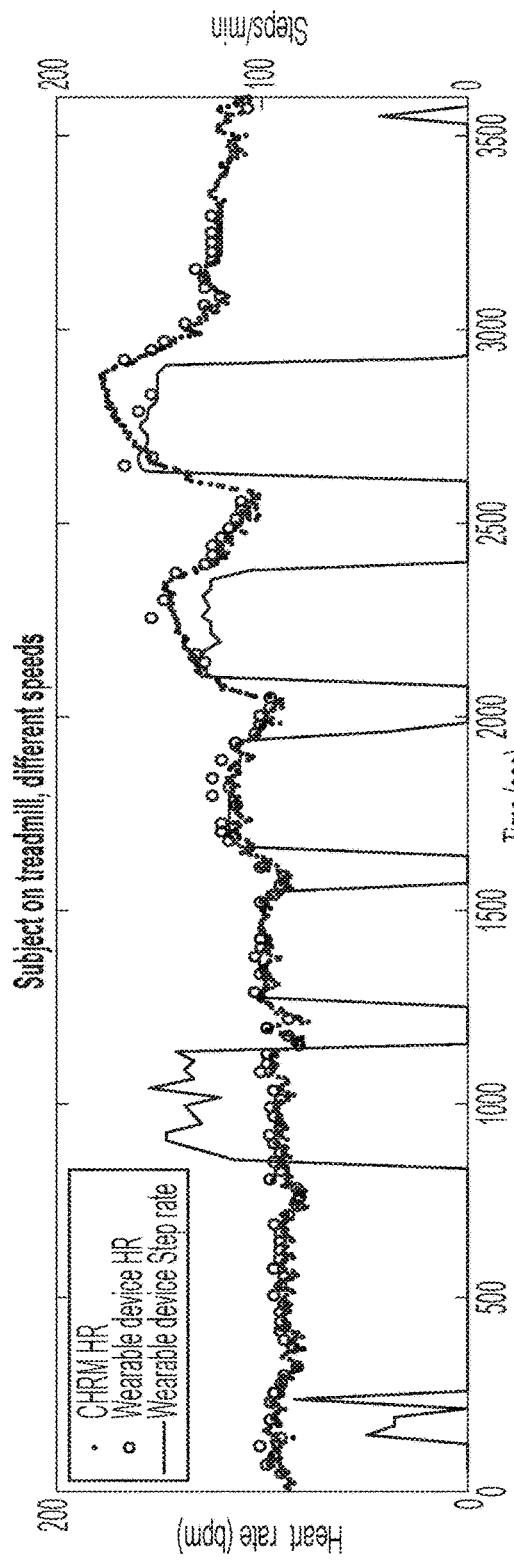
Figure 45B:
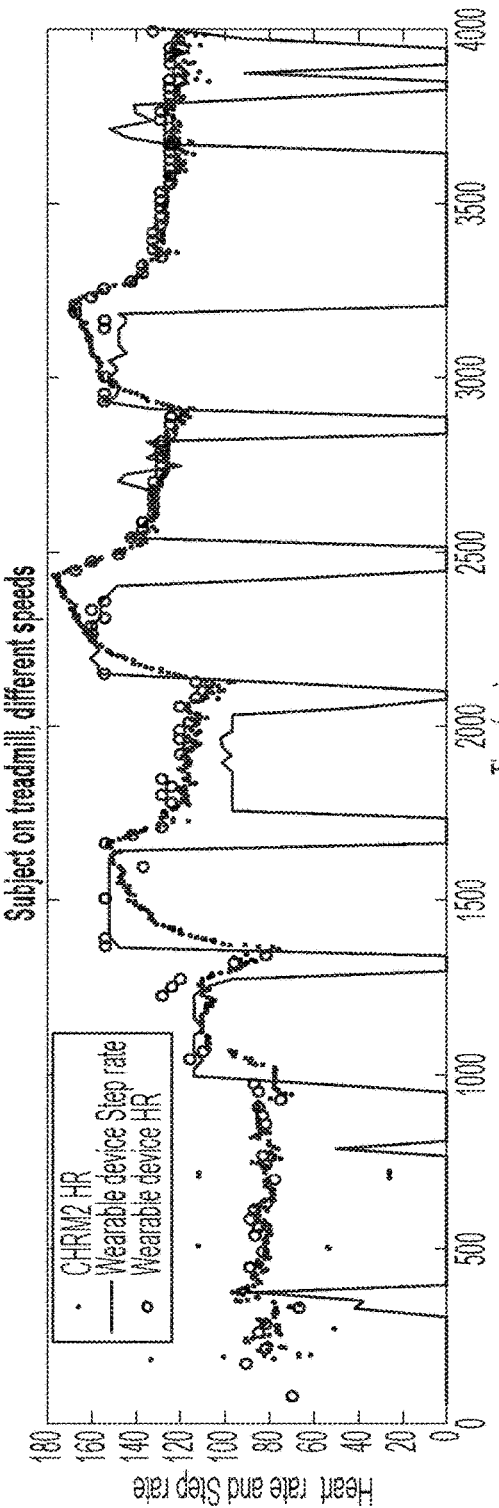
Figure 45D:
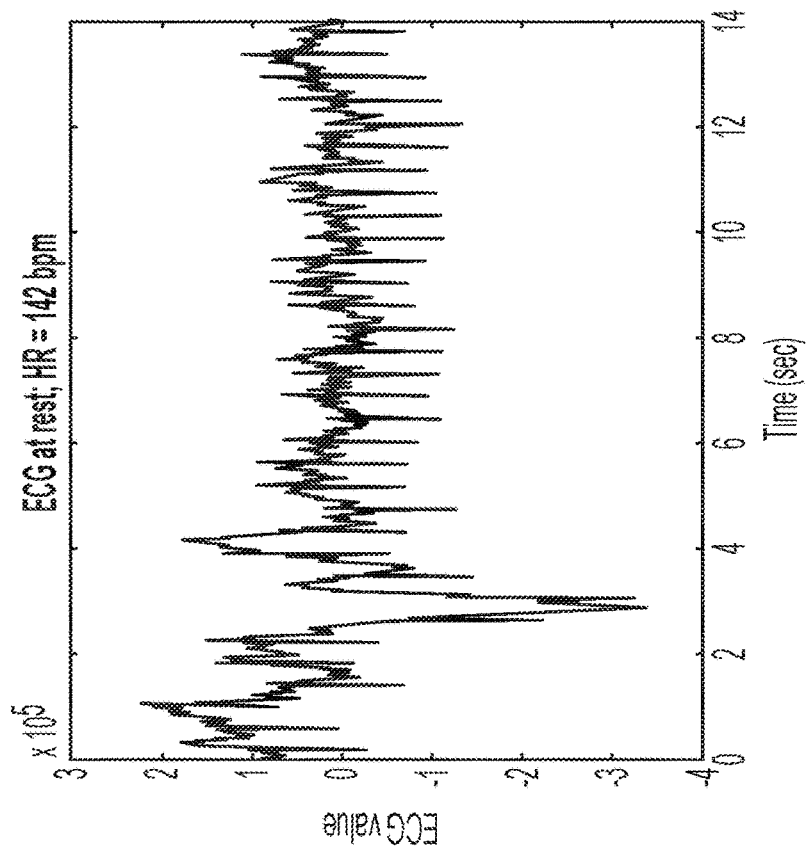
Figure 45C:
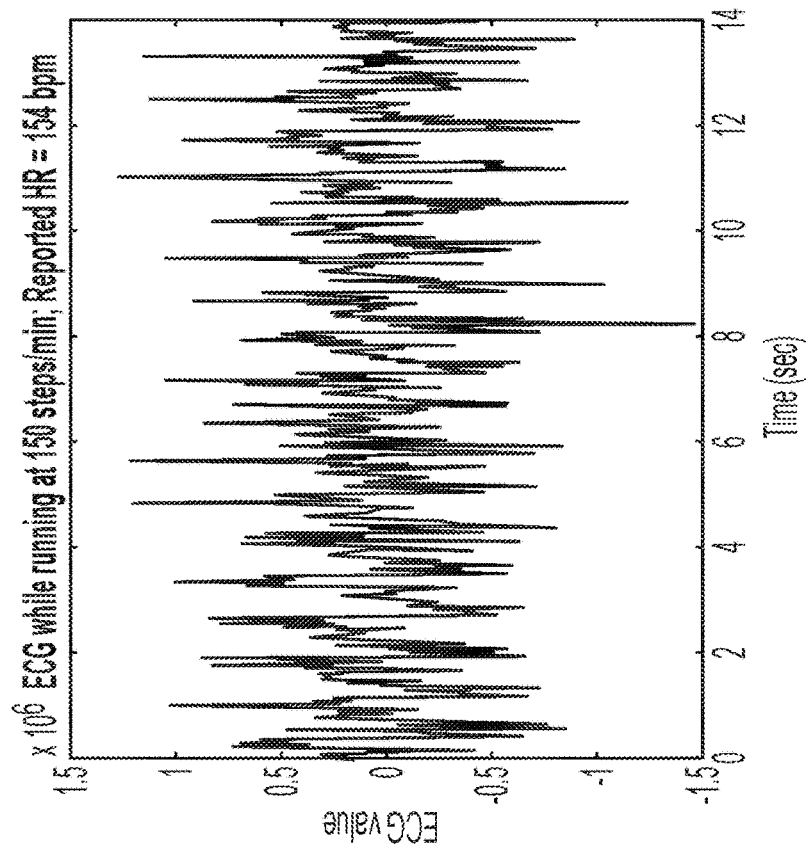

The top of each of FIGS. 44A-E illustrate examples of ECG data collected using the HR algorithm on the wearable device and the CHRM for various patients. Namely, FIG. 44A illustrates the results of patient 2, FIG. 44B illustrates the results of patient 3, FIG. 44C illustrates the results of patient 4, FIG. 44D illustrates the results of patient 8, and FIG. 44E illustrates the results of patient 7. As illustrated in FIGS. 44A-E, the heart rate metric value output by the HR algorithm can be predictable and reliable during different activities. Additionally, the bottom of each of FIGS. 44A-E ited measurement drop-outs. As illustrated, the HR algorithm can detect a heart rate while the patient is performing some activity and the patient may not need to be absolutely still. For example, FIG. 45A illustrates the heart rate versus step rate as step rate increases. FIG. 45B illustrates that there is minimal, if any, data loss during activity of the patient. FIG. 45C illustrates ECG during activity of a patient and FIG. 45D illustrates ECG data during non-activity of a patient.

Raw ECG data, enhanced ECG data, and metrics can be stored in an ECG data record in memory such as, for example, the memory of the wearble device and/or the memory of a remote device. An example of an ECG data record is provided in Table 27.

TABLE 27

ECG data record description

| Output | Description |
|---|---|
| Median heart rate | Median heart rate for the ECG frame |
| Mean heart rate | Mean heart rate for the ECG frame |
| Number of R-waves | Number of R-wave peaks discovered in the ECG frame |
| MAD | Median absolute deviation for the R-R interval vector for the ECG frame |
| Quality Score (QS) | Number of valid sub-frames in the ECG frame |
| Peak Spread (PS) | The difference between the maximum and minimum number of R-wave peaks discovered across sub-frames in the ECG frame |
| Frame Valid | Flag (TRUE/FALSE) indicating whether the heart rate measurement for the ECG frame is valid |

The wearable device can contain a scheduler (e.g., a software module external to the algorithms described herein) which can start and stop ECG data acquisition according to ECG Event Interval and ECG Event Duration programmable parameters. Specifically, the ECG signal can be acquired periodically every ECG Event Interval seconds (e.g., at a fixed sampling rate of 256 Hz) for a duration determined of ECG Event Duration seconds.

Heart Rate Variability

Heart rate variability (HRV) is a variation in the time interval between heart beats as measured by the variation in the R-R interval. HRV has been shown to have clinical significance in both cardiac and psychiatric use cases. For example, abnormal HRV has been shown to be a predictor of mortality after myocardial infarction, depression, anxiety, bipolar disorder, and schizophrenia. HRV can also be used for stress quantification, sleep stage identification, and estimating respiratory rate.

To determine an HRV metric, extended amounts of ECG data may need to be gathered, essentially on the order of minutes. The extended amounts of ECG data can be smoothed and averaged and thereafter the HRV metric can be determined.

The HRV algorithm can receive ECG data and can be distributed across a wearable device 102 and a remote device for execution by a control circuit. For example, the HRV algorithm can be stored in memory 112 and can be utilized by processor 111 to transform ECG data received into a physiological metric, such as, for example, a HRV metric. The HRV algorithm can be stored in memory on the remote device and can process the ECG data on the remote device to transform the ECG data into the physiological metric. In various examples, the HR algorithm can be performed on ECG data on the wearable device and the wearable device can output the resulting data to a remote device for the HRV algorithm to determine an HRV metric from the resulting data.

The wearable device and/or a remote device can calculate the HRV from the ECG data. For example, the wearable device and/or remote device can calculate HRV when HRV mode is enabled via the ECG HRV Interval programmable parameter. When HRV mode is enabled, the wearable device can measure ECG signals and obtain ECG data from the wearable device as described herein.

Referring back to FIG. 15, the wearable device can perform an IEM (ingestible event marker) sniff operation after each ECG frame in physiological data 1506 while in HRV mode. If IEM activity is not detected, the wearable device moves on to the next ECG frame after each ECG HRV gap. If IEM activity is detected by the sniff operation, the wearble device can bail on HRV mode and enter IEM detect mode instead.

HRV metrics can be time domain metrics, frequency domain metrics, non-linear metrics, or other types of metrics. For example, time domain metrics can comprise intervals between normal R-peaks (average N-N interval), a standard deviation of N-N intervals (SDNN), a root mean squared of successive R-R interval differences (RMSSD), a proportion of successive N-N intervals that differ by more than a threshold (e.g., 50 ms) (pNN50: P), an HRV triangular index, and a baseline width of the T-T-interval histogram (TINN). The frequency domain metrics can comprise power of the low-frequency band (LF power), the power of the high-frequency band (HF power), and the ratio of the LF Power to the HF power (LF/HF ratio). The Non-linear metrics can comprise approximate entropy (ApEn) which can measure the regularity and complexity of a time series. The HRV metrics can be computed over short durations (a few minutes) and/or long durations (24 hours).

However, in a discontinuous data environment, gaps in between ECG data can present challenges when calculating HRV metrics. It can be difficult to stitch together the ECG data frames to create an accurate calculation of HRV metrics, because the boundaries of the frames of ECG data may not start or end at the same point in the cardiac muscle cycle. Additionally, in examples where an HRV metric is at least partially calculated on the wearable device, it can be desirable to create a power-efficient algorithm to conserve battery (e.g., simple computations, for example, not doing any complex operations like an FFT, and working with integers instead of floating point operations).

HRV mode can include the following parameters: HRV_Event_Interval (default 30 minutes); HRV_Num_Blocks (default 9); and HRV_Block_Gap (default 4 sec).

Every HRV_Event_Interval seconds, the wearable device can enter HRV mode, where discontinuous ECG signals can be acquired (e.g., 14 second frames) HRV_Num_Blocks times, with the ECG signals can be separated by HRV_Block_Gap seconds. After every frame of ECG signal, the wearable device can exit HRV mode if there is a successful IEM sniff. At the end of HRV mode, the ECG data from the acquired ECG signals will be aggregated and processed to extract relevant HRV metrics. This step maybe relegated to the backend (e.g., the remote device).

Referring to FIG. 46, in order to determine HRV metrics, the HRV algorithm receives discontinuous data comprising frames of ingestible sensor data and frames of physiological data. The HRV algorithm parses the physiological data including parsing out ECG data, index of every detected R peak in the ECG data (RWV), and impedance (IMP) data (e.g., a separate measurement), 4602. The ECG data can be processed with the HR algorithm according to FIG. 23. Thereafter, referring back to FIG. 46, frames of ECG data can be grouped into blocks, 4604. For example, the number of frames grouped together in a block can be set by the parameter HRV_Num_Blocks. The number of frames grouped together can be at least two and the default value can be 9 frames. The frames in the block can be sequentially positioned.

Thereafter, the HRV algorithm can determine if a number of frames in the block that have valid heart rate metrics values is greater than or equal to a validity threshold, 4606. The validity of each frame can determined by the processor and according to Equation 26. In various examples, the validity threshold can be 8 (e.g., 90% of the total blocks). If the number of frames in the block that have valid heart rate metric values is less than the validity threshold, the block can be skipped and a HRV metrics may not be determined from the block. In this way, the HRV algorithm can lower power consumption on the wearable device by not processing invalid blocks of ECG data.

However, if the number of frames in the block that have valid heart metric values is greater than or equal to the validity threshold, the HRV algorithm can proceed to determine if impedance data before and/or after the block is valid, 4608. If the nearest impedance data before and/or after the block is not valid, the block can be ignored and HRV metrics may not be determined from the block. For example, if the median of a moving window of consecutive impedance values (e.g., 5) are greater than an impedance threshold (e.g., 10 kOhms), the block can be considered invalid and HRV metrics may not be determined from the block. Then, after one impedance measurement below the impedance threshold, the block can be used for HRV metrics. In this way, the HRV algorithm can conserve power when a high impedance is measured (e.g., electrodes off the skin) and rapidly return to calculating HRV metrics after the high impedance event ends (e.g., electrodes back on the skin).

However, if the nearest impedance data before and/or after the block is valid, the HRV algorithm can process the block and reject any frames comprising outlier heart rates in the block of ECG data, 4610. An outlier heart can be based on an incorrectly identified R peak, or data with irregularly spaced R peaked (e.g., arrhythmia). The outlier heart rate can be determined based on a median absolute deviation. Thereafter, the HRV algorithm can determine if a number of frames in the block that are good (e.g., do not comprise any outlier heart rates), 4612. In various examples, the good threshold can be 8. If the number of frames in the block that are good is less than the good threshold, the block can be ignored and HRV metrics may not be determined from the block.

However, if the number of frames in the block that are good is greater than or equal to the good threshold, the HRV algorithm can aggregate the R-wave data from all good frames in the block of ECG data, 4614. Thereafter, the aggregated R-wave data can be processed through R-R cleaning algorithms, 4616.

The R-R cleaning algorithms can comprise a merge twin intervals algorithm, a split tall intervals algorithm, an absorb short intervals algorithm, and a bimodal detection algorithm (e.g., the bimodal amplitude detector as described herein). The R-R cleaning algorithms can be applied to the aggregated R-wave data on the processor on the wearable device and/or on a processor on a remote device. Additionally, the R-R cleaning algorithms can be applied at the frame level to reduce the number of outliers in heart rate reporting.

The merge twin intervals algorithm can merge two short R-R intervals sandwiched between two longer RR-intervals. For example, two short R-R intervals $(Xn, Xn_{+1})$ sandwiched between two longer R-R intervals $(Xn_{-1}, Xn_{+2})$ can be merged to make one R-R interval $(Xn+Xn_{+1})$ if Equation 29 is valid.

$$(Xn+Xn_{+1})<1.6*(Xn_{-1}+Xn_{+2}) \quad \text{Equation 29}$$

The split tall intervals algorithm can split a tall R-R interval sandwiched between two shorter intervals into two intervals. For example, one tall R-R interval $(Xn)$ sandwiched between two shorter R-R intervals $(Xn_{-1}, Xn_{+1})$ can be split into two (2 of Xn/2) if Equation 30 is valid.

$$Xn>0.9*(Xn-1+Xn+1) \quad \text{Equation 30}$$

The absorb short intervals algorithm can absorb a short interval sandwiched between two longer R-R intervals. For example, one short R-R interval $(Xn)$ sandwiched between two longer R-R intervals $(Xn_{-1}, Xn_{+1})$ can be absorbed into the second long interval (e.g., remove Xn and change $Xn_{+1}$ to $(Xn_{+1}+Xn)$) if Equation 31 is valid.

$$Xn<0.25*(Xn-1+Xn+1) \quad \text{Equation 31}$$

Thereafter, the HRV metrics can be calculated from the cleaned R-wave data. For example, the mean R-R interval and SDNN can be calculated, 4618. However, in order to calculate the RMSSD, deltaR-R cleaning of the cleaned R-wave data may be required in order to remove outlier rejection based on median/MAD. Additionally, the cleaned R-wave data can be interpolated for spectral frequency estimation and frequency domain measurements. In various examples, the HRV metrics can be a backend step (e.g., on the remote device) that may not be performed in real time and thus, can conserve battery.

Additionally, the HRV algorithm can utilize discontinuous data comprising frames of ingestible sensor data and frames of physiological data in an efficient manner that may not require large amounts of processing power. That is, the HRV algorithm can piece and/or stitch together the discontinuous data and output an accurate physiological metric, such as, an HRV metric.

The HRV metrics were measured from 8 different patients (e.g., subjects) who wore a wearable device attached to the torso and the CHRM for approximately 24 hours under free living conditions. The wearable device was programmed to acquire an ECG signal every 20 seconds. Accelerometer data was acquired every minute. Impedance measurements were made every 20 minutes. IEM measurements were disabled during the tests. Metric data was extracted from the CHRM using comparative software. Data from the wearable device and the CHRM was post processed in Python and was compared according to the data flow illustrated in FIG. 47.

Table 28 illustrates the spearman correlation coefficients comparing HRV metrics from the CHRM data which utilizes continuous ECG data with the wearable device utilizing discontinuous ECG data from the wearable device utilizing algorithms according to the present disclosure without subjecting the discontinuous ECG data to R-R cleaning algorithms or deltaR-R cleaning algorithms. The R-R cleaning algorithms and/or delta R-R cleaning algorithms can be a sub-component of the HRV algorithm.

TABLE 28

| Spearman correlation coefficients | | | |
| --- | --- | --- | --- |
| Patient | Mean R-R | SDNN | RMSSD |
| 1 | 0.96 | 0.08 | −0.22 |
| 2 | 0.94 | 0.28 | 0.22 |
| 3 | 0.92 | 0.45 | 0.33 |

TABLE 28-continued

| | Spearman correlation coefficients | | |
|---|---|---|---|
| Patient | Mean R-R | SDNN | RMSSD |
| 4 | 0.97 | 0.48 | 0.09 |
| 5 | 0.98 | 0.55 | 0.24 |
| 6 | 0.88 | 0.28 | 0.15 |
| 7 | 0.92 | 0.40 | 0.15 |
| 8 | 0.94 | 0.39 | −0.19 |

As illustrated, the Mean R-R data shows a strong linear correlation between the discontinuous data and continuous data since the spearman correlation coefficient for the mean R-R is high (e.g., closer to 1). Thus, the mean or median heart rate may be determined accurately from the discontinuous data without any further HRV cleaning.

However, there were poor linear correlation between the SDNN and RMSSD between the continuous data and discontinuous data since the spearman correlation coefficient for the SDNN and RMSSD is closer to 0.

Table 29 illustrates the spearman correlation coefficients comparing HRV metrics from the CHRM data which utilizes continuous ECG data with the wearable device utilizing discontinuous ECG data with subjecting the discontinuous ECG data to R-R cleaning algorithms only.

TABLE 29

| | Spearman correlation coefficients | | |
|---|---|---|---|
| Patient | Mean R-R | SDNN | RMSSD |
| 1 | 0.96 | 0.08 | −0.22 |
| 2 | 0.94 | 0.28 | 0.22 |
| 3 | 0.92 | 0.45 | 0.33 |
| 4 | 0.97 | 0.48 | 0.09 |
| 5 | 0.98 | 0.55 | 0.24 |
| 6 | 0.88 | 0.28 | 0.15 |
| 7 | 0.92 | 0.40 | 0.15 |
| 8 | 0.94 | 0.39 | −0.19 |

As illustrated, the R-R cleaning algorithms have a minimal impact on the spearman correlation coefficients for the mean R-R. However, there is a significant improvement in the correlation coefficients (e.g., closer to 1) for the SDNN and RMSSD.

Table 30 illustrates the spearman correlation coefficients comparing HRV metrics from the CHRM data which utilizes continuous ECG data with the wearable device utilizing discontinuous ECG data with subjecting the discontinuous ECG data to deltaR-R cleaning algorithms only.

TABLE 30

| | Spearman correlation coefficients | | |
|---|---|---|---|
| Patient | Mean R-R | SDNN | RMSSD |
| 1 | 0.96 | 0.08 | 0.41 |
| 2 | 0.94 | 0.28 | 0.76 |
| 3 | 0.92 | 0.45 | 0.59 |
| 4 | 0.97 | 0.48 | 0.82 |
| 5 | 0.98 | 0.55 | 0.78 |
| 6 | 0.88 | 0.28 | 0.72 |
| 7 | 0.92 | 0.40 | −0.02 |
| 8 | 0.94 | 0.39 | 0.60 |

As illustrated, the deltaR-R cleaning algorithms have a minimal impact on the spearman correlation coefficients for the mean R-R and SDNN. However, there is a significant improvement in the spearman correlation coefficients (e.g., closer to 1) for the RMSSD compared to no cleaning and for some patients, compared to R-R cleaning only.

Table 31 illustrates the spearman correlation coefficients comparing HRV metrics from the CHRM data which utilizes continuous ECG data with the wearable device utilizing discontinuous ECG data with subjecting the discontinuous ECG data to R-R cleaning algorithms and deltaR-R cleaning algorithms.

TABLE 31

| | Spearman correlation coefficients | | |
|---|---|---|---|
| Patient | Mean R-R | SDNN | RMSSD |
| 1 | 0.98 | 0.56 | 0.34 |
| 2 | 0.97 | 0.64 | 0.76 |
| 3 | 0.95 | 0.77 | 0.58 |
| 4 | 0.97 | 0.76 | 0.84 |
| 5 | 0.98 | 0.73 | 0.78 |
| 6 | 0.93 | 0.60 | 0.71 |
| 7 | 0.93 | 0.63 | 0.03 |
| 8 | 0.92 | 0.49 | 0.83 |

As illustrated, utilizing both algorithms (i.e., R-R and DeltaR-R) has a minimal impact on the spearman correlation coefficients for the mean R-R and SDNN compared to R-R cleaning only. However, the spearman correlation coefficients improved (e.g., closer to 1) for the RMSSD compared to deltaR-R cleaning algorithms only for some patients. The deltaR-R cleaning algorithm can have a larger effect on the RMSSD calculations than R-R cleaning.

Table 32 illustrates the spearman correlation coefficients comparing HRV metrics from the CHRM data which utilizes continuous ECG data with the wearable device utilizing discontinuous ECG data with subjecting the discontinuous ECG data to R-R cleaning algorithms and deltaR-R cleaning algorithms where data comprises gaps (e.g., gaps were added to data from the CHRM to match the same timing as data from the ECG data from the wearable device according to the present disclosure).

TABLE 32

| | Spearman correlation coefficients | | |
|---|---|---|---|
| Patient | Mean R-R | SDNN | RMSSD |
| 1 | 0.99 | 0.57 | 0.39 |
| 2 | 0.94 | 0.58 | 0.71 |
| 3 | 0.97 | 0.77 | 0.58 |
| 4 | 0.97 | 0.74 | 0.83 |
| 5 | 0.99 | 0.74 | 0.77 |
| 6 | 0.95 | 0.59 | 0.70 |
| 7 | 0.94 | 0.68 | 0.04 |
| 8 | 0.94 | 0.52 | 0.82 |

Table 33 illustrates the mean absolute error percent and median absolute error percent when comparing a calculated RMSSD from the wearable device and a reported RMSSD from the CHRM.

TABLE 33

| Mean absolute error percent and median absolute error percent | | |
|---|---|---|
| Patient | Mean abs % error | Median abs % error |
| 1 | 5.1 | 1.1 |
| 2 | 1.1 | 0.5 |

TABLE 33-continued

Mean absolute error percent and median absolute error percent

| Patient | Mean abs % error | Median abs % error |
|---|---|---|
| 3 | 5.2 | 1.2 |
| 4 | 3.5 | 0.7 |
| 5 | 1.5 | 0.8 |
| 6 | 2.1 | 0.8 |
| 7 | 1.6 | 0.9 |
| 8 | 4.8 | 2.7 |

FIG. 48 illustrates an example of an HRV metric plot for patient 5 and how the algorithms according to the present disclosure that utilize discontinuous data compares to comparative algorithms that utilize continuous data.

Rest

A processor on the wearable device and/or a remote device can process the accelerometer data and ECG data in order to determine rest and/or a resting heart rate. The resting algorithm can receive accelerometer data and ECG data, and can be distributed across a wearable device 102 and a remote device for execution by a control circuit. For example, the resting algorithm can be stored in memory 112 and can be utilized by processor 111 to transform accelerometer data and ECG data into a physiological metric, such as, for example, a rest metric. In various examples, the resting algorithm can be stored on a remote device and used in combinationed with other metrics. For example, the resting algorithm can be used to clean other metric outputs, such as, discarding any steps that were detected during rest or determining resting heart rate from heart rate metrics.

Based on the acceleration data, a patient can be determined to be resting. Namely, a patient can be determined to be resting based on the body angle and total activity of the patient. For example, if the patient is both laying down based on a body angle and inactive based on the total activity, the patient and associated physiological data can be classified as resting by a resting algorithm. In this way, the rest metric can be used to lower power consumption (e.g., measurement frequency) in the wearable device during periods of rest and/or selectively use or ignore data obtained during periods of rest.

Referring to FIG. 49, the resting algorithm can receive accelerometer data. The resting algorithm can determine the body angle of the patient based on the accelerometer data and the reference vector, 4902. The body angle can be mean averaged (e.g., box car filter) over a mean period of time and mean body angle data (ba_avg) can be output, 4904. The mean period of time can be a sliding time window, where the window length is parametrized according to a programmable variable body_angle_smoothing_size_mins. The mean body angle data at step 4904 can be time stamped with a time in the center of the window length.

Thereafter, the mean body angle data can be added to an aggregation window, 4906. The resting algorithm can then determine an aggregation period of time covered by the mean body angle data in the aggregation window. The resting algorithm can determine if the aggregation period of time is greater than or equal to an aggregation threshold, 4908. The aggregation threshold can be defined according to a programmable parameter aggregation_period_mins. If the aggregation period of time is less than the aggregation threshold, the resting algorithm can obtain more acceleration data.

Otherwise, if the aggregation period of time is greater than or equal to the aggregation threshold, the resting algorithm can calculate the data ratio of the actual number of data points in the aggregation window versus the expected number of data points. The resting algorithm compares the data ratio to a programmable data threshold (e.g., data_missing_frac) to determine if the data in the aggregation window can be reliably used, 4910. If the data ratio is less than the data threshold, the resting algorithm can obtain more acceleration data.

However, if the data ratio is greater than or equal to the data threshold, resting algorithm can classify the mean body angle data in the aggregation window based on the acceleration data. For example, mean body angle data (ba_avg) can be classified as laying down if the mean averaged body angle is greater than a first angle threshold (e.g., recumbent_angle_min, −30°) and less than a second angle threshold. (e.g., recumbent_angle_max, 30°). Otherwise, the data can be classified as not laying down. Thereafter, the resting algorithm can determine if the number of mean averaged body angle data in the aggregation window classified as laying down is greater than or equal to a recumbent threshold, 4912. The recumbent threshold can be a programmable parameter ("minimum_recumbent_frac"). If the number of mean averaged body angle data in the aggregation window classified as laying down is less than the recumbent threshold, the data in the aggregation window can be determined to not correspond to a lying down position of the patient, 4914. Otherwise, the resting algorithm can proceed to step 4926.

In addition to the body angle, the resting algorithm can account for the total activity of the accelerometer data. Namely, the resting algorithm can calculate the total activity from the accelerometer data, 4916. The resting algorithm can calculate the punctuated inactivity data from the total activity data, 4918. Namely, as illustrated in FIG. 50, the resting algorithm calculates a standard deviation over a SD period of time, 5002. The SD period of time can be a sliding time window, where the window length is parametrized according to a programmable variable acc_std_win_size_mins. The standard deviation can be taken of each axis in the total activity data individually and sum the standard deviations of each axis.

The resting algorithm can remove values in from the summed standard deviation data that are greater than or equal to an SD threshold, 5004. The SD threshold can be parameterized according to a programmable parameter std_thresh. Removing values greater than or equal to the SD threshold can limit the effect of an occasional shift in orientation (e.g., rotation) by a patient during a resting period which can generate a spike in the standard deviation. The removed values can be replaced with the immediately prior measured value.

Thereafter, the standard deviation data can be averaged over a sum period of time, 5006. The sum period of time can be parameterized according to a programmable parameter activity_smoothing_size_mins. The standard deviation data can be added to an aggregation window, 5008.

Referring back to FIG. 49, after adding the standard deviation data to an aggregation window, the resting algorithm can determine an aggregation period of time covered by the standard deviation data in the aggregation window and if the aggregation period of time is greater than or equal to the aggregation threshold, 4920. If the aggregation period of time is less than the aggregation threshold, the resting algorithm can obtain more acceleration data.

Otherwise, if the aggregation period of time is greater than or equal to the aggregation threshold, the resting algorithm can calculate the data ratio of the actual number of data points in the aggregation window versus the expected number of data points. The resting algorithm compares the data ratio to a programmable data threshold to determine if the data in the aggregation window can be reliably used, 4922. If the data ratio is less than the data threshold, the resting algorithm can obtain more acceleration data.

However, if the data ratio is greater than or equal to the data threshold, the resting algorithm can classify the standard deviation data in the aggregation window. For example, standard deviation data can be classified as inactive if the mean averaged body angle is less than or equal to a SD threshold (e.g., smoothed_acc_std_max, 0.065). Otherwise, the standard deviation data can be classified as active. Thereafter, the resting algorithm determines if the number of standard deviation data in the aggregation window classified as inactive is greater than or equal to an inactive threshold, 4924. The inactive threshold can be a programmable parameter ("minimum_inactive_frac"). If the number of standard deviation data in the aggregation window classified as inactive is less than the inactive threshold, the data in the aggregation window can be determined to be active, 4914. If the number of standard deviation data in the aggregation window classified as inactive is greater than or equal to the inactive threshold, the data in the aggregation window can be determined to be inactive and the resting algorithm can proceed to step 4926.

Following a classification of the acceleration data as both lying down and inactive, the acceleration data can be further classified as resting data, 4926. The resting data classification can be stored in memory 4928. In this way, the resting algorithm can utilize discontinuous data comprising ingestible sensor data and physiological data.

The resting algorithm can have the programmable parameters as shown in Table 34.

TABLE 34

Programmable Parameters for the Resting Algorithm
Parameter aggregation_period_mins
data_missing_frac
body_angle_smoothing_size
recumbent_angle_min
recumbent_angle_max
minimum_recumbent_frac
acc_std_win_size_mins
activity_smothing_size_mins
std_thresh
smoothed_acc_std_max
minimum_inactive_frac The wearable device can determine if accelerometer data should be classified as resting data at a regular interval such as, for example, every 10 minutes. Resting data can be further defined as sleep. In various examples, primary rest can be calculated as the largest block of data classified as resting data in a 24 hour period (e.g., between 3 PM and 3 PM). Non-adjacent rest segments can be appended on either side of the primary rest if they are separated by less than a separation threshold (e.g., 30 minutes) of non-rest and the gap is not larger than the new rest block being added.

A resting heart rate can be a heart rate metric calculated during a period of minimal physical activity such as, for example, sleep. That is, the resting heart rate can be calculated from ECG data that corresponds to accelerometer data classified as resting data (e.g., based on a time stamp). In various examples, ECG data can be classified as resting data based on associated accelerometer data (e.g., based on a time stamp).

The resting heart rate can be calculated from sliding windows of medians of resting heart rate metric values. The resting heart rate can be defined as the lowest local median. Other parameters that may be used to define the resting heart rate include the hour to define a new period (e.g., 24 hour period); length of the window to average the heart rate metric values over during rest periods; amount of minutes to slide the window by for the next calculation; and the minimum number of heart rate values to consider a window valid.

Additionally, the resting values can be stored in separate queues from the heart rate metric values since there may not be equal numbers of heart rate values and rest values.

U.S. Provisional Patent Application No. 62/685,855, titled MONITORING A SENSOR ASSEMBLY FOR REPLACEMENT STRIP, filed Jun. 15, 2018; U.S. PCT Application _____, Attorney Docket No. PRTS-220WO, titled MONITORING A SENSOR ASSEMBLY FOR REPLACEMENT STRIP, filed concurrently herewith; U.S. Provisional Patent Application No. 62/685,784, titled RE-WEARABLE PHYSIOLOGICAL MONITORING DEVICE, filed Jun. 15, 2018; and U.S. PCT Application _____, Attorney Docket No. PRTS-228WO, titled RE-WEARABLE PHYSIOLOGICAL MONITORING DEVICE, filed concurrently herewith are each hereby incorporated herein by reference in their entireties.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain functions and/or operations, it will be understood by those skilled in the art that each function and/or operation within such block diagrams, flowcharts, and/or examples can be implemented, individually and/or collectively, by a wide range of hardware, software, firmware, or virtually any combination thereof. Those skilled in the art will recognize that some examples of the forms disclosed herein, in whole or in part, can be equivalently implemented in integrated circuits, as a computer program running on a computer (e.g., as a programs running on a computer system), as a program running on a processor (e.g., as a program running on a microprocessor), as firmware, or as virtually any combination thereof, and that designing the circuitry and/or writing the code for the software and or firmware would be well within the skill of one skilled in the art in light of this disclosure. In addition, those skilled in the art will appreciate that the mechanisms of the subject matter described herein are capable of being distributed as a program product in a variety of forms, and an illustrative form of the subject matter described herein applies regardless of the particular type of signal bearing medium used to actually carry out the distribution.

Instructions used to program logic to perform various disclosed examples can be stored within a memory in the system, such as dynamic random access memory (DRAM), cache, flash memory, or other storage. Furthermore, the instructions can be distributed via a network or by way of other computer-readable media. Thus a machine-readable medium may include any mechanism for storing or transmitting information in a form readable by a machine (e.g., a computer), including, but not limited to, floppy diskette, optical disk, compact disc read-only memory (CD-ROM), magneto-optical disk, read-only memory (ROM), random access memory (RAM), erasable programmable read-only memory (EPROM), electrically erasable programmable read-only memory (EEPROM), magnetic or optical card, flash memory, or a tangible, machine-readable storage used in the transmission of information over the Internet via electrical, optical, acoustical, or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or FPGA), state machine circuitry, firmware that stores instructions executed by programmable circuitry, and any combination thereof. The control circuit may, collectively or individually, be embodied as circuitry that forms part of a larger system, for example, an IC, an ASIC, a SoC, desktop computers, laptop computers, tablet computers, servers, smart phones, etc. Accordingly, as used herein, "control circuit" includes, but is not limited to, electrical circuitry having at least one discrete electrical circuit, electrical circuitry having at least one IC, electrical circuitry having at least one application-specific IC, electrical circuitry forming a general-purpose computing device configured by a computer program (e.g., a general-purpose computer configured by a computer program that at least partially carries out processes and/or devices described herein or a microprocessor configured by a computer program that at least partially carries out processes and/or devices described herein), electrical circuitry forming a memory device (e.g., forms of RAM), and/or electrical circuitry forming a communications device (e.g., a modem, communications switch, or optical-electrical equipment). Those having skill in the art will recognize that the subject matter described herein may be implemented in an analog or digital fashion or some combination thereof.

As used herein, the term "logic" may refer to an app, software, firmware, and/or circuitry configured to perform any of the aforementioned operations. Software may be embodied as a software package, code, instructions, instruction sets, and/or data recorded on non-transitory computer-readable storage medium. Firmware may be embodied as code, instructions or instruction sets, and/or data that are hard-coded (e.g., nonvolatile) in memory devices.

As used herein, the terms "component," "system," "module," and the like can refer to a computer-related entity, either hardware, a combination of hardware and software, software, or software in execution.

As used herein, an "algorithm" refers to a self-consistent sequence of steps leading to a desired result, where a "step" refers to a manipulation of physical quantities and/or logic states that may, though they need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol, which may be capable permitting communication using a Transmission Control Protocol/Internet Protocol (TCP/IP). The Ethernet protocol may comply or be compatible with the Ethernet standard published by the Institute of Electrical and Electronics Engineers (IEEE), titled "IEEE 802.3 Standard," published in December 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001 and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

A component may be referred to herein as "configured to," "configurable to," "operable/operative to," "adapted/adaptable," "able to," "conformable/conformed to," etc. Those skilled in the art will recognize that "configured to"

can generally encompass active-state components, inactive-state components, and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to"). It will be further understood by those skilled in the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include, but not be limited to, systems that have A alone, B alone, C alone, A and B together, A and C together, B and C together, and/or A, B, and C together). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A," "B," or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Any patent application, patent, non-patent publication, or other disclosure material referred to in this specification is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

In summary, numerous benefits have been described that result from employing the concepts described herein. The foregoing description has been presented for purposes of illustration and description. It is not intended to be exhaustive or limiting to the precise examples disclosed. Modifications or variations are possible in light of the above teachings. The examples were chosen and described in order to illustrate principles and practical application to thereby enable one of ordinary skill in the art to utilize the various examples and with various modifications as are suited to the particular use contemplated. It is intended that the claims submitted herewith define the overall scope.

What is claimed is:

1. A system for determining a step count of a patient, the system comprising:
   a wearable device comprising an accelerometer, the wearable device configured to be coupled to a body of the patient and configured to detect discontinuous data utilizing at least the accelerometer, the discontinuous data comprising frames of ingestible sensor data and frames of physiological data of the patient interspersed in time gaps between the frames of the ingestible sensor data; and
   a processor of at least one of the wearable device and a remote device communicatively coupled to the wearable device, where the processor is configured to:
      extract accelerometer data from the physiological data;
      enhance the accelerometer data;
      calculate a number of level crossings in the enhanced accelerometer data by:
         computing initial level crossings in portions of the accelerometer data that are uninterrupted by the ingestible sensor data;
         identifying boundary conditions in the discontinuous data where the physiological data switches to the ingestible sensor data, and the ingestible sensor data switches to the physiological data;
         determining a direction of the level crossing of the accelerometer data at each of the boundary conditions; and
         incrementing the number of level crossings responsive to a determination a level crossing at the end of a first frame of physiological data is in the same direction as a level crossing at the start of a second frame of physiological data, the first and second frames being sequentially positioned in the physiological data; and
      determine the step count in a speed range of 80 to 150 steps per minute using the calculated number of level crossings with a mean error of plus or minus 3 percent as measured over at least 1000 steps.

2. The system of claim 1, wherein the processor is configured to enhance the accelerometer data responsive to a determination that a total activity of the accelerometer data is less than or equal to a first threshold and greater than or equal to a second threshold.

3. The system of claim 1, wherein the processor is configured to enhance the accelerometer data comprises the processor configured to process the accelerometer data through at least one of:
   a box car filter;
   an absolute value filter;
   a low pass filter;
   a high pass filter; and
   a mean adjustment.

4. The system of claim 1, further comprising the remote device, wherein the remote device is configured to receive the discontinuous data from the wearable device.

5. The system of claim 1, wherein the ingestible sensor data is generated by an ingestible event marker after contact with a bodily fluid of the patient.

6. The system of claim 1, wherein the wearable device is configured to be removably attached to skin of the patient.

7. The system of claim 1, wherein the processor is configured to detect a change in a slope of the frames of physiological data and increment the number of level crossings responsive to the slope change.

8. A wearable device comprising:
   a disposable component configured to attach to a patient and receive discontinuous data comprising frames of ingestible sensor data and frames of physiological data of the patient interspersed in time gaps between the frames of the ingestible sensor data;
   a reusable component coupled to the disposable component and comprising:
      a processor;
      a non-transitory memory coupled to the processor and configured to store the discontinuous data, wherein the non-transitory memory comprises machine executable instructions that when executed by the processor, cause the processor to:
      extract accelerometer data from the physiological data;
      enhance the accelerometer data;
      calculate a number of level crossings in the enhanced accelerometer data by:
         computing initial level crossings in portions of the accelerometer data that are uninterrupted by the ingestible sensor data;
         identifying boundary conditions in the discontinuous data where the physiological data switches to the ingestible sensor data, and the ingestible sensor data switches to the physiological data;
         determining a direction of the level crossing of the accelerometer data at each of the boundary conditions; and
         incrementing the number of level crossings responsive to a determination a level crossing at the end of a first frame of physiological data is in the same direction as a level crossing at the start of a second frame of physiological data, the first and second frames being sequentially positioned in the physiological data; and
      determine a step count of the patient in a speed range of 80 to 150 steps per minute using the calculated number of level crossings with a mean error of plus or minus 3 percent as measured over at least 1000 steps.

9. The wearable device of claim 8, wherein the machine executable instructions that when executed by the processor, further cause the processor to enhance the accelerometer data responsive to a determination a total activity of the accelerometer data is less than or equal to a first threshold and greater than or equal to a second threshold.

10. The wearable device of claim 8, wherein the machine executable instructions that when executed by the processor, cause the processor to enhance the accelerometer data comprises machine executable instructions that when executed by the processor, further cause the processor to process the accelerometer data through at least one of:
    a box car filter;
    an absolute value filter;
    a low pass filter;
    a high pass filter; and
    a mean adjustment.

11. The wearable device of claim 8, wherein the ingestible sensor data is generated by an ingestible event marker after contact with a bodily fluid of the patient.

12. The wearable device of claim 8, wherein the wearable device is configured to be removably attached to skin of the patient.

13. The wearable device of claim 8, the machine executable instructions that when executed by the processor, further cause the processor to detect a change in a slope of the frames of physiological data and increment the number of level crossings responsive to the slope change.

14. A method of a wearable device for determining a step count of a patient from discontinuous data, the method comprising:
    receiving, by the wearable device, discontinuous data derived from the patient, the discontinuous data comprising frames of ingestible sensor data and frames of physiological data of the patient interspersed in time gaps between the frames of the ingestible sensor data;
    extracting accelerometer data from the physiological data;
    enhancing the accelerometer data;
    calculating a number of level crossings in the enhanced accelerometer data by:
       computing initial level crossings in portions of the accelerometer data that are uninterrupted by the ingestible sensor data;
       identifying boundary conditions in the discontinuous data where the physiological data switches to the ingestible sensor data, and the ingestible sensor data switches to the physiological data;
       determining a direction of the level crossing of the accelerometer data at each of the boundary conditions; and
       incrementing the number of level crossings responsive to a determination a level crossing at the end of a first frame of physiological data is in the same direction as a level crossing at the start of a second frame of physiological data, the first and second frames being sequentially positioned in the physiological data; and
    determining the step count in a speed range of 80 to 150 steps per minute using the calculated number of level crossings with a mean error of plus or minus 3 percent as measured over at least 1000 steps.

15. The method of claim 14, wherein enhancing the accelerometer data is responsive to determining a total activity of the accelerometer data is less than or equal to a first threshold and greater than or equal to a second threshold.

16. The method of claim 14, wherein enhancing the accelerometer data comprises processing the accelerometer data through at least one of:
    a box car filter;
    an absolute value filter;
    a low pass filter;
    a high pass filter; and
    a mean adjustment.

17. The method of claim 14, further comprising generating the ingestible sensor data by contacting an ingestible event marker with a bodily fluid of the patient.

18. The method of claim 14, wherein the wearable device is configured to be removably attached to skin of the patient.

19. The method of claim 14, further comprising detecting a change in a slope of the frames of physiological data and increment the number of level crossings responsive to the slope change.

\* \* \* \* \*